(12) United States Patent
Nishimura et al.

(10) Patent No.: US 7,253,188 B2
(45) Date of Patent: Aug. 7, 2007

(54) AMINOBENZAMIDE DERIVATIVE

(75) Inventors: Teruyuki Nishimura, Tsukuba (JP);
Tomoharu Iino, Tsukuba (JP);
Yasufumi Nagata, Tsukuba (JP);
Jun-ichi Eiki, Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/952,471

(22) Filed: Sep. 27, 2004

(65) Prior Publication Data
US 2005/0282815 A1 Dec. 22, 2005

Related U.S. Application Data

(63) Continuation of application No. PCT/JP03/03656, filed on Mar. 25, 2003.

(30) Foreign Application Priority Data
Mar. 26, 2002 (JP) .......................... P2002-085720

(51) Int. Cl.
| C07D 401/12 | (2006.01) |
| C07D 401/14 | (2006.01) |
| A61K 31/4427 | (2006.01) |
| A61K 31/506 | (2006.01) |
| A61K 31/5377 | (2006.01) |
| A61P 3/04 | (2006.01) |
| A61P 3/10 | (2006.01) |
| C07D 403/12 | (2006.01) |
| C07D 403/14 | (2006.01) |
| C07D 413/12 | (2006.01) |
| C07D 413/14 | (2006.01) |
| A61K 31/47 | (2006.01) |
| A61K 31/497 | (2006.01) |
| A61K 31/501 | (2006.01) |

(52) U.S. Cl. ................... 514/336; 546/268.1; 546/139; 546/152; 544/238; 544/333; 544/405; 544/111; 514/231.5; 514/252.01; 514/252.1; 514/256; 514/307; 514/311

(58) Field of Classification Search ............. 546/268.1; 514/336
See application file for complete search history.

(56) References Cited
FOREIGN PATENT DOCUMENTS

| JP | 58-069812 A | 4/1983 |
| JP | 64-025764 A | 1/1989 |
| WO | WO-00/26202 A1 | 5/2000 |
| WO | WO-00/039118 A1 | 7/2000 |
| WO | WO-00/58293 A1 | 10/2000 |
| WO | WO-01/10865 A1 | 2/2001 |
| WO | WO-01/44216 A1 | 6/2001 |

OTHER PUBLICATIONS

Hasan et al., Molecular Interventions,3(7) : 367-370, 2003.*

(Continued)

Primary Examiner—Venkataraman Balasubramanian
(74) Attorney, Agent, or Firm—Richard C. Billups; Catherine D. Fitch

(57) ABSTRACT

This invention relates to a novel compound represented by the formula (I):

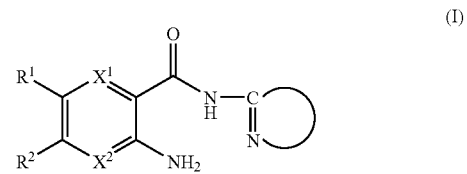

or a pharmaceutically acceptable salt thereof,
wherein
$R^1$ is —S(O)p-A, —S—(O)q-B or —O-D, wherein p and q, which are the same or different, each represent an integer from 0 to 2, A is a straight chain C1-C10 alkyl group which may be substituted by $R^{10}$, and B and D each independently represent $R^{12}$ which may be substituted by $R^{10}$;
$R^2$ is a hydrogen atom, a halogen atom, or a straight chain or branched C1-C6 alkyl group which may be substituted by $R^{10}$;
$X^1$ and $X^2$ each independently represent N or CH, but cannot both be N;
the formula (II):

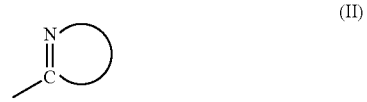

shows a monocyclic or bicyclic heteroaryl group which has a nitrogen atom adjacent to the carbon atom bonded to the amide group, and the heteroaryl group may be substituted by $R^{10}$;
$R^{10}$ is $R^{11}$, or a hydrocarbon group which may be substituted by $R^{11}$;
$R^{11}$ is, for example, a hydrogen atom or amino; and
$R^{12}$ is, for example, phenyl, thiazolyl, pyridyl or methylene dioxyphenyl.

The compound according to this invention has a glucokinase activation effect, and for example, is useful in the treatment and prevention of diabetes mellitus, and in the prevention of its complications such as diabetic nephropathy, diabetic retinopathy, diabetic neuropathy and diabetic arteriosclerosis.

10 Claims, 1 Drawing Sheet

OTHER PUBLICATIONS

Matschinsky, F.M., Diabetes 51, Supplement 3, S394-S404, 2002.*

Garfinkel D. et al., Computer modeling identifies glucokinase as glucose sensor of pancreatic beta cells, American Journal Physiological, Vo. 247 (3Pt2) 1984, p. 527-536.

Grupe A. et al., Transgenic knockouts reveal a critical requirement for pancreatic beta cell glucokinase in maintaining glucose homeostasis, Cell, Vo. 83, 1995, p. 69-78.

Ferre T. et al., Correction of diabetic alterations by glucokinase, Proceedings of the National Academy of Sciences of the U.S.A., vol. 93, 1996, p. 7225-7230.

Vionette N. et al., Nonsense mutation in the glucokinase gene causes early-onset non-insulin-dependent diabetes mellitus, Nature Genetics, vol. 356, 1992, p. 721-722.

Glaser B. et al., Familial hyperinsulinism caused by an activating glucokinase mutation, New England Journal Medicine, vol. 338, 1998, p. 226-230.

Patent Abstracts of Japan for 64-025764 published on Jan. 27, 1989.

Ikemoto S. et al., High fat diet-induced hyperglycemia: Prevention by low level expression of a glucode transporter (GLUT4) minigene in transgenic mice, Proceedings of the National Academy of Science of the U.S.A., vol. 92, pp. 3096-3099.

International Search Report for PCT/JP03/03656 mailed on Jun. 17, 2003.

Patent Abstracts of Japan for 58-069812 published on Apr. 26, 1983.

Nobuo Izumiya et. al., Theory and Experiment in Peptide Synthesis, Maruzen, 1983, p. 119, line 5—p. 120, last line.

Comprehensive Organic Synthesis, Vo. 6, Pergamon Press, 1991.

T.W. Green, et. al., Protective Groups in Organic Synthesis, 2nd Edition, John Wiley & Sons, 1991.

* cited by examiner

AMINOBENZAMIDE DERIVATIVE

This application is a continuation of International Patent Application No. PCT/JP03/03656, filed Mar. 25, 2003, which was published in Japanese as International Publication No. WO 03/080585 on Oct. 2, 2003, and claims the benefit of priority of Japanese Patent Application No. JP 2002-085720, filed Mar. 26, 2002.

TECHNICAL FIELD

This invention relates to glucokinase activators containing aminobenzamide derivatives as active constituents, and to novel aminobenzamide derivatives or their salts.

BACKGROUND ART

Glucokinase (GK) (ATP:D-hexose 6-phosphotransferase, EC 2.7.1.1) is one of the four types of mammalian hexokinases (hexokinase IV). Hexokinases are enzymes in the first step of the glycolysis pathway which catalyze the reaction from glucose to glucose-6-phosphate. Expression of glucokinase is largely localized in the liver and pancreatic beta cells, and it plays an important role in glucose metabolism throughout the body by controlling the rate limiting step of glucose metabolism in these cells. The glucokinase types expressed in the liver and pancreatic beta cells differ in the sequence of the 15 N-terminal amino acids due to a difference in splicing, but their enzymatic properties are identical. The enzyme activities of the three hexokinases (I, II, III) other than glucokinase become saturated at a glucose concentration of below 1 mM, whereas the Km of glucokinase for glucose is 8 mM, or close to the physiological glucose level. Thus, glucokinase-mediated intracellular glucose metabolism is accelerated in response to glucose level changes by postprandial glucose level increase (10-15 mM) from normal glucose (5 mM).

The theory that glucokinase acts as a glucose sensor for pancreatic beta cells and the liver has been advocated for about 10 years. Recent results in glucokinase gene-manipulated mice have confirmed that glucokinase does in fact play an important role in systemic glucose homeostasis. Mice lacking a functional glucokinase gene die shortly after birth, while mice overexpressing glucokinase have lower blood glucose levels. With glucose level increase, the reactions of pancreatic beta cells and the liver, while differing, both act toward lowering blood glucose. Pancreatic beta cells secrete more insulin, while the liver takes up glucose and stores it as glycogen while also reducing glucose release.

Such variation in glucokinase enzyme activity is important for liver and pancreatic beta cell-mediated glucose homeostasis in mammals. A mutant form of the glucokinase gene is expressed in a type of diabetes which occurs in youth, known as MODY2 (maturity-onset diabetes of the young), and the reduced glucokinase activity has been shown to be responsible for blood glucose increase. On the other hand, families have been found having a mutation which increases glucokinase activity, and such individuals exhibit hypoglycemic symptoms.

This suggests that in humans as well, glucokinase functions as a glucose sensor and thus plays an important role in glucose homeostasis. Glucose regulation utilizing a glucokinase sensor system should be possible to achieve in type II diabetic patients. Since glucokinase activators should have effects of accelerating insulin secretion by pancreatic beta cells and of promoting glucose uptake and inhibiting glucose release by the liver, they are potentially useful as therapeutic agents for type II diabetic patients.

In recent years it has been demonstrated that pancreatic beta cell glucokinase is expressed locally in rat brain, and particularly in the ventromedial hypothalamus (VMH). Approximately 20% of VMH neurons are known as "glucose-responsive neurons", and these have long been considered to play an important role in body weight control. Administration of glucose into rat brain reduces feeding consumption, but inhibiting glucose metabolism by intracerebral administration of the glucose analog glucosamine produces hyperphagia. Electrophysiological experiments have indicated that glucose-responsive neurons are activated in response to physiological glucose level changes (5-20 mM) but that their activation is inhibited with glucose metabolism inhibition by glucosamine or the like.

The glucose level-detecting system in the VMH is believed to be based on a glucokinase-mediated mechanism similar to that for insulin secretion by pancreatic beta cells. Consequently, substances which activate glucokinase in the VMH in addition to the liver and pancreatic beta cells not only exhibit a blood glucose rectifying effect but can also potentially rectify obesity, which is a problem for most type II diabetic patients.

This indicates that compounds having glucokinase-activating effects are useful as therapeutic and/or prophylactic agents for diabetes, as therapeutic and/or prophylactic agents for diabetes complications such as retinopathy, nephropathy, neuropathy, ischemic heart disease, arteriosclerosis and the like, and as therapeutic and/or prophylactic agents for obesity.

An example of a compound which is structurally similar to the present invention is the compound represented by the formula (III) disclosed by International Publication No. WO00/26202.

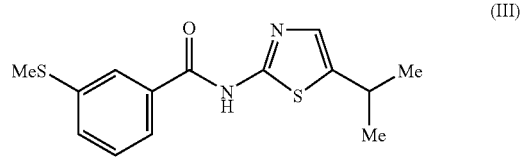

(III)

However, the aforesaid compound does not have an amino group in the benzamide skeleton, and is clearly different structurally from the compound of this application. Also, the compound in the aforesaid formula (III) is used as a CDK inhibitor and an anti-cancer agent, and in International Publication No. WO00/26202, there is no mention or suggestion regarding its use in diabetes mellitus.

The compound represented by the formula (IV) is disclosed by International Publication No. WO00/39118.

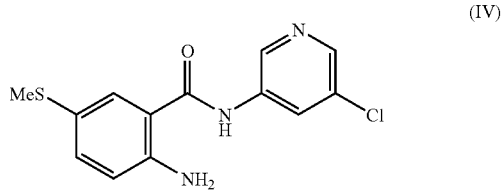

(IV)

This compound (IV) does not have a nitrogen atom adjacent to the carbon atom bonded to the nitrogen atom of the NH group of carbamoyl, and differs structurally from the compound of this application. The aforesaid compound (V) is used in relation to Factor Xa, but it is different from the diabetes mellitus which is the usage described in this application. Also, in WO00/No. 39118 wherein the compound (IV) is disclosed, there is no mention or suggestion to the effect that it is useful as a treatment or prevention agent for diabetes mellitus.

The compound represented by the formula (V) is disclosed by International Publication No. WO00/39118.

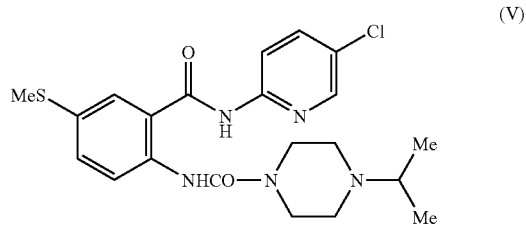

(V)

However, this compound (V) has a piperazinyl group on the carbonyl side of the amide, and clearly differs structurally from the compound of this application. These compounds are related to Factor Xa inhibitor. Also, their usage is clearly different from diabetes mellitus which is the usage for the compound of this application, and there is no suggestion in this report that these compounds are useful in diabetes mellitus.

The compound represented by the formula (VI) is disclosed by Japanese Patent Application Laid-Open No. 64-25764.

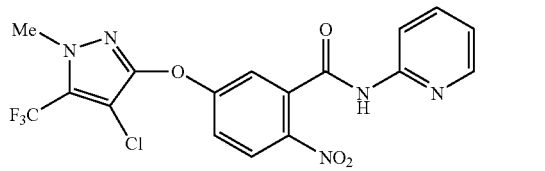

(VI)

However, this compound has a nitro group in the benzamide skeleton, and differs structurally from the compound of this application which has an amino group.

The compound represented by the formula (VII) is disclosed by WO01/No. 10865 as an example of a compound which is effective in the treatment of diabetes mellitus.

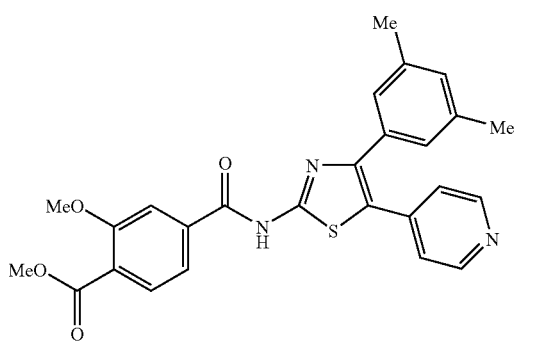

(VII)

However, since the compound shown in formula (VII) has a methoxy group in $R^1$ and does not have an amino group in the benzamide skeleton, it differs structurally from the compound of this application.

DISCLOSURE OF THE INVENTION

Figure 1:
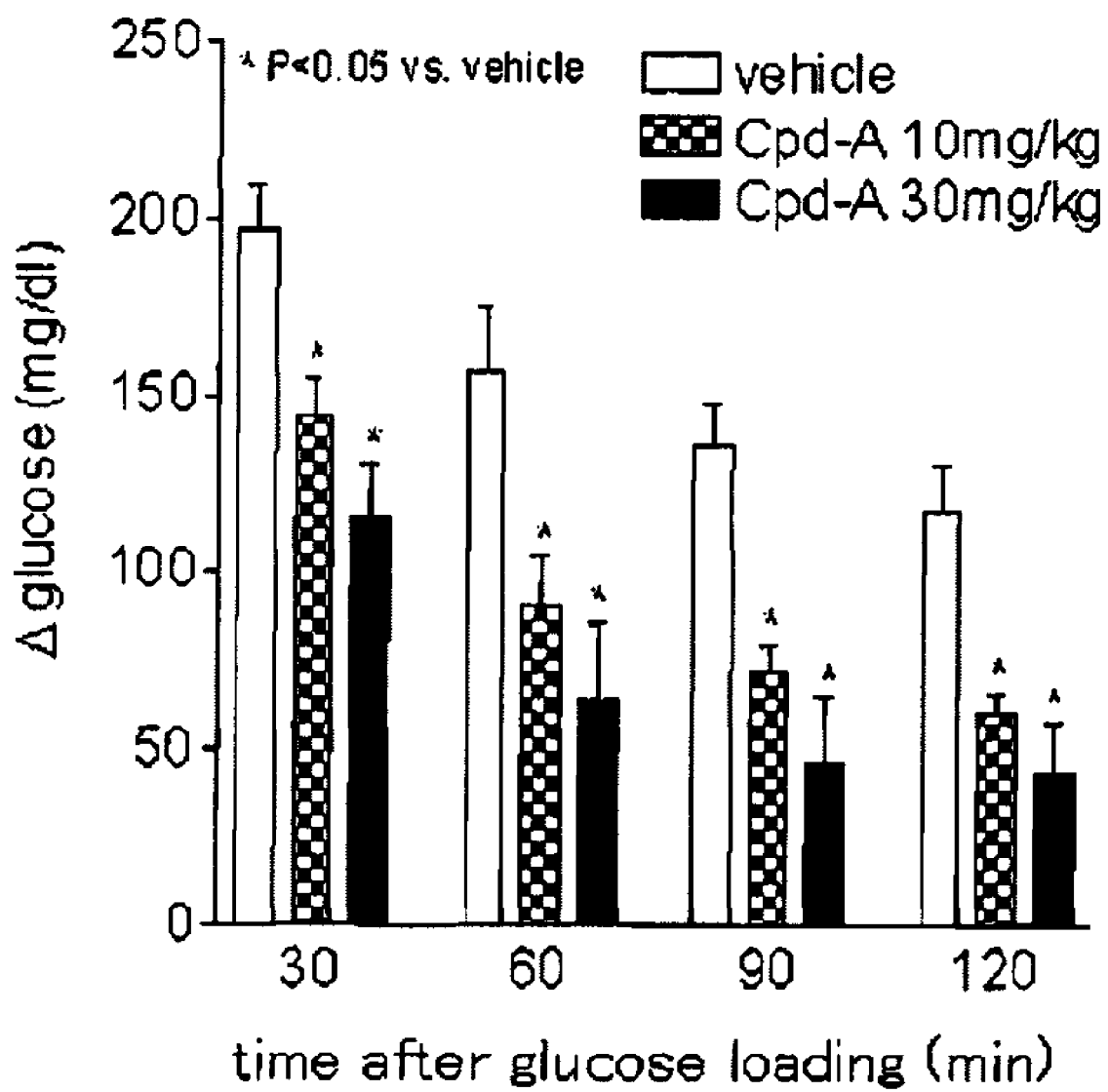
FIG. 1 is a bar graph showing the assay results of blood sugar levels of mice that were administered a control vehicle or the compound Cpd-A (namely, 2-amino-5-(4-methyl-4H-[1,2,4]triazol-3-ylsulfanyl)-N-(4-methylthiazol-2-yl)benzamide).

It is an object of this invention to provide a diabetic treatment and/or preventive agent which combines with glucokinase and increases the activity of glucokinase, and to provide an anti-obesity agent which, by activating glucokinase, stimulates the satiety center.

The advantages of the compound according to this invention are that it has a superior effect to that of existing antidiabetic agents, and permits the development of new drug effects which were not present in existing antidiabetic agents.

The Inventors carried out extensive studies to develop a novel antidiabetic agent which, due to a different mechanism of action from that of existing drugs, had a superior pharmacological action to that of existing antidiabetic agents, and new pharmacological effects. As a result, they discovered that the compound represented by formula (I) has a glucokinase activation effect, and thus arrived at the present invention. Specifically, this invention relates to the following:

(1) A compound represented by the formula (I):

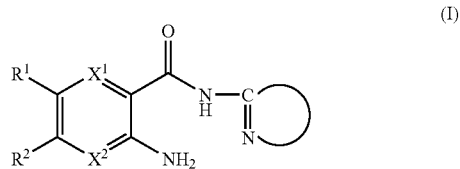

(I)

or a pharmaceutically acceptable salt thereof,
wherein
$R^1$ is —S(O)p-A, —S—(O)q-B or —O-D, wherein p and q, which are the same or different, each represent an integer from 0 to 2, A is a straight chain C1-C10 alkyl group which may be substituted by $R^{10}$, and B and D each independently represent $R^{12}$ which may be substituted by $R^{10}$;

$R^2$ is a hydrogen atom, a halogen atom, or a straight chain or branched C1-C6 alkyl group which may be substituted by $R^{10}$;

$X^1$ and $X^2$ each independently represent N or CH, but cannot both be N;

the formula (II):

(II)

shows a monocyclic or bicyclic heteroaryl group which has a nitrogen atom adjacent to the carbon atom bonded to the amide group, and the heteroaryl group may be substituted by $R^{10}$;

$R^{10}$ is $R^{11}$, or a hydrocarbon group which may be substituted by $R^{11}$;

$R^{11}$ is a hydrogen atom, amino, carbamoyl, carbamoylamino, carbamoyloxy, carboxyl, cyano, sulfamoyl, trifluoromethyl, a halogen atom, hydroxyl, formyl, straight chain C1-C6 alkyl, C3-C9 cyclic hydrocarbon, aralkyl, N-aralkylamino, N,N-diaralkylamino, aralkyloxy, aralkylcarbonyl, N-aralkylcarbamoyl, aryl, arylthio, N-arylamino, aryloxy, arylsulfonyl, arylsulfonyloxy, N-arylsulfonylamino, arylsulfamoyl, N-arylcarbamoyl, aroyl, aroxy, C2-C6 alkanoyl, N-C2-C6 alkanoylamino, C1-C6 alkylthio, N-C1-C6 alkylsulfamoyl, N,N-di-C1-C6 alkylsulfamoyl, C1-C6 alkylsulfinyl, C1-C6 alkylsulfonyl, N-C1-C6 alkylsulfonylamino, C1-C6 alkoxy, C1-C6 alkoxycarbonyl or C1-C6 alkylamino; and $R^{12}$ is phenyl, naphthyl, isoxazolyl, isothiazolyl, imidazolyl, oxazolyl, thiazolyl, thiadiazolyl, thienyl, triazolyl, tetrazolyl, pyridyl, pyrazinyl, pyrimidinyl, pyridazinyl, pyrazolyl, pyrrolyl, pyranyl, furyl, furazanyl, imidazolidinyl, tetrahydrofuranyl, piperazinyl, piperidinyl, pyrrolidinyl, morpholino, isoquinolyl, isoindolyl, indolyl, ethylene dioxyphenyl, methylene dioxyphenyl, quinolyl, pyridothiazolyl, dihydroindolyl, tetrahydroquinolinyl, tetrahydroisoquinolinyl, benzimidazolyl, benzoxazolyl, benzothiazolyl, benzotriazolyl or benzofuranyl.

(2) The compound according to (1),
wherein
$R^{10}$ in A is $R^{111}$, or a hydrocarbon group which may be substituted by $R^{111}$;

$R^{12}$ in B is a phenyl, isothiazolyl, imidazolyl, oxazolyl, thiazolyl, thiadiazolyl, thienyl, triazolyl, tetrazolyl, pyridyl, pyrimidinyl, furyl, ethylene dioxyphenyl, methylene dioxyphenyl, pyridothiazolyl, benzimidazolyl, benzothiazolyl or benzotriazolyl, and the foregoing functional groups may each be substituted by $R^{10}$;

$R^{10}$ in B is $R^{111}$, or a hydrocarbon group which may be substituted by $R^{111}$;

$R^{12}$ in D is a phenyl, naphthyl, pyridyl, pyrazinyl, pyrimidinyl, ethylene dioxyphenyl, methylene dioxyphenyl or quinolyl, and the foregoing functional groups may each be substituted by $R^{10}$;

$R^{10}$ in D is $R^{111}$, or a hydrocarbon group which may be substituted by $R^{111}$;

$R^{10}$ in $R^2$ is $R^{111}$, or a hydrocarbon group which may be substituted by $R^{111}$;

$R^{10}$ in the heteroaryl group represented by formula (II) is $R^{112}$, or a hydrocarbon group which may be substituted by $R^{112}$;

the heteroaryl group of formula (II) is thiazolyl, imidazolyl, isothiazolyl, 1,2,4-thiadiazolyl, 1,3,4-thiadiazolyl, triazolyl, oxazolyl, isoxazolyl, pyrazinyl, pyridyl, pyrimidinyl, pyridothiazolyl or benzothiazolyl;

$R^{111}$ is a hydrogen atom, carbamoyloxy, carboxyl, cyano, trifluoromethyl, a halogen atom, hydroxyl, straight chain C1-C6 alkyl, saturated C3-C9 cyclic hydrocarbon, aralkyl, aryl, arylthio, aroyl, aroxy, C1-C6 alkylthio, C1-C6 alkylsulfonyl, C1-C6 alkoxy or C1-C6 alkoxycarbonyl; and $R^{112}$ is a hydrogen atom, carbamoyl, carboxyl, sulfamoyl, trifluoromethyl, a halogen atom, hydroxyl, aralkyl, aryl, arylthio, arylsulfonyl, aroyl, aroxy, C1-C6 alkylthio, C1-C6 alkylsulfinyl, C1-C6 alkylsulfonyl, C1-C6 alkoxy, C1-C6 alkoxycarbonyl or C3-C6 cycloalkyloxy.

(3) The compound according to (1),
wherein
$R^{10}$ in A is $R^{113}$, or a hydrocarbon group which may be substituted by $R^{113}$;

$R^{12}$ in B is a phenyl, imidazolyl, oxazolyl, thiazolyl, thiadiazolyl, triazolyl, tetrazolyl, pyridyl, pyrimidinyl, ethylene dioxyphenyl, methylene dioxyphenyl or pyridothiazolyl, and the foregoing functional groups may each be substituted by $R^{10}$;

$R^{10}$ in B is $R^{113}$, or a hydrocarbon group which may be substituted by $R^{113}$;

$R^{12}$ in D is a phenyl, naphthyl, pyridyl, ethylene dioxyphenyl or methylene dioxyphenyl, and the foregoing functional groups may each be substituted by $R^{10}$;

$R^{10}$ in D is $R^{113}$, or a hydrocarbon group which may be substituted by $R^{113}$;

$R^{10}$ in $R^2$ is $R^{113}$, or a hydrocarbon group which may be substituted by $R^{113}$;

$R^{113}$ is a hydrogen atom, carboxyl, trifluoromethyl, a halogen atom, hydroxyl, straight chain C1-C6 alkyl, saturated C3-C9 cyclic hydrocarbon, C1-C6 alkoxy, C1-C6 alkoxycarbonyl, C1-C6 alkylthio or C1-C6 alkylsulfonyl;

$R^{10}$ in the heteroaryl group of formula (II) is $R^{112}$, or a hydrocarbon group which may be substituted by $R^{112}$; and the heteroaryl group of formula (II) is thiazolyl, imidazolyl, isothiazolyl, 1,2,4-thiadiazolyl, 1,3,4-thiadiazolyl, triazolyl, oxazolyl, isoxazolyl, pyrazinyl, pyridyl, pyrimidinyl, pyridothiazolyl or benzothiazolyl.

(4) The compound according to (1),
wherein
$R^{10}$ in A is $R^{113}$, or a hydrocarbon group which may be substituted by $R^{113}$;

$R^{12}$ in B is a phenyl, imidazolyl, oxazolyl, thiazolyl, thiadiazolyl, triazolyl, pyridyl, pyrimidinyl, ethylene dioxyphenyl, methylene dioxyphenyl or pyridothiazolyl, and the foregoing functional groups may each be substituted by $R^{10}$;

$R^{10}$ in B is $R^{113}$, or a hydrocarbon group which may be substituted by $R^{113}$;

$R^{12}$ in D is a phenyl, naphthyl, pyridyl, ethylene dioxyphenyl or methylene dioxyphenyl, and the foregoing functional groups may each be substituted by $R^{10}$;

$R^{10}$ in D is $R^{113}$, or a hydrocarbon group which may be substituted by $R^{113}$;

$R^{10}$ in $R^2$ is $R^{113}$, or a hydrocarbon group which may be substituted by $R^{113}$;

$R^{113}$ is a hydrogen atom, carboxyl, trifluoromethyl, a halogen atom, hydroxyl, straight chain C1-C6 alkyl, saturated C3-C9 cyclic hydrocarbon, C1-C6 alkoxy, C1-C6 alkoxycarbonyl, C1-C6 alkylthio or C1-C6 alkylsulfonyl;

$R^{10}$ in formula (II) is R, or a hydrocarbon group which may be substituted by $R^{114}$; and $R^{114}$ is a hydrogen atom, carboxyl, trifluoromethyl, a halogen atom, hydroxyl, aryl, arylthio, straight chain C1-C6 alkyl, C1-C6 alkylthio, C1-C6 alkoxy or C1-C6 alkoxycarbonyl.

(5) The compound according to (4), wherein $R^1$ in formula (I) is —S(O)p-A or —S—(O)q-B.

(6) The compound according to (4), wherein $R^1$ in formula (I) is —O-D.

(7) The compound according to (3), wherein both $X^1$ and $X^2$ in formula (I) are CH.

(8) The compound according to (3), wherein either $X^1$ or $X^2$ in formula (I) is a nitrogen atom.

(9) The compound according to (4), wherein both $X^1$ and $X^2$ in formula (I) are CH.

(10) The compound according to (4), wherein either $X^1$ or $X^2$ in formula (I) is a nitrogen atom.

(11) A glucokinase activator containing as an active constituent the compound according to any of (1) to (10).
(12) A treatment agent and/or preventive agent for diabetes mellitus containing as an active constituent the compound according to any of (1) to (10).
(13) A treatment agent and/or preventive agent for diabetes mellitus or obesity containing as an active constituent the compound according to any of (1) to (10).
(14) A treatment agent and/or preventive agent for obesity containing as an active constituent the compound according to any of (1) to (10).

The terms used in the present specification will now be described, while describing the invention in further detail.

An "aryl group" is, for example, a cyclic hydrocarbon aryl group having 6 to 14 carbon atoms such as phenyl, naphthyl, biphenylyl or anthryl group.

A "lower alkyl group" means a straight chain or branched alkyl group preferably having 1 to 6 carbon atoms. Examples are methyl, ethyl, propyl, isopropyl, butyl, isobutyl, sec-butyl, tert-butyl, pentyl, isoamyl, neopentyl, isopentyl, 1,1-dimethylpropyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,2,2-trimethylpropyl and 1-ethyl-2-methylpropyl.

A "cycloalkyl group" means a saturated monocyclic hydrocarbon group having 3 to 9 carbon atoms. Examples are cyclopropyl, cyclobutyl, cyclopentyl, cyclohexyl and cycloheptyl.

A "lower alkoxygroup" means a group wherein the hydrogen atom of a hydroxyl group is substituted by the aforesaid lower alkyl group. Examples are methoxy, ethoxy, propoxy, isopropoxy, butoxy, sec-butoxy, tert-butoxy, pentyloxy, isopentyloxy, hexyloxy and isohexyloxy.

An "aralkyl group" means a lower alkyl group containing the aforesaid aryl group. Examples are benzyl, 1-phenylethyl, 2-phenylethyl, 1-naphthylmethyl and 2-naphthylmethyl.

An "aralkylamino group" means a group wherein a hydrogen atom of an amino group is monosubstituted by the aforesaid aralkyl group. Examples are benzylamino and phenethylamino.

A "diaralkylamino group" means a group wherein hydrogen atoms of identical or different amino groups are disubstituted by the aforesaid aralkyl groups. Examples are dibenzylamino and N-benzyl-2-phenylethylamino.

An "aralkylcarbamoyl group" means a group wherein a hydrogen atom bonded to the nitrogen atom of a carbamoyl group is monosubstituted by the aforesaid aralkyl group. For example, benzylcarbamoyl and phenylethylcarbamoyl are preferred.

An "alkylsulfamoyl group" means a group wherein a hydrogen atom of $NH_2$ of the aforesaid alkylsulfamoyl group is monosubstituted by the aforesaid alkyl group. For example, methylsulfamoyl, ethylsulfamoyl and isopropylsulfamoyl are preferred.

A "dialkylsulfamoyl group" means a group wherein the hydrogen atoms of $NH_2$ of the aforesaid alkylsulfamoyl group are disubstituted by the aforesaid alkyl groups which are identical or different. Examples are dimethylsulfamoyl, diethylsulfamoyl and methylethylsulfamoyl.

A "heteroaryl group" means a 4- to 7-membered single ring wherein this heteroaryl group has 1 to 3 hetero atoms selected from the group consisting of oxygen, sulfur and nitrogen atom, or a double ring wherein the heteroaryl group of this single ring is condensed with a benzene ring or pyridine ring. Examples are furyl, thienyl, pyrrolyl, imidazolyl, pyrazolyl, thiazolyl, thiadiazolyl, isothiazolyl, oxazolyl, isoxazolyl, pyridyl, pyrimidinyl, pyrazinyl, quinolyl, isoquinolyl, quinazolinyl, quinolidinyl, quinoxalinyl, cinnolinyl, benzimidazolyl, imidazopyridyl, benzofuranyl, naphthylidinyl, 1,2-benzisoxazolyl, benzoxazolyl, benzothiazolyl, oxazolopyridyl, pyridothiazolyl, isothiazolopyridyl and benzothienyl.

A "halogen atom" means, for example, a fluorine atom, a chlorine atom, a bromine atom or an iodine atom.

A "lower alkylcarbamoyl group" means a carbamoyl group monosubstituted by the aforesaid lower alkyl group. Examples are methylcarbamoyl, ethylcarbamoyl, propylcarbamoyl, isopropylcarbamoyl, butylcarbamoyl, sec-butylcarbamoyl and tert-butylcarbamoyl.

A "di-lower alkylcarbamoyl group" means a carbamoyl disubstituted by the aforesaid lower alkyl groups which are identical or different. Examples of "di-lower alkyl carbamoyl group" are dimethylcarbamoyl, diethylcarbamoyl, ethylmethylcarbamoyl, dipropylcarbamoyl, methylpropylcarbamoyl and diisopropyl carbamoyl.

A "lower alkylamino group" means an amino group monosubstituted by the aforesaid lower alkyl group. Examples are methylamino, ethylamino, propylamino, isopropylamino, butylamino, sec-butylamino or tert-butylamino.

A "di-lower alkylamino group" means an amino group disubstituted by the aforesaid lower alkyl groups which are identical or different. Examples are dimethylamino, diethylamino, dipropylamino, methylpropylamino or diisopropylamino.

An "aralkylamino group" means a group wherein a hydrogen atom of an amino group is monosubstituted by the aforesaid aralkyl group. Examples are benzylamino, phenylethylamino and 2-phenylethylamino.

A "diaralkylamino group" means a group wherein hydrogen atoms of amino groups are disubstituted by the aforesaid aralkyl groups. Examples are dibenzylamino, diphenylethylamino and benzylphenyl ethylamino. These aralkyl groups may be identical or different.

An "aralkyloxy group" means a group wherein the aforesaid aralkyl group is bonded to an oxygen atom. Examples are benzyloxy, phenylethyloxy and 2-phenylethyloxy.

An "aralkylcarbonyl group" means a group wherein the aforesaid aralkyl group is bonded to a carbonyl group. Examples are benzylcarbonyl and phenylethylcarbonyl.

An "aralkylcarbamoyl group" means a group wherein a hydrogen atom of a carbamoyl group is monosubstituted by the aforesaid aralkyl group. Examples are benzylcarbamoyl, phenylethylcarbamoyl and 2-phenylethylcarbamoyl.

An "arylthio group" means a group wherein the hydrogen atom of a thiol group is substituted by the aforesaid aryl group. Examples are phenylthio, naphthylthio and biphenylthio.

An "arylamino group" means a group wherein a hydrogen atom of an amino group is monosubstituted by the aforesaid aryl group. Examples are phenylamino, naphthylamino and biphenylamino.

An "aryloxy group" means a group wherein the hydrogen atom of a hydroxyl group is substituted by the aforesaid aryl group. Examples are phenyloxy, naphthyloxy and biphenyloxy.

An "arylsulfonyl group" means a group wherein the aforesaid aryl group is bonded to a sulfonyl group. Examples are phenylsulfonyl and naphthylsulfonyl.

An "arylsulfonyloxy group" means a group wherein the hydrogen atom of a hydroxyl group is substituted by the aforesaid arylsulfonyl group. Examples are phenylsulfonyloxy and biphenylsulfonyloxy.

An "arylsulfonylamino group" means a group wherein a hydrogen atom of an amino group is monosubstituted by the aforesaid arylsulfonyl group. Examples are phenylsulfonylamino, naphthylsulfonylamino and biphenylsulfonylamino.

An "arylsulfamoyl group" means a group wherein a hydrogen atom of a sulfamoyl group is monosubstituted by an aryl group. Examples are phenylsulfamoyl, naphthylsulfamoyl and biphenylsulfamoyl.

An "arylcarbamoyl group" means a group wherein a hydrogen atom of a carbamoyl group is monosubstituted by an aryl group. Examples are phenylcarbamoyl, naphthylcarbamoyl and biphenylcarbamoyl.

An "aroyl group" means a group wherein the aforesaid aryl group is bonded to a carbonyl group. Examples are phenylcarbonyl and naphthylcarbonyl.

An "aroxy group" means a group which wherein the aforesaid aroyl group is bonded to an oxygen atom. Examples are phenylcarbonyloxy and naphthylcarbonyloxy.

An "alkanoyl group" means a group wherein the aforesaid alkyl group is bonded to a carbonyl group. Examples are methylcarbonyl, ethylcarbonyl, propylcarbonyl and isopropylcarbonyl.

An "alkanoylamino group" means a group wherein the aforesaid alkanoyl group is bonded to an amino group. Examples are methylcarbonylamino, ethylcarbonylamino and isopropylcarbonylamino.

An "alkylthio group" means a group wherein the aforesaid alkyl group is bonded to a sulfur atom. Examples are methylthio, ethylthio, propylthio and isopropylthio.

An "alkylsulfamoyl group" means a group wherein a hydrogen atom of a sulfamoyl group is monosubstituted by the aforesaid alkyl group. Examples are methylsulfamoyl, ethylsulfamoyl, propylsulfamoyl and isopropylsulfamoyl.

A "dialkylsulfamoyl group" means a group wherein the hydrogen atoms of a sulfamoyl group are disubstituted by the aforesaid alkyl groups. Examples are dimethylsulfamoyl, diethylsulfamoyl and methyl ethylsulfamoyl. These alkyl groups may be identical or different.

An "alkylsulfinyl group" means a group wherein the aforesaid alkyl group is bonded to a sulfinyl group. Examples are methylsulfinyl, ethylsulfinyl and isopropylsulfinyl.

An "alkylsulfonyl group" means a group wherein the aforesaid alkyl group is bonded to a sulfonyl group. Examples are methylsulfonyl, ethylsulfonyl, propylsulfonyl and isopropylsulfonyl.

An "alkylsulfonylamino group" means a group wherein a hydrogen atom of an amino group is monosubstituted by the aforesaid alkylsulfonyl group. Examples are methylsulfonylamino, ethylsulfonylamino, propylsulfonylamino and isopropylsulfonylamino.

An "alkoxycarbonyl group" means a group wherein the hydrogen atom of a carboxyl group is substituted by the aforesaid alkyl group. Examples are methoxycarbonyl, ethoxycarbonyl, propylcarbonyl and isopropylcarbonyl.

A "hydrocarbon group" is a straight chain alkyl group having 1 to 6 carbon atoms, wherein 1 or 2, but preferably 1, of the carbon atoms forming this straight chain alkyl group may be substituted by a nitrogen atom, sulfur atom or oxygen atom, and/or carbon atoms in the straight chain alkyl group having 1 to 6 carbon atoms are connected by double bonds or triple bonds. The number of these double bonds or triple bonds is preferably 1 or 2, but more preferably 1.

Specifically, this hydrocarbon group is preferably methyl, ethyl, propyl, isopropyl, butyl, or the groups represented by the following formulae (VIII):

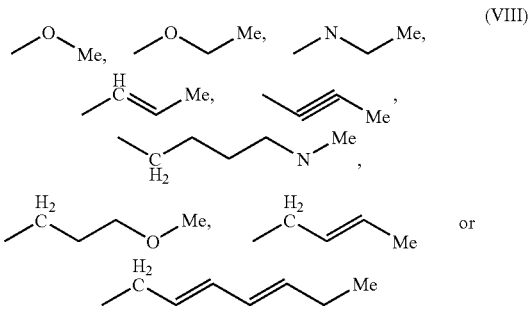

but more preferably methyl, ethyl, propyl, isopropyl, or the groups represented by the following formulae (IX):

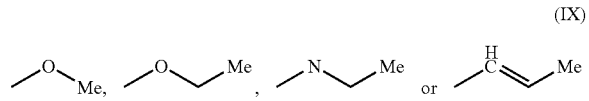

A "C3-C9 cyclic hydrocarbon group" means a group wherein the aforesaid hydrocarbon group which is a saturated or unsaturated hydrocarbon group having 3 to 9 carbon atoms forms a ring structure.

The C3-C9 cyclic hydrocarbon group is preferably a saturated cyclic hydrocarbon group having 3 to 9 carbon atoms.

More specifically, the C3-C9 cyclic hydrocarbon group is preferably cyclopropyl, cyclobutyl, cyclopentyl or cyclohexyl, but more preferably cyclopropyl, cyclobutyl or cyclopentyl.

To more specifically describe the aminobenzamide derivative according to this invention, the various symbols used in the aforesaid formula (I) will be described referring to specific examples.

$R^1$ is —S(O)p-A, —S(O)q-B or —O-D.

p and q are each an integer from 0 to 2.

p and q are each preferably 0 or 2, but more preferably 0.

A is a straight chain C1-C10 alkyl group which may be substituted by $R^{10}$.

The "straight chain C1-C10 alkyl group" of A is, for example, methyl, ethyl, propyl, butyl, pentyl or hexyl. Among these, methyl, ethyl, propyl or butyl is preferred, and methyl, ethyl or propyl is more preferred.

The straight chain C1-C10 alkyl group of A may be bonded to the hydrocarbon group of $R^{10}$ to form a ring preferably containing 3 to 7 members. The ring structure of A is, for example, preferably cyclopropyl, cyclobutyl, cyclopentyl, cyclohexyl or cycloheptyl.

A is, for example, methyl, ethyl, propyl, cyclopropyl, isopropyl, butyl, pentyl, cyclopentyl, cyclohexyl or cycloheptyl. Among these, methyl, ethyl, propyl, isopropyl, butyl, cyclopentyl or cyclohexyl are more preferred, and methyl, ethyl, propyl, isopropyl, cyclopentyl or cyclohexyl are more preferred.

$R^{10}$ is $R^{11}$, or a straight chain hydrocarbon group which may be substituted by $R^{11}$. $R^{11}$ is a hydrogen atom, amino, carbamoyl, carbamoylamino, carbamoyloxy, carboxyl, cyano, sulfamoyl, trifluoromethyl, a halogen atom, hydroxy, formyl, a C3-C9 cyclic hydrocarbon, aralkyl, N-aralkylamino, N,N-diaralkylamino, aralkyloxy, aralkylcarbonyl, N-aralkylcarbamoyl, aryl, arylthio, N-arylamino, aryloxy, arylsulfonyl, arylsulfonyloxy, N-arylsulfonylamino, arylsulfamoyl, N-arylcarbamoyl, aroyl, aroxy, C2-C6 alkanoyl, N-C2-C6 alkanoylamino, C1-C6 alkylthio, N-C1-C6 alkylsulfamoyl, N,N-di-C1-C6 alkylsulfamoyl, C1-C6 alkylsulfinyl, C1-C6 alkylsulfonyl, N-C1-C6 alkylsulfonyl amino, C1-C6 alkoxy, C1-C6 alkoxycarbonyl or C1-C6 alkylamino.

$R^{10}$ in A is preferably $R^{111}$, or a hydrocarbon group which may be substituted by $R^{111}$, but more preferably $R^{113}$, or a hydrocarbon group which may be substituted by $R^{113}$. Herein, $R^{111}$ is a hydrogen atom, straight chain C1-C6 alkyl, carbamoyloxy, carboxyl, cyano, trifluoromethyl, a halogen atom, hydroxy, a saturated C3-C9 cyclic hydrocarbon, aralkyl, aryl, aroyl, aroxy, C1-C6 alkylthio, C1-C6 alkoxy or C1-C6 alkoxycarbonyl. $R^{113}$ is a hydrogen atom, straight chain C1-C6 alkyl, carboxyl, trifluoro methyl, a halogen atom, hydroxy, saturated C3-C9 cyclic hydrocarbon, C1-C6 alkoxy or C1-C6 alkoxycarbonyl.

Therefore, A is preferably methyl, ethyl, propyl, isopropyl, cyclopentyl, cyclohexyl, carbamoyloxymethyl, carbamoyloxyethyl, cyanomethyl, cyanoethyl, cyanopropyl, hydroxyethyl, carboxylmethyl, carboxylethyl, 1,2dichloroethyl, 3-bromopropyl, 2-chloroethyl, cyclopropylmethyl, cyclopropylethyl, cyclopentylmethyl, cyclopropylethyl, phenethyl, benzyl, trifluoromethyl, phenacyl, ethylthiomethyl, naphthoylmethyl, methylthioethyl, propylthiomethyl, isopropylthioethyl, 2-methoxyethyl, 2-methoxy-1-methylethyl, isopropyloxyethyl, methoxycarbonylmethyl, ethoxycarbonylmethyl, 2-methylsulfonylethyl, or the groups represented by the formulae (X):

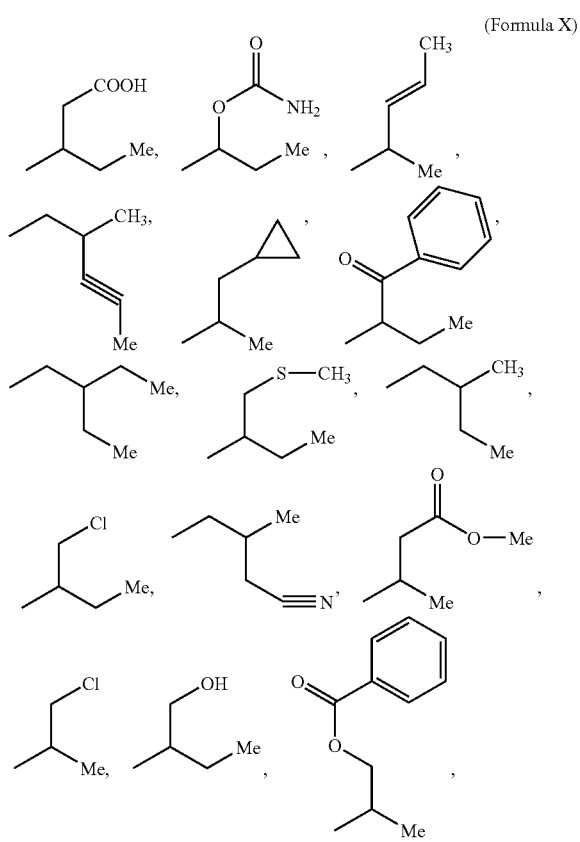

(Formula X)

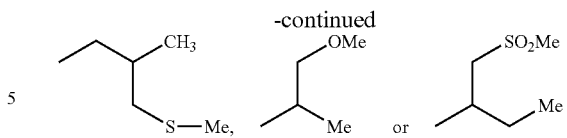

It is more preferably methyl, ethyl, isopropyl, cyclopentyl, cyclohexyl, cyanomethyl, 2-hydroxyethyl, cyclopropylmethyl, cyclopentylmethyl, trifluoromethyl, 2-methoxyethyl, or the groups represented by the formulae (XI):

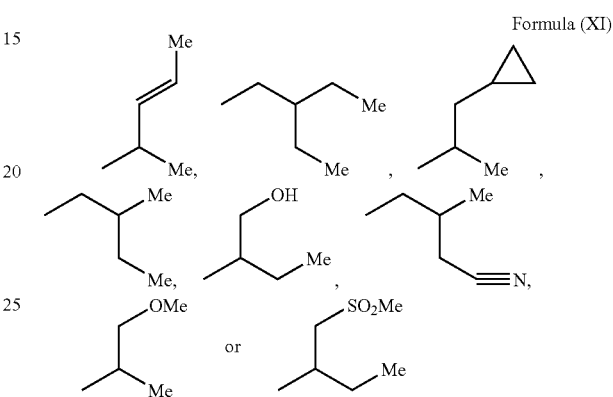

Formula (XI)

B is $R^{12}$ which may be substituted by $R^{10}$.

$R^{12}$ in B is, for example, phenyl, naphthyl, isoxazolyl, isothiazolyl, imidazolyl, oxazolyl, thiazolyl, thiadiazolyl, thienyl, triazolyl, tetrazolyl, pyridyl, pyrazinyl, pyrimidinyl, pyridazinyl, pyrazolyl, pyrrolyl, pyranyl, furyl, furazanyl, imidazolidinyl, tetrahydrofuranyl, piperazinyl, piperidinyl, pyrrolidinyl, morpholino, isoquinolyl, isoindolyl, indolyl, ethylene dioxyphenyl, quinolyl, pyridothiazolyl, dihydroindolyl, tetrahydroquinolinyl, tetrahydroisoquinolinyl, benzimidazolyl, benzoxazolyl, benzothiazolyl, benzotriazolyl, benzofuranyl or methylene dioxyphenyl.

$R^{12}$ in B is preferably phenyl, isothiazolyl, imidazolyl, oxazolyl, thiazolyl, thiadiazolyl, thienyl, triazolyl, tetrazolyl, pyridyl, pyrimidinyl, furyl, ethylene dioxyphenyl, methylene dioxyphenyl, benzimidazolyl, benzothiazolyl, benzotriazolyl or pyridothiazolyl, and the foregoing functional groups may each be substituted by $R^{10}$. It is more preferably phenyl, imidazolyl, oxazolyl, thiazolyl, thiadiazolyl, triazolyl, pyridyl, pyrimidinyl, ethylene dioxyphenyl, methylene dioxyphenyl or pyridothiazolyl, and the foregoing functional groups may each be substituted by $R^{10}$.

$R^{10}$ in B is preferably $R^{111}$, or a hydrocarbon group which may be substituted by $R^{111}$, but more preferably $R^{113}$, or a hydrocarbon group which may be substituted by $R^{113}$. Herein, $R^{111}$ and $R^{113}$ have identical definitions to $R^{111}$ and $R^{113}$ in A respectively.

B is preferably phenyl, 2-thiazolyl, 4-thiazolyl, 5-thiazolyl, 2-thiadiazolyl, 2-pyridyl, 3-pyridyl, 4-pyridyl, 2-imidazolyl, 2-pyrimidinyl, 4-pyrimidinyl, 5-pyrimidinyl, 4-isothiazolyl, 2-oxazolyl, 4-oxazolyl, 5-oxazolyl, 2-thienyl, 3-thienyl, 2-furyl, 3-furyl, triazol-3-yl, 5-tetrazolyl, 5-(1-methyl)tetrazolyl, 2,3-ethylene dioxyphenyl, 3,4-ethylene dioxyphenyl, 2,3-methylene dioxyphenyl, 3,4-methylene dioxyphenyl, benzimidazolyl, benzothiazolyl, 5-benzotriazolyl, 5-benzothiazolyl, 6-benzothiazolyl, 1,3-thiazolo-[5,4-b]pyridyl, 4-methyl-4H-[1,2,4]triazol-3-yl, 1-methyl-1H-imidazol-2-yl, 4,5-dimethyl-4H-[1,2,4]triazol-3-yl, 4-methyl-5-trifluoromethyl-4H-[1,2,4]triazol-3-yl, 5-methyl-1,2,4-triazol-3-yl, 5-tetrazolyl, 4-carbamoyloxymethylphenyl, 3-carbamoyloxymethylphenyl, 4-methoxycarbonylmethylphenyl, 4-cyanophenyl, 4-hydroxyphenyl, 3-carboxyphenyl, 4-trifluoromethylphenyl, 2-methylthiophenyl, 3-methylthiophenyl, 4-methylthiophenyl, 4-methoxyphenyl, 3-ethoxycarbonylphenyl, 2-methoxycarbonylphenyl, 4-methylsulfonylphenyl, 2-(4-carbamoyl)thiazolyl, 2-(4-carbamoyloxy)thiazolyl, 2-(5-cyano)thiazolyl, 2-(5-hydroxymethyl)thiazolyl, 2-(4-carboxy)thiazolyl, 2-(4-carboxy)thiazolyl, 2-(5-bromo)thiazolyl, 2-(4-ethylthio)thiazolyl, 2-(5-trifluoromethyl)thiazolyl, 2-(4-methoxymethyl)thiazolyl, 2-(4-methoxycarbonyl)thiazolyl, 2-(4-methylsulfonyl)thiazolyl, 2-(5-carbamoyl)thiadiazolyl, 2-(5-carbamoyloxy)thiadiazolyl, 2-(5-cyano)thiadiazolyl, 2-(5-hydroxy)thiadiazolyl, 2-(5-carboxy)thiadiazolyl, 2-(5-bromo)thiadiazolyl, 2-(5-methylthio)thiadiazolyl, 2-(5-trifluoromethyl)thiadiazolyl, 2-(5-methoxymethyl)thiadiazolyl, 2-(5-methoxycarbonyl)thiadiazolyl, 2-(5-methylsulfonyl)thiadiazolyl, 5-(3-carboxy)thiadiazolyl, 5-(3-hydroxymethyl)thiadiazolyl, 5-(3-carbamoyl)thiadiazolyl, 5-(3-trifluoromethyl)thiadiazolyl, 5-(3methylthio)thiadiazolyl, 5-(3-methoxymethyl)thiadiazolyl., 5-(3-methoxycarbonyl)thiadiazolyl, 5-(3-methylsulfonyl)thiadiazolyl, 2-(5-carbamoyloxy)triazolyl, 2-(5-cyano)triazolyl, 2-(5-hydroxymethyl) triazolyl, 2-(5-carboxy) triazolyl, 2-(5-trifluoromethyl)triazolyl, 2-(5-methylthio)triazolyl, 2-(5-methoxymethyl)triazolyl, 2-(5-methoxycarbonyl)triazolyl, 2-(5-methylsulfonyl)triazolyl, 2-(3-carbamoyl)pyridyl, 2-(3-carbamoyloxy)pyridyl, 2-(4-cyano)pyridyl, 2-(5-hydroxy)pyridyl, 2-(4-carboxy)pyridyl, 2-(5-trifluoromethyl)pyridyl, 2-(4-methylthio)pyridyl, 2-(5-methoxy)pyridyl, 2-(5-methoxycarbonyl)pyridyl, 2-(4-methylsulfonyl)pyridyl, 2-(6-carbamoyl)pyrimidinyl, 2-(5-carbamoyloxy)pyrimidinyl, 2-(5-cyano)pyrimidinyl, 2-(5-hydroxy)pyrimidinyl, 2-(5-carboxy)pyrimidinyl, 2-(5-trifluoromethyl)pyrimidinyl, 2-(5-ethylthiomethyl)pyrimidinyl, 2-(5-methoxy)pyrimidinyl, 2-(5-ethoxycarbonyl)pyrimidinyl, 2-(5-methylsulfonyl)pyrimidinyl, 2-(4-carboxymethyl)thiazolyl, 2-(5-carbamoyloxymethyl)thiazolyl, 2-(5-chloromethyl)thiazolyl, 2-(5-methoxycarbonylmethyl)thiazolyl, 3-(5-carboxymethyl)-1,2,4-triazol-3-yl, 5-carbamoyloxymethyl-1,2,4-triazol-3-yl, 5-methoxycarbonylmethyl-1,2,4-triazol-2-yl, 5-cyanomethyl-1,2,4-triazol-2-yl, 5-methylsulfonylmethyl-1,2,4-triazol-2-yl, 5-methylsulfanylmethyl-1,2,4-triazol-2-yl, 2-(5-carboxymethyl)thiadiazolyl, 2-(5-carbamoyloxymethyl)thiadiazolyl, 2-(5-cyanomethyl)thiadiazolyl, 2-(5-methoxycarbonylmethyl)thiadiazolyl, 2-(5-methylsulfonylmethyl)thiadiazolyl or 2-(5-methylsulfanylmethyl)thiadiazolyl. However, it is more preferably phenyl, 2-thiazolyl, 2-thiadiazolyl, 2-pyridyl, 2-pyrimidinyl, 4-pyrimidinyl, 5-pyrimidinyl, 3-triazolyl, 5-tetrazolyl, 2,3-methylene dioxyphenyl, 4-methylene dioxyphenyl, 1,3-thiazolo[5,4-b]pyridyl, 4-methyl-4H-[1,2,4]triazol-3-yl, 1-methyl-1H-imidazol-2-yl, 4,5-dimethyl-4H-[1,2,4]triazol-3-yl, 4-methyl-5-trifluoromethyl-4H-[1,2,4]triazol-3-yl, 5-methyl-1,2,4-triazol-3-yl, 4-cyanophenyl, 4-trifluoromethylphenyl, 2-methylthiophenyl, 3-methylthiophenyl, 4-methylthiophenyl, 4-methoxyphenyl, 2-methoxycarbonylphenyl, 4-methoxycarbonylmethylphenyl, 4-methylsulfonylphenyl, 2-(5-hydroxymethyl)thiazolyl, 2-(5-trifluoromethyl)thiazolyl, 2-(4-methoxymethyl)thiazolyl, 2-(5-cyano)thiazolyl, 2-(5-chloromethyl)thiazolyl, 2-(5-methoxycarbonyl)thiazolyl, 2-(5-hydroxy)thiadiazolyl, 2-(5-trifluoromethyl)thiadiazolyl, 2-(5methoxymethyl)thiadiazolyl, 2-(5-methoxycarbonylmethyl)thiadiazolyl, 5-(3-hydroxymethyl)thiadiazolyl, 5-(3-trifluoromethyl)thiadiazolyl, 5-(3-methoxymethyl)thiadiazolyl, 5-(3-methoxycarbonyl)thiadiazolyl, 2-(5-cyanomethyl)thiadiazolyl, 2-(5-methylsulfonylmethyl)thiadiazolyl, 2-(5-methylsulfanylmethyl)thiadiazolyl, 2-(5-cyano)triazolyl, 2-(5-hydroxymethyl)triazolyl, 2-(5-trifluoromethyl)triazolyl, 2-(5-methoxymethyl)triazolyl, 2-(5-methoxycarbonyl)triazolyl, 2-(5-methoxycarbonylmethyl)triazolyl, 2-(5-cyanomethyl)triazolyl, 2-(5-methylsulfonylmethyl)triazolyl, 2-(5-methylsulfanylmethyl)triazolyl, 2-(4-cyano)pyridyl, 2-(5-hydroxy)pyridyl, 2-(5-trifluoromethyl)pyridyl, 2-(5-methoxy)pyridyl, 2-(5-methoxycarbonyl)pyridyl, 2-(5-cyano)pyrimidinyl, 2-(5-hydroxy)pyrimidinyl, 2-(5-trifluoromethyl)pyrimidinyl or 2-(5-methoxy)pyrimidinyl.

D is $R^{12}$ which may be substituted by $R^{10}$. $R^{10}$ and $R^{12}$ are as previously defined.

$R^{12}$ in D is preferably phenyl, naphthyl, pyridyl, ethylene dioxyphenyl or methylene dioxyphenyl. It is more preferably phenyl, pyridyl, methylene dioxyphenyl or ethylene dioxyphenyl, and the foregoing functional groups may each be substituted by $R^{10}$.

$R^{10}$ in D is preferably $R^{111}$, or a hydrocarbon group which may be substituted by $R^{111}$, but more preferably $R^{113}$, or a hydrocarbon group which may be substituted by $R^{113}$ Herein, $R^{111}$ and $R^{113}$ are as previously defined.

$R^2$ is a hydrogen atom, a halogen atom, or a C1-C6 alkyl group which may be substituted by $R^{10}$. $R^{10}$ in $R^2$ is preferably $R^{111}$, or a hydrocarbon group which may be substituted by $R^{111}$, but more preferably $R^{113}$, or a hydrocarbon group which may be substituted by $R^{113}$. $R^{111}$ and $R^{113}$ are as previously defined.

Therefore, more specifically, D is preferably phenyl, 1-naphthyl, 2-naphthyl, 2-pyridyl, 3-pyridyl, 4-pyridyl, 3,4-ethylene dioxyphenyl, 2,3-ethylene dioxyphenyl, 2,3-methylene dioxyphenyl, 3,4-methylene dioxyphenyl, 4-tolyl, 3-carbamoylphenyl, 4-carbamoyloxyphenyl, 4-carboxyphenyl, 2-cyanophenyl, 4-trifluoromethylphenyl, 4-chlorophenyl, 2-fluorophenyl, 2,4-difluorophenyl, 3-bromophenyl, 4-hydroxyphenyl, 4-methylthiophenyl, 2-fluoro-4-methylsulfonylphenyl, 2-methoxy-4-fluorophenyl, 2-methoxyphenyl, 3-methoxyphenyl, 4-methoxycarbonylphenyl, 2-methylsulfonylphenyl, 4-fluoro-2-methylsulfonylphenyl, 3-methylsulfonylphenyl, 4-methylsulfonylphenyl, 2-(4-carbamoyl)pyridyl, 3-(5-trifluoromethyl)pyridyl, 3-(6-methoxycarbonyl)pyridyl, 3-carboxyphenyl, 3carbamoyloxymethylphenyl, 3-hydroxymethylphenyl, 4-cyanomethylphenyl, 4-methylthiomethylphenyl, 3-methylsulfonylmethylphenyl, 3-methoxycarbonylmethylphenyl, 2-(5-carboxy)pyridyl, 3-(5-cyanomethyl)pyridyl, 2-(5-methylthio)pyridyl, 2-(4-methoxymethyl)pyridyl or 3-(5-methylsulfonyl)pyridyl, but more preferably phenyl, 2-pyridyl, 4-pyridyl, 2,3-methylene dioxyphenyl, 3,4-methylene dioxyphenyl, 4-tolyl, 2-cyanophenyl, 4-trifluoromethylphenyl, 4-chlorophenyl, 2-fluorophenyl, 2,4-difluorophenyl, 4-methylthiophenyl, 2-fluoro-4-methylsulfonylphenyl, 2-methoxy-4-fluorophenyl, 2-methoxyphenyl, 3-methoxyphenyl, 2-methylsulfonylphenyl, 4-fluoro-2-methylsulfonylphenyl, 3-methylsulfonylphenyl, 4-methylsulfonylphenyl, 3-(5-trifluoromethyl)pyridyl, 3-(6-methoxycarbonyl)pyridyl, 3-hydroxymethylphenyl, 4-methylthiomethylphenyl, 3-methylsulfonylphenyl, 2-(4-methoxymethyl)pyridyl or 3-(5-methylsulfonyl)pyridyl.

The formula (II) is a monocyclic or bicyclic heteroaryl group which may be substituted by $R^{10}$ containing a nitrogen atom next to the carbon atom combined with the amide group.

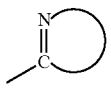
(II)

The monocyclic or bicyclic heteroaryl group of the aforesaid formula (II) is preferably, for example, 2-thiazolyl, 4-thiazolyl, 2-imidazolyl, 3-isothiazolyl, 1,2,4-thiadiazol-3-yl, 1,2,4-thiadiazol-5-yl, 1,3,4-thiadiazol-2-yl, 2-triazolyl, 2-oxazolyl, 3-isoxazolyl, pyrazinyl, 2-pyridyl, 2-pyrimidinyl, 3-pyrido-[3,2-d][1,3]thiazol-2-yl or 2-benzothiazolyl.

$R^{10}$ in the aforesaid formula (II) is preferably $R^{112}$, or a hydrocarbon group which may be substituted by $R^{112}$, but more preferably $R^{114}$, or a hydrocarbon group which may be substituted by $R^{114}$. Here, $R^{112}$ is, for example, a hydrogen atom, carbamoyl, carboxyl, sulfamoyl, trifluoromethyl, a halogen atom, hydroxy, aralkyl, aryl, arylthio, arylsulfonyl, aroyl, aroxy, straight chain C1-C6 alkyl, C1-C6 alkylthio, C1-C6 alkylsulfinyl, C1-C6 alkylsulfonyl, C1-C6 alkoxy, C1-C6 alkoxycarbonyl or C3-C6 cycloalkyloxy. $R^{114}$ is, for example, a hydrogen atom, carboxyl, trifluoromethyl, a halogen atom, hydroxy, aryl, arylthio, straight chain C1-C6 alkyl, C1-C6 alkylthio, C1-C6 alkoxy or C1-C6 alkoxycarbonyl.

Therefore, more specifically, a group represented by formula (II) is preferably, for example, 2-thiazolyl, 2-imidazolyl, 3-isothiazolyl, 1,3,4-thiadiazol-2-yl, 1,2,4-thiadiazol-5-yl, 2-oxazolyl, isoxazol-3-yl, 2-pyridyl, 2-pyrazinyl, 2-pyrimidinyl, 2-benzothiazolyl, 2-(4-carbamoyl)thiazolyl, 2-(4-carbamoyloxy)thiazolyl, 2-(5-cyano)thiazolyl, 2-(4-hydroxymethyl)thiazolyl, 2-(5-hydroxymethyl)thiazolyl, 2-(4-carboxy)thiazolyl, 2-(5-bromo)thiazolyl, 2-(5-chloro)thiazolyl, 2-(5-chloro-4-methyl)thiazolyl, 4-(1-methoxyethyl)thiazol-2-yl, 2-(4-methoxymethyl)thiazolyl, 2-(4-trifluoromethyl)thiazolyl, 2-(4-isopropyl)thiazolyl, 2-(4-methyl)thiazolyl, 4-(1-hydroxyethyl)thiazol-2-yl, 2-(4-ethylthio)thiazolyl, 2-(5-trifluoromethyl)thiazolyl, 2-(4-methoxymethyl)thiazolyl, 2-(4-methoxycarbonyl)thiazolyl, 2-(4-methylsulfonyl)thiazolyl, 4-(4-methyl-4H-[1,2,4]triazol-2-ylsulfanylmethyl)thiazol-2-yl, 4-(5-methyl-4H-[1,2,4]-triazol-2-ylsulfanylmethyl)thiazol-2-yl, 2-(5-carbamoyl)thiadiazolyl, 2-(5-carbamoyloxy)thiadiazolyl, 2-(5-cyano)thiadiazolyl, 2-(5-hydroxymethyl)thiadiazolyl, 2-(5-carboxy)thiadiazolyl, 2-(5-bromo)thiadiazolyl, 2-(5-methylthio)thiadiazolyl, 2-(5-trifluoromethyl)thiadiazolyl, 2-(5-methoxymethyl)thiadiazolyl, 2-(5-methoxycarbonyl)thiadiazolyl, 2-(5-methylsulfonyl)thiadiazolyl, 5-(3-carboxy)thiadiazolyl, 5-(3-hydroxymethyl)thiadiazolyl, 5-(3-carbamoyl)thiadiazolyl, 5-(3-trifluoromethyl)thiadiazolyl, 5-(3methylthio)thiadiazolyl, 5-(3-methoxymethyl)thiadiazolyl, 5-(3-methoxycarbonyl)thiadiazolyl, 5-(3-methylsulfonyl)thiadiazolyl, 2-(4-carbamoyl)pyridyl, 2-(4-carbamoyloxy)pyridyl, 2-(5-cyano)pyridyl, 2-(5-hydroxymethyl)pyridyl, 2-(4-carboxy)pyridyl, 2-(5-bromo)pyridyl, 2-(4-ethylthio)pyridyl, 2-(5-trifluoromethyl)pyridyl, 2-(4-methoxy)pyridyl, 2-(4-methoxymethyl)pyridyl, 2-(4-methoxycarbonyl)pyridyl, 2-(4-methylsulfonyl)pyridyl, 3-pyrido-[3,2-d][1,3]thiazol-2-yl, 2-(5-carbamoyl)thiadiazolyl, 2-(5-carbamoyloxy) thiadiazolyl, 2-(5-cyano) thiadiazolyl, 4-(6-carbamoyl)pyrimidinyl, 4-(6-carbamoyloxy)pyrimidinyl, 4-(6-cyano)pyrimidinyl, 4-(6-hydroxymethyl)pyrimidinyl, 4-(5-carboxy)pyrimidinyl, 4-(5-trifluoromethyl)pyrimidinyl, 4-(5-ethylthiomethyl)pyrimidinyl, 4-(5-methoxymethyl)pyrimidinyl, 4-(5-ethoxycarbonyl)pyrimidinyl, 4-(5-methylsulfonyl)pyrimidinyl, 2-(5-chloromethyl)thiazolyl, 2-(5-methoxycarbonylmethyl)thiazolyl, 2-(4-carboxylmethylmethyl)thiazolyl, 2-(5-carbamoyloxymethyl)thiazolyl, 3-(5-methoxymethyl)triazolyl, 3-(5-methoxycarbonylmethyl)triazolyl, 5-methylsulfonylmethyl-1,3,4-thiadiazol-2-yl, 5methylthiomethyl-1,3,4-thiadiazol-2-yl, 5-carboxymethyl-1,3,4-thiadiazol-2-yl, 5-carbamoyloxymethyl-1,3,4-thiadiazol-2-yl, 5-cyanomethyl-1,3,4-thiadiazol-2-yl, 5-methoxycarbonylmethyl-1,3,4-thiadiazol-2-yl, 5-hydroxymethyl-1,3,4-thiadiazol-2-yl or 5-methoxymethyl-1,3,4-thiadiazol-2-yl, but more preferably 2-thiazolyl, 3-isothiazolyl, 1,3,4-thiadiazol-2-yl, 1,2,4-thiadiazol-5-yl, 2-pyridyl, 2-(4-carbamoyloxy)thiazolyl, 2-(5-cyano)thiazolyl, 2-(5-hydroxymethyl)thiazolyl, 2-(4-carboxy)thiazolyl, 2-(5-bromo)thiazolyl, 2-(5-trifluoromethyl)thiazolyl, 2-(4-methoxymethyl)thiazolyl, 2-(4-methoxycarbonyl)thiazolyl, 2-(4-methylsulfonyl)thiazolyl, 2-(5-cyano)thiadiazolyl, 2-(5-methylthio)thiadiazolyl, 2-(5-methoxycarbonyl)thiadiazolyl, 2-(5-methylsulfonyl)thiadiazolyl, 5-(3-hydroxymethyl)thiadiazolyl, 5-(3-methoxymethyl)thiadiazolyl, 5-(3-methoxycarbonyl)thiadiazolyl, 2-(4-carbamoyloxy)pyridyl, 2-(5-cyano)pyridyl, 2-(5-hydroxymethyl)pyridyl, 2-(5-bromo)pyridyl, 2-(5-trifluoromethyl)pyridyl, 2-(4-methoxy)pyridyl, 2-(4-methoxymethyl)pyridyl, 2-(4-methoxycarbonyl)pyridyl, 3-pyrido-[3,2-d][1,3]thiazol-2-yl, 4-(6-cyano)pyrimidinyl, 4-(6-hydroxymethyl)pyrimidinyl, 4-(5trifluoromethyl)pyrimidinyl, 4-(5-methoxymethyl)pyrimidinyl, 2-(5-chloromethyl)thiazolyl, 2-(5-methoxycarbonylmethyl)thiazolyl, 5-methylsulfonylmethyl-1,3,4-thiadiazol-2-yl, 5-methylthiomethyl-1,3,4-thiadiazol-2-yl or 5-methoxycarbonylmethyl-1,3,4-thiadiazol-2-yl.

$R^2$ is a hydrogen atom, a halogen atom, or a C1-C6 alkyl group which may be substituted by $R^{10}$. $R^{10}$ in $R^2$ is preferably $R^{111}$, or a hydrocarbon group which may be substituted by $R^{111}$, but more preferably $R^{113}$, or a hydrocarbon group which may be substituted by $R^{113}$. $R^{111}$ and $R^{113}$ are as previously defined.

$R^2$ is more preferably methyl, ethyl, propyl, isopropyl, a fluorine atom or a hydrogen atom.

Preferably, $X^1$ and $X^2$ of a group represented by the following formula (XII) in formula (I) are both CH, or $X^1$ is a nitrogen atom and $X^2$ is CH, but more preferably, $X^1$ and $X^2$ are both CH.

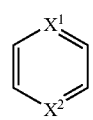
(XII)

[The Symbols in the Formula are as Previously Defined]

$R^1$ is —S—(O)p-A, —S(O)q-B or —O-D. Among these, —S(O)p-B or —O-D is preferred.

$R^2$ is a hydrogen atom, a halogen atom, or a C1-C10 alkyl group which may be substituted by $R^{10}$. Among these, a hydrogen atom or a halogen atom is preferred, and a hydrogen atom is more preferred.

The C1-C10 alkyl group of $R^2$ is preferably a C1-C6 alkyl group.

The halogen atom of $R^2$ is preferably a fluorine atom, a chlorine atom or a bromine atom, but more preferably a fluorine atom or a chlorine atom.

The benzamide derivative represented by the formula (I) according to this invention is, for example, 2-amino-4-fluoro-5-(1-methyl-1H-imidazol-2-ylsulfanyl-N-thiazol-2-yl)benzamide, 2-amino-4-fluoro-5-(1-methyl-1H-imidazol-2-ylsulfanyl)-N-(4-methylthiazol-2-yl)benzamide, 2-amino-5-(1-methyl-1H-imidazol-2-ylsulfanyl)-N-(4-hydroxymethylthiazol-2-yl)benzamide, 2-amino-5-(1H-imidazol-2-ylsulfanyl)-N-(4-hydroxymethylthiazol-2-yl)benzamide, 2-amino-5-methylsulfanyl-N-thiazolo[5,4-b]pyridin-2-ylbenzamide, 2-amino-5-(4-methyl-4H-[1,2,4]triazol-3-ylsulfanyl)-N-(4-methylthiazol-2-yl)benzamide, 2-amino-5-(4H-[1,2,4]triazol-3-ylsulfanyl)-N-(4-methylthiazol-2-yl)benzamide, 2-amino-5-(5-methyl-4H-[1,2,4]triazol-3-ylsulfanyl)-N-[4-(1-methyl-1H-imidazol-2-ylsulfanylmethyl)thiazol-2-yl]benzamide, 2-amino-4-fluoro-5-(4-methyl-4H-[1,2,4]triazol-3-ylsulfanyl)-N-(4-methylthiazol-2-yl)benzamide, 2-amino-4-fluoro-5(4,5-dimethyl-4H-[1,2,4]triazol-3-ylsulfanyl)-N-(4-methylthiazol-2-yl)benzamide, 2-amino-5-(2,5-dimethyl-2H-[1,2,4]triazol-3-ylsulfanyl)-N-(4-methylthiazol-2-yl)benzamide, 2-amino-4-fluoro-5-(4-methyl-4H-[1,2,4]triazol-3-ylsulfanyl)-N-(4-hydroxymethylthiazol-2-yl)benzamide, 2-amino-5-(4-methyl-4H-[1,2,4]triazol-3-ylsulfanyl)-N-(2-methylthiazol-4-yl)benzamide, 2-amino-5-(4-methyl-4H-[1,2,4]triazol-3-ylsulfanyl)-N-(4-methoxymethylthiazol-2-yl)benzamide, 2-amino-5-(4,5-dimethyl-4H-[1,2,4]triazol-3-ylsulfanyl)-N-(2-methylthiazol-4-yl)benzamide, 2-amino-4-fluoro-5-(4-methyl-4H-[1,2,4]triazol-3-ylsulfanyl)-N-(2-methylthiazol-4-yl)benzamide, 2-amino-5-(1-methyl-1H-imidazol-2-ylsulfanyl)-N-(4-methylthiazol-2-yl)benzamide, 2-amino-5-(4-methyl-4H-[1,2,4]triazol-3-ylsulfanyl)-N-thiazolo[5,4-b]pyridin-2-ylbenzamide, 2-amino-5-(1-methyl-1H-imidazol-2-ylsulfanyl)-N-thiazolo[5,4-b]pyridin-2-ylbenzamide, 2-amino-4-fluoro-5-(4-methyl-4H-[1,2,4]triazol-3-ylsulfanyl)-N-thiazolo[5,4-b]pyridin-2-ylbenzamide, 2-amino-5-(4,5-dimethyl-4H-[1,2,4]triazol-3-ylsulfanyl)-N-(4-methoxymethylthiazol-2-yl)benzamide, 2-amino-4-fluoro-5-(4,5-dimethyl-4H-[1,2,4]triazol-3-ylsulfanyl)-N-(4-methoxymethylthiazol-2-yl)benzamide, 2-amino-4-fluoro-5-(4,5-dimethyl-4H-[1,2,4]triazol-3-ylsulfanyl)-N-(4-methoxymethylthiazol-2-yl)benzamide, 2-amino-5(thiazol-2-ylsulfanyl)-N-(4-methoxymethylthiazol-2-yl)benzamide, 2-amino-5-phenoxy-N-(4-methoxymethylthiazol-2-yl)benzamide, 2-amino-5-phenoxy-N-[4-(4-methyl-4H-[1,2,4]triazol-2-ylsulfanylmethyl)thiazol-2-yl]benzamide, 2-amino-5-(4-fluoro-2-methylsulfonylphenoxy)-N-(4-methylthiazol-2-yl)benzamide, 2-amino-5-(2-methylsulfonylphenoxy)-N-(2-methylthiazol-4-yl)benzamide or 2-amino-3-phenoxy-5-(2-methylsulfonylphenoxy)-N-(4-methylthiazol-2-yl)benzamide.

The benzamide derivative according to this invention can exist as a pharmaceutically acceptable salt. The salt concerned may be an acid addition salt or a base addition salt.

The acid addition salt is, for example, a hydrohalide salt such as a hydrochloride, hydrofluoride, hydrobromide or hydroiodide; an inorganic acid salt such as a nitrate, perchlorate, sulfate, phosphate or carbonate; a lower alkyl sulfonate such as a methanesulfonate, trifluoromethanesulfonate or ethanesulfonate; an arylsulfonate such as a benzenesulfonate or p-toluenesulfonate; an organic acid salt such as a fumarate, succinate, citrate, tartrate, oxalate or maleate; or an amino acid salt such as a glutamate or aspartate.

The base addition salt is, for example, an alkali metal salt of sodium or potassium, an alkaline earth metal salt of calcium or magnesium, an ammonium salt, or a salt of an organic base such as guanidine, triethylamine or dicyclohexylamine.

The compound of this invention may exist as a solvate, preferably a hydrate, of a free compound or its salt.

The compound according to this invention may contain a stereoisomer such as an optical isomer, a diastereomer or a geometric isomer, or a tautomer, depending on the type of substituent. It will be understood that all of these isomers are included in the compound according to this invention. It will further be understood that arbitrary mixtures of these isomers are also included in the compound according to this invention.

Since the compound of this invention has a glucokinase activation effect, it is useful as a therapeutic and/or prophylactic agent for diabetes, and as a prophylactic agent for complications of diabetes.

Herein, diabetic complications are illnesses occurring together with the symptoms of diabetes mellitus. Complications of diabetes mellitus include diabetic nephropathy, diabetic retinopathy, diabetic neuropathy and diabetic arteriosclerosis.

The compound according to this invention can be used both for IDDM (insulin-dependent diabetes mellitus) and NIDDM (non-insulin-dependent diabetes mellitus).

IDDM (insulin-dependent diabetes mellitus) results when insulin resistance due to obesity is added to a hereditary loss of insulin secretion and insulin resistance in skeletal muscle, and is considered to be mainly an adult disease. Insulin-dependent diabetes mellitus is classified as Type I or Type II depending on the factors.

The compound of this invention is considered to be useful not only in Type I insulin-dependent diabetes mellitus, but also in Type II diabetes mellitus wherein a sufficient fall of blood sugar level was impossible to attain with prior art antidiabetic agents.

In Type II diabetes mellitus, it is remarkable that hyperglycemia continues for a long time after taking food as compared with a healthy person, but the compound according to this invention is useful also in this Type II diabetes mellitus.

The method of manufacturing the compound of this invention will now be described.

The compound (I) of this invention can be easily manufactured according to reaction means known in the art, or by methods themselves known in the art. The compound having the general formula (I) of this invention can be manufactured not only by synthesis in the usual liquid phase, but also by a synthetic step using the solid phase, such as a combinatorial synthetic step or a parallel synthetic step, which has made remarkable progress in recent years. It is preferably manufactured by, for example, the following steps:

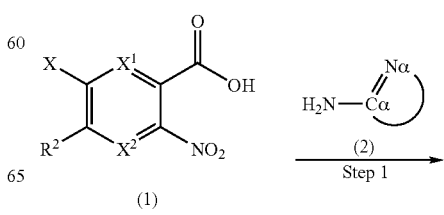

19

-continued

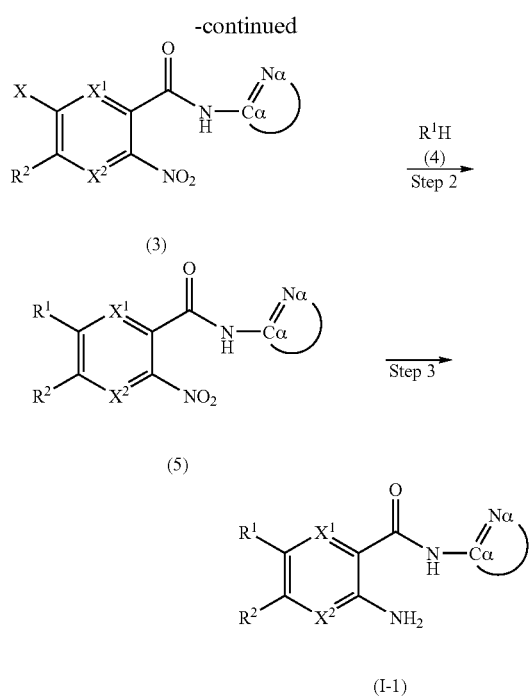

(3)

(5)

(I-1)

[The Symbols in the Formulae are as Previously Defined]

(Step 1)

This step is a method of reacting the carboxylic acid compound (1) or its reactant derivative with amino compound containing a monocyclic or bicyclic heteroaryl group which may be substituted by $R^{10}$ represented by the aforesaid formula (II), or its salt, to manufacture the compound (3). This reaction may be carried out by the usual amide-forming reaction, using the method described in the literature (e.g., Theory and Experiment in Peptide Synthesis, Nobuo Izumiya et al, Maruzen, 1983; and Comprehensive Organic Synthesis, Vol. 6, Pergamon Press, 1991), a corresponding method, or a combination of these with the usual methods, i.e., using a condensation agent known in the art, or the ester activation method, the mixed anhydride method, the acid chloride method or the carbodiimide method, which can be used by those skilled in the art. The amide-forming reagent is, for example, thionyl chloride, N,N-dicyclohexylcarbodiimide, 1-methyl-2-bromopyridinium iodide, N,N'-carbonyldiimidazole, diphenylphosphoryl chloride, diphenylphosphoryl azide, N,N'-disuccinimidyl carbonate, N,N'-disuccinimidyl oxalate, 1-ethyl-3-(3-dimethylaminopropyl)carbodiimide hydrochloride, ethyl chloroformate, isobutyl chloroformate or benzotriazol-1-yloxytris(dimethylamino)phosphonium hexafluorophosphate. Among these, thionyl chloride, N,N-dicyclohexylcarbodiimide and benzotriazol-1-yloxytris(dimethylamino)phosphonium hexafluorophosphate are preferred. In the amide forming reaction, a base or a condensation additive may be used together with the aforesaid amide forming reagent.

The base used is, for example, a tertiary aliphatic amine such as trimethylamine, triethylamine, N,N-diisopropylethylamine, N-methylmorpholine, N-methylpyrrolidine, N-methylpiperidine, N,N-dimethylaniline, 1,8-diazabicyclo [5.4.0]undeca-7-ene (DBU) or 1,5-azabicyclo[4.3.0]nona-5-ene (DBN); or an aromatic amine such as pyridine, 4-dimethylaminopyridine, picoline, lutidine, quinoline or isoquinoline. Among these, tertiary aliphatic amines are preferred, and triethylamine or N,N-diisopropylethylamine is particularly preferred.

The condensation additive used is, for example, N-hydroxybenzotriazole hydrate, N-hydroxysuccinimide, N-hydroxy-5-norbornene-2,3-dicarboxyimide or 3-hydroxy-3,4-dihydro-4-oxo-1,2,3-benzotriazole. Among these, N-hydroxybenzotriazole is particularly preferred.

The amount of the amino compound (2) used varies with the compounds used, the solvent and other reaction conditions, but it is usually 0.02 to 50 equivalents, and preferably 0.2 to 2 equivalents, relative to 1 equivalent of the carboxylic acid compound (1) or its reactive derivative. Herein, the reactive derivative is, for example, an active ester derivative or active amide derivative usually used in the field of organic chemistry.

The amount of the amide-forming reagent used varies with the compounds used, the solvent and other reaction conditions, but it is usually 1 to 50 equivalents, and preferably 1 to 5 equivalents, relative to 1 equivalent of the carboxylic acid compound (1) or its reactive derivative.

The amount of the condensation additive used varies with the compounds used, the solvent and other reaction conditions, but it is usually 1 to 50 equivalents, and preferably 1 to 5 equivalents, relative to 1 equivalent of the carboxylic acid compound (1) or its reactive derivative.

The amount of the base used varies with the compounds used, the solvent and other reaction conditions, but it is usually 1 to 50 equivalents, and preferably 3 to 5 equivalents.

The reaction solvent used in this step is, for example, an inert organic solvent and it is not particularly limited provided that it does not interfere with the reaction. Specific examples are methylene chloride, chloroform, 1,2-dichloroethane, trichloroethane, N,N-dimethylformamide, ethyl acetate, methyl acetate, acetonitrile, benzene, xylene, toluene, 1,4-dioxane, tetrahydrofuran, dimethoxyethane and a mixture of these solvents, but from the viewpoint of maintaining a suitable reaction temperature, methylene chloride, chloroform, 1,2-dichloroethane, acetonitrile, and N,N-dimethylformamide are particularly preferred.

The reaction temperature is −100° C. to the boiling point of the solvent, but preferably 0° C. to 30° C.

The reaction time is 0.5 to 96 hours, but preferably 3 to 24 hours.

The base, amide-forming reagent and condensation additive used in this step may each be of one kind, or a mixture of more than one kind.

If the compound (3) has a protecting group, this protecting group can be removed as required. The auxiliary group concerned can be removed by the method described in the literature (Protective Groups in Organic Synthesis, T. W. Green, 2nd edition, John Wiley & Sons, 1991), a corresponding method, or a combination thereof with an ordinary method.

The compound (3) thus obtained can be isolated and purified by a method known in the art, for example, concentration, concentration under reduced pressure, crystallization, solvent extraction, reprecipitation or chromatography, or it may not be isolated and purified, before proceeding to the next step.

(Step 2)

This step is a method of manufacturing the compound (5) by reacting the amide compound (3) obtained in the aforesaid Step 1 together with a compound (4).

In this reaction, a base may be added to the reaction system as required.

The compound (4) used is preferably a phenol derivative or a thiol derivative. The phenol derivative or thiol derivative is, for example, phenol, thiophenol, thioimidazole or thiotriazole.

The amount of the compound (4) used varies with the compounds used, the solvent and other reaction conditions, but it is usually 2 to 50 equivalents, and preferably 2 to 5 equivalents, relative to 1 equivalent of the amino derivative (3).

The base used may be a tertiary aliphatic amine such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undeca-7-ene (DBU) or 1,5-azabicyclo[4.3.0]nona-5-ene (DBN); an aromatic amine such as pyridine, 4-dimethylaminopyridine, picoline, lutidine, quinoline or isoquinoline; an alkali metal such as metallic potassium, metallic sodium or metallic lithium; an alkali metal hydride such as sodium hydride or potassium hydride; an alkyl derivative of an alkali metal such as butyllithium; an alkali metal alkoxide such as potassium tert-butyrate, sodium ethylate or sodium methylate; an alkali metal hydroxide such as potassium hydroxide or sodium hydroxide; or an alkali metal carbonate such as potassium carbonate. Among these, tertiary aliphatic amines, alkali metal hydrides or alkali metal carbonates are preferred, and triethylamine, N,N-diisopropylethylamine, sodium hydride or potassium carbonate is particularly preferred.

The amount of the base used varies with the compounds used, the solvent and other reaction conditions, but it is usually 0 to 50 equivalents, and preferably 2 to 10 equivalents, relative to 1 equivalent of the amide compound (3). One, two or more kinds of bases may be used if required.

The inert organic solvent used is not particularly limited provided that it does not interfere with the reaction, but specific examples are methylene chloride, chloroform, 1,2-dichloroethane, trichloroethane, N,N-dimethylformamide, N,N-dimethylacetamide, ethyl acetate, methyl acetate, acetonitrile, benzene, xylene, water, toluene, 1,4-dioxane, tetrahydrofuran, and a mixture of these solvents.

The compound (5) thus obtained can be isolated and purified by a method known in the art, for example, concentration, concentration under reduced pressure, crystallization, solvent extraction, reprecipitation or chromatography.

(Step 3)

This step is the method of manufacturing the compound (I-1) of this invention by reducing the compound (5). The reduction reaction used in this step may be a method known by persons skilled in the art. Specifically, the reduction reaction used in this step is, for example, (1) catalytic reduction using hydrogen, formic acid, ammonium formate or hydrazine hydrate, and a palladium, platinum or nickel catalyst, (2) reduction using hydrochloric acid or ammonium chloride, and iron, or (3) reduction using methanol and tin chloride.

The amount of the reducing agent used in the aforesaid reducing reaction varies with the compounds used, the solvent and other reaction conditions, but it is usually 1 to 50 equivalents, and preferably 2 to 20 equivalents, relative to 1 equivalent of the compound (5).

The reaction solvent used is not particularly limited provided that it does not interfere with the reaction. Examples are a halogenated hydrocarbon such as dichloromethane or chloroform, an ether such as diethyl ether, tert-butyl methyl ether or tetrahydrofuran, an amide such as N,N-dimethylformamide or N,N-dimethylacetamide, a sulfoxide such as dimethyl sulfoxide, a nitrile such as acetonitrile, an alcohol such as methanol, ethanol or propanol, an aromatic hydrocarbon such as benzene, toluene or xylene, water, and a mixture of these solvents.

The reaction temperature and reaction time are not particularly limited, but the reaction may be performed at −10° C. to 100° C., preferably 0° C. to 50° C., for 1 to 20 hours, preferably 1 to 5 hours.

The compound (I-1) thus obtained can be isolated and purified by a method known in the art, for example, concentration, concentration under reduced pressure, crystallization, solvent extraction, reprecipitation or chromatography, or it may not be isolated and purified, before proceeding to the next step.

The compounds of the aforesaid steps may have a protecting group on each substituent. This protecting group in each step may be removed by a method known in the art, a corresponding method, or a combination of these methods with conventional methods. Various removal reactions are possible depending on the compounds, type of reaction and other reaction conditions, and the protecting groups can be removed individually or simultaneously, as decided by a person skilled in the art. The protecting group is for, for example, hydroxyl, amino, carboxyl, aldehyde or keto. The removal order of the protecting groups is not particularly limited.

The protecting group for hydroxyl is, for example, a lower alkyl silyl group such as tert-butyl dimethylsilyl or tert-butyl diphenylsilyl, a lower alkoxymethyl group such as methoxymethyl or 2-methoxyethoxymethyl, an aralkyl group such as benzyl or p-methoxybenzyl, or an acyl group such as formyl or acetyl. Among these, tert-butyl dimethylsilyl and acetyl are preferred.

The protecting group for amino is, for example, an aralkyl group such as benzyl or p-nitrobenzyl, an acyl group such as formyl or acetyl, a lower alkoxycarbonyl group such as ethoxycarbonyl or tert-butoxycarbonyl, or an aralkyloxycarbonyl group such as benzyloxycarbonyl or p-nitrobenzyloxycarbonyl. Among these, nitrobenzyl, tert-butoxycarbonyl and benzyloxycarbonyl are preferred.

The protecting group for carboxyl is, for example, a lower alkyl group such as methyl, ethyl or tert-butyl, or an aralkyl group such as benzyl or p-methoxybenzyl. Among these, methyl, ethyl, tert-butyl and benzyl are preferred.

The protecting group for keto is, for example, dimethyl ketal, 1,3-dioxirane, 1,3-dioxolane, 1,3-dithian or 1,3-dithiolane. Among these, dimethyl ketal and 1,3-dioxolane are more preferred.

The protecting group for aldehyde may be dimethyl acetal, 1,3-dioxirane, 1,3-dioxolane, 1,3-dithian or 1,3-dithiolane. Among these, dimethyl acetal and 1,3-dioxolane are more preferred.

In manufacturing the compound of this invention, the protecting group may be introduced into a functional group in order to make the reaction proceed efficiently. These protecting groups can be suitably chosen by a person skilled in the art, and the protecting group can be removed by the method described in "Protective groups in Organic Synthesis", a corresponding method, or a combination thereof with an ordinary method. The removal order of the protecting groups may be decided by a person skilled in the art.

The compound (I-1) thus obtained can be isolated and purified by a method known in the art, for example, concentration, concentration under reduced pressure, crystallization, reprecipitation, solvent extraction or chromatography, or it may not be isolated and purified, before proceeding to the next step.

The compound (I-1) of this invention may also be manufactured by the following steps:

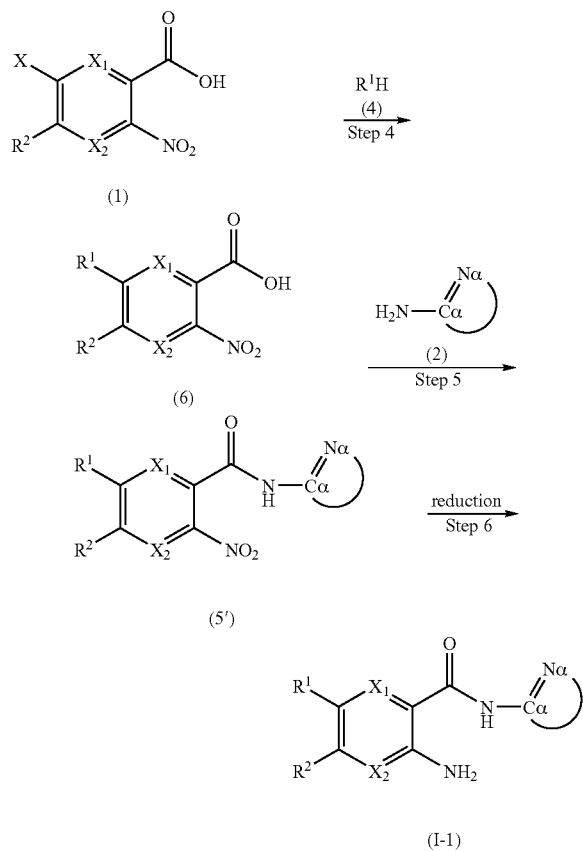

[The Symbols in the Formulae are as Previously Defined]

In the aforesaid Step 4, Step 5 and Step 6, the amount of reagent, reaction solvent, reaction temperature and other reaction conditions may be identical to those of the aforesaid Step 2, Step 1 and Step 3.

When a protecting group is required on $R^2$, a person skilled in the art may suitably select the protecting group by the method described in "Protective Groups in Organic Synthesis", a corresponding method, or a combination thereof with an ordinary method.

The compound (6) or (5') thus obtained can be isolated and purified by a method known in the art, for example, concentration, concentration under reduced pressure, crystallization, reprecipitation or solvent extraction, or it may not be isolated and purified, before proceeding to the next step.

The compound (I-1) of this invention can be isolated and purified by a method known in the art, for example, concentration, concentration under reduced pressure, crystallization, reprecipitation or solvent extraction.

In the aforesaid Steps 1 to 6, the removal of the protecting group is different depending on the type of protecting group and stability of the compound, and it may be performed by the method described in "Protective Groups in Organic Synthesis" (T. W. Green, 2nd edition, John Wiley & Sons, 1991), a corresponding method, or a combination thereof with an ordinary method. For example, this may be performed by solvolysis using an acid or a base, chemical reduction using a hydrogenated metal complex, or catalytic reduction using a palladium charcoal catalyst or Raney nickel catalyst.

The benzamide compound provided by this invention can exist as a pharmaceutically acceptable salt. This salt is described in formula (I) and "Embodiments of the Invention." The salt can be manufactured by the usual methods using the compound represented by formula (I-1). Specifically, when the compound in the aforesaid (I) and (I-1) has a basic group derived, for example, from an amino group or a pyridyl group in the molecule, it can be converted to the corresponding pharmaceutically acceptable salt by treating this compound with an acid.

The acid addition salt is, for example, a hydrohalide salt such as a hydrochloride, hydrofluoride, hydrobromide or hydroiodide; an inorganic acid salt such as a nitrate, perchlorate, sulfate, phosphate or carbonate; a lower alkyl sulfonate such as a methanesulfonate, trifluoromethanesulfonate or ethanesulfonate; an arylsulfonate such as a benzenesulfonate or p-toluenesulfonate; an organic acid salt such as a fumarate, succinate, citrate, tartrate, oxalate or maleate; or an amino acid salt such as a glutamate or aspartate.

If the compound of this invention has an acidic group such as carboxyl in this group, it may be converted to the corresponding pharmaceutically acceptable salt by treating this compound with a base.

The base addition salt is, for example, an alkali metal salt of sodium or potassium, an alkaline earth metal salt of calcium or magnesium, an ammonium salt, or a salt of an organic base such as guanidine, triethylamine or dicyclohexylamine. The compound of this invention may exist as a hydrate or solvate of a free compound or its salt.

Next, the glucokinase activation effect of the compound according to this invention represented by the general formula (I), the accompanying hypoglycemic action and its test method, will be described.

The measurement of the outstanding glucokinase activation effect of the compound represented by the general formula (I) may be performed by the method described in the literature (e.g., Diabetes, Vol. 45, pp. 1671-1677, 1996), or a corresponding method.

The degree of glucokinase activity is investigated not by measuring glucose-6-phosphate directly, but by measuring the amount of Thio-NADH produced when glucose-6-phosphate dehydrogenase, which is a reporter enzyme, generates phosphogluconolactone from glucose-6-phosphate.

The recombinant human liver GK used for this assay was expressed by $E.\ coli$ as a FLAG fusion protein, and was purified by ANTIFLAG M2 AFFINITY GEL (Sigma).

The assay was performed at 30° C. using flat bottom 96-well plate. 69 µl of Assay buffer (25 mM Hepes Buffer: pH=7.2, 2 mM $MgCl_2$, 1 mM ATP, 0.5 mM TNAD, 1 mM dithiothreitol) was pipetted, and 1 µl of a DMSO solution of the compound was added, or 1 µl of DMSO as a control. Next, 20 µl of Enzyme mixture (FLAG-GK, 20 U/ml G6PDH) which had been cooled in ice was pipetted, and 10 µl of 25 mM glucose which is the substrate was added to start the reaction (final glucose concentration=2.5 mM).

After starting the reaction, the increase of absorbance at 405 nm was measured for 10 minutes every 30 seconds, and the compound was evaluated using the increase for the first 5 minutes. FLAG-GK was added so that the absorbance increase after 5 minutes in the presence of 1% DMSO ranged from 0.05 to 0.1.

As a number indicating the GK activity of the compound, AC200 was used. The definition of AC200 is the concentration of compound required to increase the OD value by 2 times (to 200%), taking the OD value of the DMSO control as 100%.

When GK activation ability was measured using the AC200 value as an index of GK activation ability, the compounds shown in the following manufacturing examples showed 200% activity at 10 µM or less.

Next, the fact that the compound of this invention represented by the general formula (I) having the aforesaid GK activation effect has an excellent hypoglycemic action, was confirmed, for example, by the following test method.

To demonstrate the specific hypoglycemic action of the compound in this invention, the compound of Manufacturing Example 33 included in this invention was selected, and its hypoglycemic action was investigated. The effect on blood sugar level when this compound was administered after sugar loading was investigated using the mouse. The test method and test result are shown below.

(Test Method)

A male ICR mouse (8-11th week, n=5) bred under free food intake and water intake conditions, was denied food from the night before the test, and the tip of the tail was cut off slightly with scissors to take blood. The compound suspended in 0.5% methyl cellulose solution wherein glucose was dissolved was then administered orally. As a control, 0.5% methyl cellulose solution wherein glucose had been dissolved, was administered orally to the rat. Blood was collected every 30 minutes after administration of the test drug, and plasma was separated from the obtained blood by centrifugal separation. The blood sugar level in the plasma was assayed by the glucose oxidase method using a commercial test reagent (Detamina GL-E (Kyowa Medex)). The insulin concentration in the plasma was assayed by enzyme immunoassay using a commercial measurement kit (Morinaga Bioscience Laboratory). The obtained numerical values were analyzed by Student's t-test, and the statistical significant difference was computed. The result is shown in FIG. 1.

From the above results, as the benzamide derivative represented by the general formula (I) shows a hypoglycemic action by activating glucokinase, it is useful as a diabetes treatment and/or diabetes prophylactic agent, or as a prophylactic agent for diabetic complications such as diabetic retinopathy, diabetic nephropathy, diabetic arteriosclerosis and diabetic ischemic heart disease.

Since the compound represented by the general formula (I) according to this invention has a glucokinase activation effect, it is useful not only in insulin-dependent diabetes mellitus, but also in non-insulin-dependent diabetes mellitus.

The novel aminobenzamide derivative represented by the formula (I) may be administered orally or parenterally. In using the compound according to this invention in clinical practice, pharmaceutically permitted additives can be added to manufacture various preparations depending on the mode of administration. Various kinds of additives usually used in the pharmaceutical preparation field may then be used. Examples are gelatin, lactose, white sof sugar, titanium oxide, starch, crystalline cellulose, hydroxypropylmethylcellulose, carboxymethylcellulose, corn starch, microcrystalline wax, white vaseline, magnesium aluminometasilicate, calcium phosphate anhydrous, citric acid, trisodium citrate, hydroxypropylcellulose, sorbitol, sorbitan fatty acid ester, polysorbate, sucrose fatty acid ester, polyoxyethylene hydrogenated castor oil, polyvinylpyrrolidone, magnesium stearate, light silicic anhydride, talc, vegetable oil, benzyl alcohol, gum arabic, propylene glycol, polyalkylene glycol, cyclodextrin and hydroxypropyldextrin.

The mixture with these additives may be made into various pharmaceutical preparations, i.e., solid preparations such as tablets, capsules, granules, powders or suppositories; or liquid preparations such as syrups, elixirs or injections. These can be prepared according to the usual method in the field of pharmaceutical preparation. When making up liquid preparations, the compound may, if necessary, be dissolved or suspended in water or another suitable solvent. In the case of injections, it may be dissolved or suspended in physiological saline or glucose solution as required, and buffers and preservatives may further be added.

These pharmaceutical preparations can contain the compound of this invention 1.0 to 100 wt %, preferably 1.0 to 60 wt %.

When the compound according to this invention is used in clinical practice, for example, the dosage and frequency of administration vary with the patient's sex, age, weight, condition, and the kind and extent of results desired, but preferably for an adult, in the case of oral administration, 0.1 to 100 mg/kg is administered one to several times per day, and in the case of parenteral administration, 0.001 to 10 mg/kg is administered one to several times per day.

BEST MODES FOR CARRYING OUT THE INVENTION

The present invention will now be explained in greater detail through Formulation Examples and Manufacturing Examples, with the understanding that the invention is in no way limited to these examples.

FORMULATION EXAMPLE 1

Ten parts of the compound of Manufacturing Example 1, 15 parts of heavy magnesium oxide and 75 parts of lactose were uniformly mixed to prepare pulverulent or finely-granular powders with sizes of no greater than 350 µm. The powders were placed in capsule containers to prepare capsules.

FORMULATION EXAMPLE 2

Forty-five parts of the compound of Manufacturing Example 1, 15 parts of starch, 16 parts of lactose, 21 parts of crystalline cellulose, 3 parts of polyvinyl alcohol and 30 parts of distilled water were uniformly mixed, and the mixture was subsequently crushed, granulated and dried, and then filtered to prepare granules with diameters of 1410 to 177 µm.

FORMULATION EXAMPLE 3

After preparing granules by the same method as in Formulation Example 2, 3 parts of calcium stearate was added to 96 parts of the granules, and the mixture was compressed and molded to form tablets with diameters of 10 mm.

FORMULATION EXAMPLE 4

Ten parts of crystalline cellulose and 3 parts of calcium stearate were added to 90 parts of the granules obtained by the method in Formulation Example 2, and the mixture was compressed and molded to form tablets with diameters of 8 mm. Then a mixed suspension of syrup gelatin and sedimentary calcium carbonate was added to prepare sugar-coated tablets.

The present invention will now be explained in greater detail through Manufacturing Examples and Reference Examples, with the understanding that the invention is in no way limited to these examples.

The thin-layer chromatography carried out in the examples employed Silicagel 60F$_{245}$ (Merck) as the plate and a UV detector as the detector. The column silica gel used was Wakogel™ C-300 (Wako Pure Chemical Industries), and the reverse-phase column silica gel used was LC-SORB™ SP-B-ODS (Chemco) or YMC-GEL™ ODS-AQ 120-S50 (Yamamura Chemicals Lab).

The abbreviations in the examples are explained below.
i-Bu: isobutyl
n-Bu: n-butyl
t-Bu: t-butyl
Me: methyl
Et: ethyl
Ph: phenyl
i-Pr: isopropyl
n-Pr: n-propyl
CDCl$_3$: heavy chloroform
CD$_3$OD: heavy methanol
DMSO-d$_6$: heavy dimethylsulfoxide The abbreviations for the nuclear magnetic resonance spectra are explained below.
s: singlet
d: doublet
dd: double doublet
t: triplet
m: multiplet
br: broad
q: quartet
J: coupling constant
Hz: Hertz

MANUFACTURING EXAMPLE 1

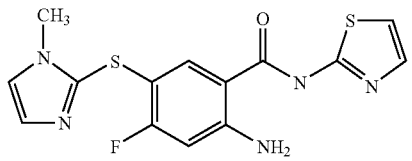

Preparation of 2-amino-4-fluoro-5-(1-methyl-1H-imidazol-2-ylsulfanyl)-N-thiazol-2-ylbenzamide Two drops of N,N-dimethylformamide and 0.51 ml (5.91 mmol) of oxalyl chloride were dripped into a methylene chloride solution (20 ml) of 1.00 g (4.92 mmol) of 4,5-difluoro-2-nitrobenzoic acid on ice, and after the addition was completed, the reaction mixture was stirred at room temperature for 1 hour. The reaction mixture was concentrated under reduced pressure, and an acid chloride was obtained as a colorless oily material.

0.91 ml (9.84 mmol) of pyridine was added to a methylene chloride solution (10 ml) of 493 mg (4.92 mmol) of 2-aminothiazole, the methylene chloride solution (5 ml) of the acid chloride previously obtained was dripped in on ice, and after the addition was completed, the reaction mixture was stirred at room temperature overnight. An aqueous solution of 1 N hydrochloric acid was added to the reaction mixture, the mixture was extracted with chloroform, and then the organic layer was washed with water, an aqueous solution of saturated sodium bicarbonate and saturated brine solution, dried, and concentrated under reduced pressure. The obtained residue was recrystallized from chloroform, and 923 mg of an amide was obtained as a light yellow solid (yield: 66%).

1.35 ml (9.68 mmol) of triethylamine and 443 mg (3.87 mmol) of 1-methyl-2-mercaptothioimidazole were added to an acetonitrile solution (10.0 ml) of 920 mg (3.23 mmol) of the obtained amide, and the reaction mixture was heated under reflux overnight. The reaction mixture was concentrated under reduced pressure, the obtained residue was recrystallized from methanol, and 552 mg of a nitro compound was obtained as a yellow solid (yield: 45%).

2.4 g of iron powder was added to a mixture of an isopropanol solution (20 ml) of 480 mg (1.27 mmol) of the obtained nitro compound and an aqueous solution (2 ml) of saturated ammonium chloride, and heated under reflux for 30 minutes. After cerite filtration, the reaction mixture was concentrated under reduced pressure, and the obtained residue was purified by silica gel column chromatography (chloroform:methanol=8:1) to obtain 270 mg of the title compound as white crystals (yield: 55%).

$^1$HNMR(CD$_3$OD) δ: 3.79 (3H, s), 6.51 (1H, d, J=11.4 Hz), 6.62 (1H, d, J=1.0 Hz), 7.00 (1H, d, J=1.3 Hz), 7.17 (1H, d, J=1.3 Hz), 8.04 (1H, d, J=8.0 Hz) ESI-MS(m/e): 350 [M+H]$^+$

The compounds of Manufacturing Examples 2 to 82 were obtained by the same method as in Manufacturing Example 1. Analytical data for compounds of representative manufacturing examples are given below.

MANUFACTURING EXAMPLE 2

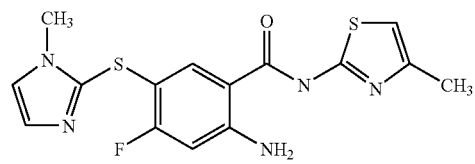

Preparation of 2-amino-4-fluoro-5-(1-methyl-1H-imidazol-2-ylsulfanyl)-N-(4-methylthiazol-2-yl)benzamide $^1$HNMR(CD$_3$OD) δ: 2.33 (3H, d, J=1.0 Hz), 3.79 (3H, s), 6.51 (1H, d, J=11.4 Hz), 6.62 (1H, d, J=1.0 Hz), 7.00 (1H, d, J=1.3 Hz), 7.17 (1H, d, J=1.3 Hz), 8.04 (1H, d, J=8.0 Hz) FAB-MS(m/e): 364[M+H]$^+$

MANUFACTURING EXAMPLE 3

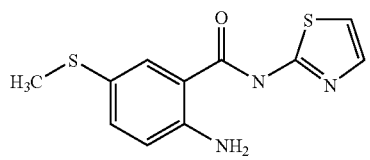

Preparation of 2-amino-5-methylsulfanyl-N-thiazol-2-ylbenzamide $^1$HNMR(CDCl$_3$) δ: 2.39 (3H, s), 6.72 (1H, d, J=8.5 Hz), 6.97 (1H, d, J=3.6 Hz), 7.30-7.37 (2H, m), 7.65 (1H, d, J=3.0 Hz) FAB-MS(m/e): 266[M+H]$^+$

MANUFACTURING EXAMPLE 4

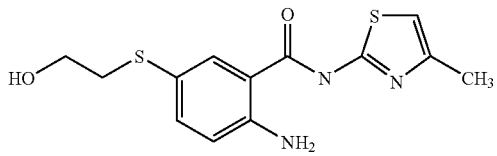

Preparation of 2-amino-5-(2-hydroxyethanesulfanyl)-N-(4-methylthiazol-2-yl)benzamide $^1$HNMR(CD$_3$OD) δ: 2.30 (3H, d, J=1.1 Hz), 2.91 (2H, t, J=6.9 Hz), 3.63 (2H, t, J=6.9 Hz), 6.64 (1H, d, J=1.1 Hz), 6.76 (1H, d, J=8.6 Hz), 7.37 (1H, dd, J=2.1 Hz, 8.6 Hz), 7.84 (1H, d, J=2.1 Hz) FAB-MS(m/e): 310 [M+H]$^+$

MANUFACTURING EXAMPLE 5

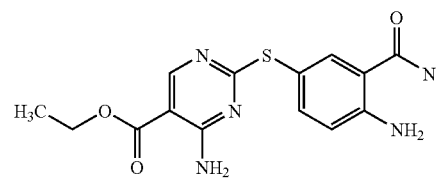

Preparation of 2-amino-5-(4-amino-5-ethoxycarbonylpyrimidin-2-ylsulfanyl)-N-(4-methylthiazol-2-yl)benzamide $^1$HNMR(CD$_3$OD) δ: 1.34 (3H, t, J=7.2 Hz), 2.31 (3H, d, J=1.0 Hz), 4.32 (2H, q, J=7.2 Hz), 6.63 (1H, s), 6.85 (1H, d, J=8.7 Hz), 7.38 (1H, dd, J=2.2 Hz, 8.7 Hz), 7.94 (1H, d, J=2.2 Hz), 8.55 (1H, s) FAB-MS(m/e): 431 [M+H]$^+$

MANUFACTURING EXAMPLE 6

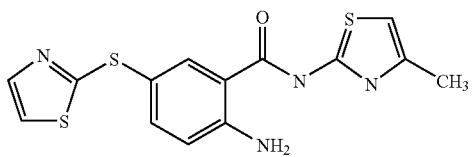

Preparation of 2-amino-5-(thiazol-2-ylsulfanyl)-N-(4-methylthiazol-2-yl)benzamide $^1$HNMR(CD$_3$OD) δ: 2.31 (1H, d, J=1.0 Hz), 6.63 (1H, s), 6.88 (1H, d, J=8.7 Hz), 7.38 (1H, d, J=3.0 Hz), 7.48 (1H, dd, J=2.1 Hz, 8.7 Hz), 7.62 (1H, d, J=3.0 Hz), 8.13 (1H, d, J=2.1 Hz) FAB-MS(m/e): 349[M+H]$^+$

MANUFACTURING EXAMPLE 7

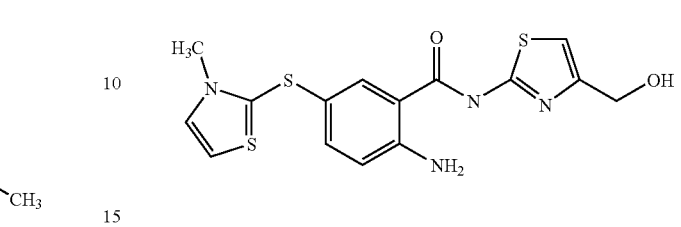

Preparation of 2-amino-5-(1-methyl-1H-imidazol-2-ylsulfanyl)-N-(4-hydroxymethylthiazol-2-yl)benzamide $^1$HNMR(DMSO-d$_6$) δ: 3.64 (3H, s), 4.49 (2H, d, J=6.0 Hz), 5.24 (1H, t, J=6.0 Hz), 6.74 (1H, d, J=8.8 Hz), 6.93 (1H, s), 6.94 (1H, s), 7.16 (1H, dd, J=1.6 Hz, 8.8 Hz), 7.29 (1H, s), 7.99 (1H, d, J=1.6 Hz) FAB-MS(m/e): 362[M+H]$^+$

MANUFACTURING EXAMPLE 8

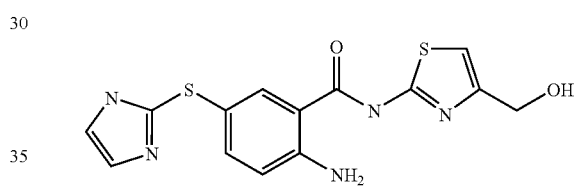

Preparation of 2-amino-5-(1H-imidazol-2-ylsulfanyl)-N-(4-hydroxymethylthiazol-2-yl)benzamide $^1$HNMR(DMSO-d$_6$) δ: 4.48 (2H, s), 5.22 (1H, br), 6.74 (1H, d, J=8.8 Hz), 6.92 (2H, s), 7.17 (1H, s), 7.23 (1H, d, J=8.8 Hz), 8.05 (1H, s) FAB-MS(m/e): 348[M+H]$^+$

MANUFACTURING EXAMPLE 9

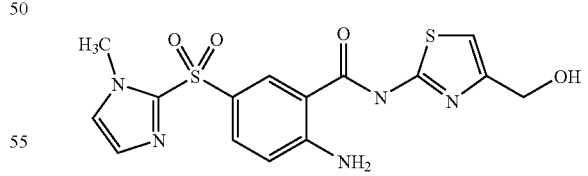

Preparation of 2-amino-5-(1-methyl-1H-imidazol-2-ylsulfonyl)-N-(4-hydroxymethylthiazol-2-yl)benzamide $^1$HNMR(DMSO-d$_6$) δ: 3.88 (3H, s), 4.46 (2H, s), 5.25 (1H, br), 6.87 (1H, d, J=8.4 Hz), 6.90 (1H, s), 7.02 (1H, s), 7.40 (1H, s), 7.52 (1H, s), 7.62 (1H, d, J=8.4 Hz) FAB-MS (m/e): 394[M+H]$^+$

MANUFACTURING EXAMPLE 10

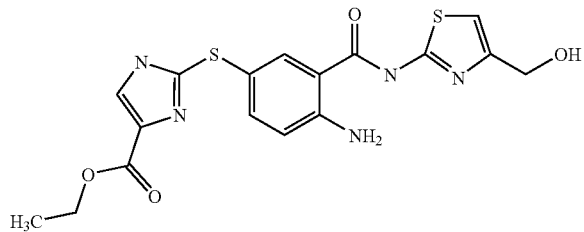

Preparation of 2-amino-5-(4-ethoxycarbonyl-1H-imidazol-2-ylsulfanyl)-N-(4-hydroxymethylthiazol-2-yl)benzamide $^1$HNMR(CD$_3$OD) δ: 1.33 (3H, t, J=7.1 Hz), 4.29 (2H, q, J=7.1 Hz), 4.60 (2H, d, J=0.9 Hz), 6.79 (1H, d, J=8.7 Hz), 6.93 (1H, d, J=0.9 Hz), 7.39 (1H, dd, J=2.1 Hz, 8.7 Hz), 7.68-7.69 (1H, m), 8.00 (1H, d, J=2.1 Hz) FAB-MS(m/e): 420[M+H]$^+$

MANUFACTURING EXAMPLE 11

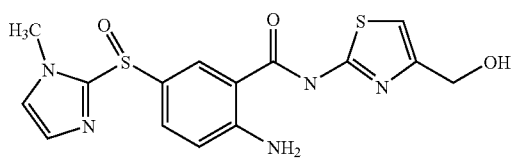

Preparation of 2-amino-5-(1-methyl-1H-imidazol-2-ylsulfinyl)-N-(4-hydroxymethylthiazol-2-yl)benzamide $^1$HNMR(DMSO-d$_6$) δ: 3.70 (3H, s), 4.46 (2H, s), 5.21 (1H, br), 6.88 (1H, s), 6.89 (1H, d, J=8.8 Hz), 7.03 (1H, s), 7.35 (1H, s), 7.38 (1H, d, J=8.8 Hz), 8.14 (1H, s) FAB-MS (m/e): 378[M+H]$^+$

MANUFACTURING EXAMPLE 12

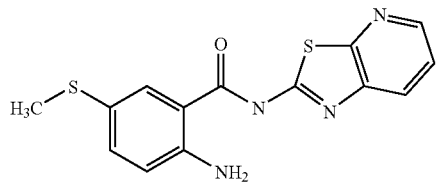

Preparation of 2-amino-5-methylsulfanyl-N-thiazolo[5,4-b]pyridin-2-ylbenzamide $^1$HNMR(CDCl$_3$) δ: 2.39 (3H, s), 5.84 (2H, br), 6.74 (1H, d, J=8.4 Hz), 7.34 (1H, d, J=4.8 Hz), 7.38 (1H, dd, J=2.0 Hz, 8.4 Hz), 7.61 (1H, d, J=2.0 Hz), 7.89 (1H, dd, J=1.2 Hz, 8.4 Hz), 8.81 (1H, dd, J=1.2 Hz, 4.8 Hz) FAB-MS(m/e): 317 [M+H]$^+$

MANUFACTURING EXAMPLE 13

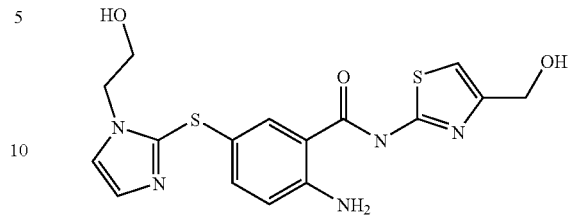

Preparation of 2-amino-5-(1-hydroxyethyl-1H-imidazol-2-ylsulfanyl)-N-(4-hydroxymethylthiazol-2-yl) benzamide $^1$HNMR(CD$_3$OD) δ: 3.73 (2H, t, J=4.8 Hz), 4.27 (2H, t, J=4.8 Hz), 4.61 (2H, s), 6.74 (1H, d, J=8.8 Hz), 6.93 (1H, s), 7.04 (1H, s), 7.27-7.30 (2H, m), 7.89 (1H, s) FAB-MS(m/e): 392[M+H]$^+$

MANUFACTURING EXAMPLE 14

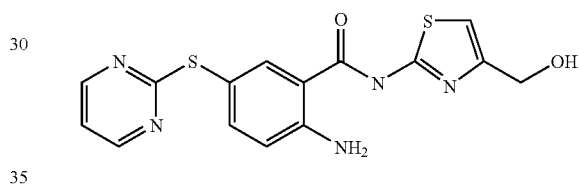

Preparation of 2-amino-5-(pyrimidin-2-ylsulfanyl)-N-(4-hydroxymethylthiazol-2-yl)benzamide $^1$HNMR(CDCl$_3$) δ: 4.44 (2H, d, J=5.2 Hz), 5.18 (1H, t, J=5.2 Hz), 6.81 (1H, d, J=8.4 Hz), 6.87 (1H, s), 7.04 (2H, br), 7.16 (1H, d, J=8.8 Hz), 7.32 (1H, d, J=8.8 Hz), 8.13 (1H, s), 8.84 (2H, d, J=8.4 Hz) FAB-MS(m/e): 360[M+H]$^+$

MANUFACTURING EXAMPLE 15

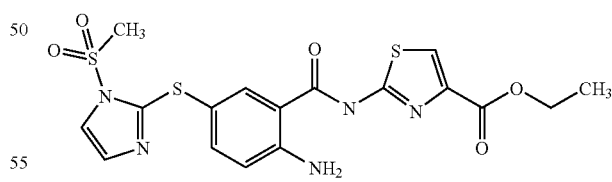

Preparation of 2-amino-5-(1-methanesulfonyl-1H-imidazol-2-ylsulfanyl)-N-(4-ethoxycarbonylthiazol-2-yl) benzamide $^1$HNMR(CDCl$_3$) δ: 1.31 (3H, t, J=7.2 Hz), 3.41 (3H, s), 4.30 (2H, q, J=7.2 Hz), 6.69 (1H, d, J=8.4 Hz), 6.88 (1H, d, J=2.0 Hz), 7.32 (1H, d, J=2.06 Hz), 7.40 (1H, dd, J=2.0 Hz, 8.4 Hz), 7.74 (1H, s), 7.95 (1H, d, J=2.0 Hz) FAB-MS(m/e): 468[M+H]$^+$

MANUFACTURING EXAMPLE 16

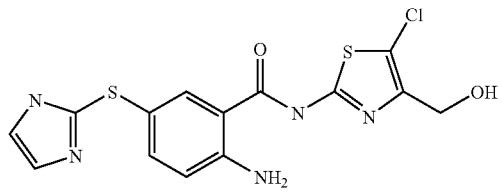

Preparation of 2-amino-5-(1H-imidazol-2-ylsulfanyl)-N-(4-hydroxymethyl-5-chlorothiazol-2-yl)benzamide $^1$HNMR(CD$_3$OD) δ: 4.56 (2H, s), 6.76 (1H, d, J=8.8 Hz), 7.05 (2H, s), 7.34 (1H, dd, J=2.0 Hz, 8.8 Hz), 7.95 (1H, d, J=2.0 Hz) FAB-MS(m/e): 382[M+H]$^+$

MANUFACTURING EXAMPLE 17

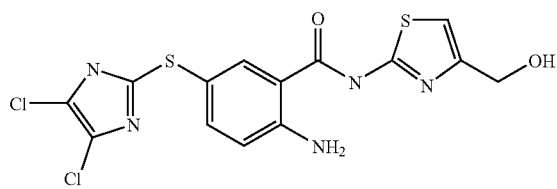

Preparation of 2-amino-5-(4,5-dichloro-1H-imidazol-2-ylsulfanyl)-N-(4-hydroxymethylthiazol-2-yl)benzamide $^1$HNMR(CD$_3$OD) δ: 4.60 (2H, s), 6.79 (1H, d, J=2.0 Hz), 6.93 (1H, s), 7.37 (1H, dd, J=2.0 Hz, 8.8 Hz), 7.95 (1H, d, J=2.0 Hz) FAB-MS(m/e): 416[M+H]$^+$

MANUFACTURING EXAMPLE 18

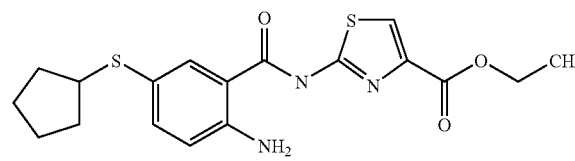

Preparation of 2-amino-5-cyclopentylsulfanyl-N-(4-ethoxycarbonylthiazol-2-yl)benzamide $^1$HNMR(CDCl$_3$) δ: 1.35 (3H, t, J=6.0 Hz), 1.49-1.92 (8H, m), 3.29-3.33 (1H, m), 4.34 (2H, q, J=6.0 Hz), 5.89 (2H, s), 6.66 (1H, d, J=8.8 Hz), 7.38 (1H, dd, J=2.0 Hz, 8.8 Hz), 7.58 (1H, d, J=2.0 Hz), 7.87 (1H, s) FAB-MS(m/e): 392[M+H]$^+$

MANUFACTURING EXAMPLE 19

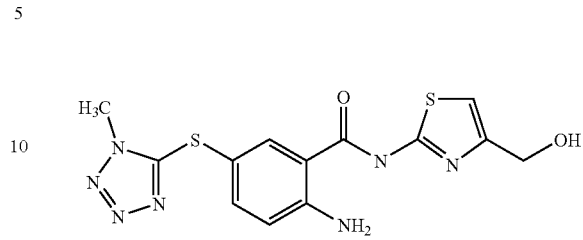

Preparation of 2-amino-5-(1-methyl-1H-tetrazol-5-ylsulfanyl)-N-(4-hydroxymethylthiazol-2-yl)benzamide $^1$HNMR(CD$_3$OD) δ: 4.03 (3H, s), 4.60 (2H, s), 6.82 (1H, d, J=8.8 Hz), 6.88 (1H, s), 7.43 (1H, dd, J=2.4 Hz, 8.8 Hz), 8.01 (1H, d, J=2.4 Hz) FAB-MS(m/e): 364[M+H]$^+$

MANUFACTURING EXAMPLE 20

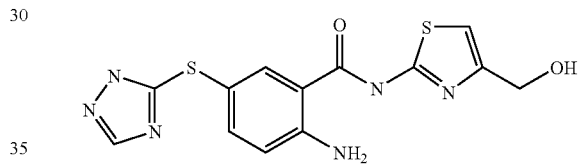

Preparation of 2-amino-5-(2H-[1,2,4]triazol-5-ylsulfanyl)-N-(4-hydroxymethylthiazol-2-yl)benzamide $^1$HNMR(CD$_3$OD) δ: 4.60 (2H, s), 6.81 (1H, d, J=8.8 Hz), 6.93 (1H, s), 7.42 (1H, dd, J=2.0 Hz, 8.8 Hz), 7.90 (1H, s), 8.01 (1H, d, J=2.0 Hz), 8.27 (1H, brs) FAB-MS(m/e): 349[M+H]$^+$

MANUFACTURING EXAMPLE 21

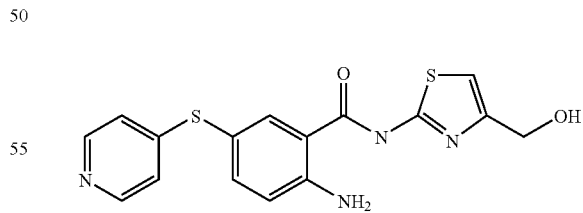

Preparation of 2-amino-5-(pyridine-4-ylsulfanyl)-N-(4-hydroxymethylthiazol-2-yl)benzamide $^1$HNMR(CD$_3$OD) δ: 4.57 (1H, s), 6.91-6.94 (2H, m), 7.04 (2H, d, J=4.8 Hz), 7.40 (1H, d, J=8.8 Hz), 7.99 (1H, s), 8.23 (2H, d, J=4.8 Hz) FAB-MS(m/e): 359[M+H]$^+$

MANUFACTURING EXXAMPLE 22

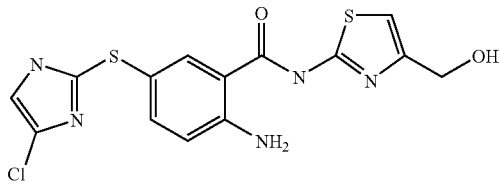

Preparation of 2-amino-5-(4-chloro-1H-imidazol-2ylsulfanyl)-N-(4-hydroxymethylthiazol-2-yl)benzamide $^1$HNMR(CD$_3$OD) δ: 4.60 (2H, s), 6.78 (1H, d, J=8.4 Hz), 6.93 (1H, s), 7.05 (1H, s), 7.37 (1H, d, J=8.4 Hz), 7.97 (1H, s) FAB-MS(m/e): 382[M+H]$^+$

MANUFACTURING EXAMPLE 23

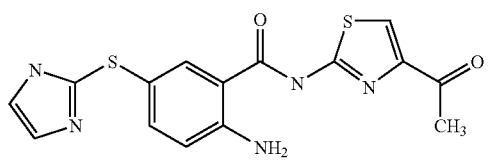

Preparation of 2-amino-5-(1H-imidazol-2-ylsulfanyl)-N-(4-acetylthiazol-2-yl)benzamide $^1$HNMR(DMSO-d$_6$) δ: 2.52 (3H, s), 6.74 (1H, d, J=8.8 Hz), 6.90 (1H, s), 7.16 (1H, s), 7.24 (1H, d, J=8.8 Hz), 8.13 (2H, s) FAB-MS(m/e): 360[M+H]$^+$

MANUFACTURING EXAMPLE 24

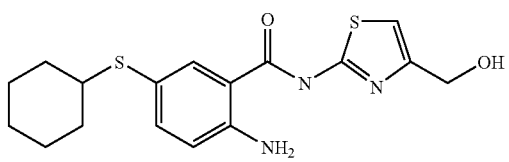

Preparation of 2-amino-5-cyclohexylsulfanyl-N-(4-hydroxymethylthiazol-2-yl)benzamide $^1$HNMR(DMSO-d$_6$) δ: 1.10-1.30 (6H, brs), 1.60-1.75 (2H, brs), 1.80-1.90 (2H, brs), 2.90-3.00 (1H, brs), 4.47 (2H, s), 5.20-5.22 (1H, brs), 6.71 (1H, dd, J=2.8 Hz, 8.8 Hz), 6.91 (1H, s), 7.24 (1H, d, J=8.8 Hz), 7.93 (1H, s) FAB-MS(m/e): 364[M+H]$^+$

MANUFACTURING EXAMPLE 25

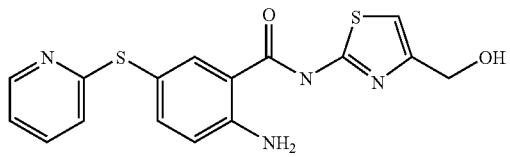

Preparation of 2-amino-5-(pyridin-2-ylsulfanyl)-N-(4-hydroxymethylthiazol-2-yl)benzamide $^1$HNMR(CD$_3$OD) δ: 4.57 (2H, s), 6.80-6.92 (3H, m), 7.08 (1H, dt, J=5.0 Hz, 7.6 Hz), 7.42 (1H, dd, J=1.6 Hz, 8.0 Hz), 7.59 (1H, dt, J=2.0 Hz, 7.6 Hz), 8.01 (1H, d, J=1.6 Hz), 8.31 (1H, d, J=5.0 Hz) FAB-MS(m/e): 359[M+H]$^+$

MANUFACTURING EXAMPLE 26

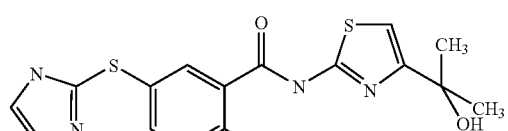

Preparation of 2-amino-5-(1H-imidazol-2-ylsulfanyl)-N-(4-[1-hydroxy-1-methylethyl]thiazol-2-yl)benzamide $^1$HNMR(CD$_3$OD) δ: 1.56 (6H, s), 6.74 (1H, d, J=8.8 Hz), 6.87 (1H, s), 7.05 (2H, s), 7.33 (1H, d, J=8.8 Hz), 7.97 (1H, s) FAB-MS(m/e): 376[M+H]$^+$

MANUFACTURING EXAMPLE 27

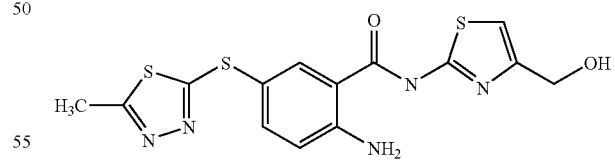

Preparation of 2-amino-5-(5-methyl-[1,3,4]thiadiazol-2-ylsulfanyl)-N-(4-hydroxymethylthiazol-2-yl)benzamide $^1$HNMR(CDCl$_3$) δ: 2.66 (3H, s), 4.63 (1H, s), 6.86 (1H, d, J=8.4 Hz), 6.88 (1H, s), 7.51 (1H, dd, J=2.0 Hz, 8.4 Hz), 8.09 (1H, d, J=2.0 Hz) FAB-MS(m/e): 380[M+H]$^+$

MANUFACTURING EXAMPLE 28

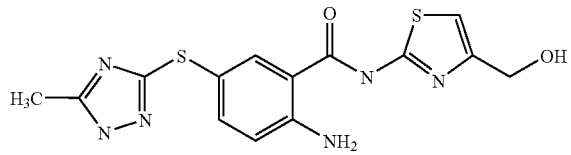

Preparation of 2-amino-5-(5-methyl-1H-[1,2,4]triazol-3-ylsulfanyl)-N-(4-hydroxymethylthiazol-2-yl)benzamide $^1$HNMR(CD$_3$OD) δ: 2.36 (3H, s), 4.60 (2H, s), 6.79 (1H, d, J=8.8 Hz), 6.93 (1H, s), 7.40 (1H, dd, J=1.6 Hz, 8.8 Hz), 7.98 (1H, d, J=1.6 Hz) FAB-MS(m/e): 363[M+H]$^+$

MANUFACTURING EXAMPLE 29

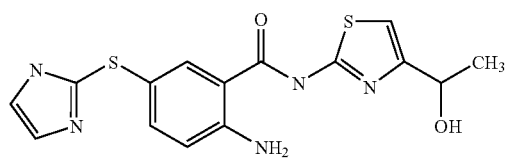

Preparation of 2-amino-5-(1H-imidazol-2-ylsulfanyl)-N-[4-(1-hydroxyethyl)thiazol-2-yl]benzamide $^1$HNMR(CD$_3$OD) δ: 1.50 (3H, d, J=6.8 Hz), 4.85 (1H, q, J=6.8 Hz), 6.76 (1H, d, J=8.8 Hz), 6.89 (1H, s), 7.05 (1H, s), 7.34 (1H, dd, J=1.5 Hz, 8.8 Hz), 7.96 (1H, d, J=1.5 Hz) FAB-MS(m/e): 362[M+H]$^+$

MANUFACTURING EXAMPLE 30

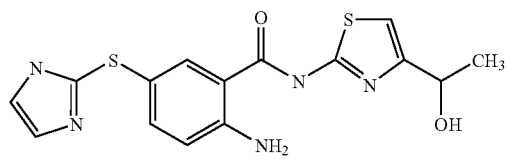

Preparation of 2-amino-5-(1H-imidazol-5-ylsulfanyl)-N-[4-(1-hydroxyethyl)thiazol-2-yl]benzamide $^1$HNMR(CD$_3$OD) δ: 1.50 (3H, d, J=6.8 Hz), 4.85 (1H, q, J=6.8 Hz), 6.76 (1H, d, J=8.8 Hz), 6.89 (1H, s), 7.05 (1H, s), 7.34 (1H, dd, J=1.5 Hz, 8.8 Hz), 7.96 (1H, d, J=1.5 Hz) FAB-MS(m/e): 362[M+H]$^+$

MANUFACTURING EXAMPLE 31

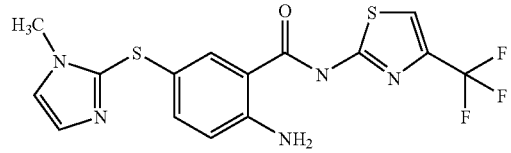

Preparation of 2-amino-5-(1-methyl-1H-imidazol-5-ylsulfanyl)-N-(4-trifluoromethylthiazol-2-yl)benzamide $^1$HNMR(CD$_3$OD) δ: 3.75 (3H, s), 6.75 (1H, d, J=8.8 Hz), 7.02 (1H, s), 7.19 (1H, s), 7.29 (1H, dd, J=1.2 Hz, 8.8 Hz), 7.64 (1H, s), 7.95 (1H, d, J=1.2 Hz) FAB-MS(m/e): 400[M+H]$^+$

MANUFACTURING EXAMPLE 32

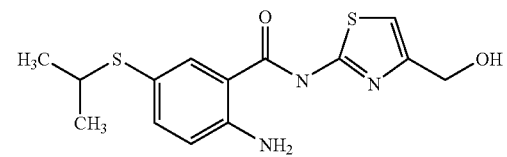

In FIG. 1, Cpd-A shows the compound mentioned in Manufacturing Example 33 below.

In addition to the aforesaid method, the hypoglycemic action of the compound of this invention can be measured also by the method described in the literature (Proc. Natl. Acad. Sci., 92:3096-3099, 1995), a corresponding method, or a combination of these with an ordinary test method.

Using the AC200 value as an index of the GK activation ability of the compound, the compounds of Manufacturing Examples 1 to 117 all showed 200% activity at 10 μM or less. Therefore, the compound according to this invention is useful as a medication for diabetic therapy and/or prevention.

Preparation of 2-amino-5-(1-methylethyl)sulfanyl-N-(4-hydroxymethylthiazol-2-yl)benzamide $^1$HNMR(CD$_3$OD) δ: 1.21 (6H, d, J=6.8 Hz), 3.14-3.18 (1H, m), 4.59 (2H, s), 6.76 (1H, d, J=8.4 Hz), 6.93 (1H, s), 7.34 (1H, dd, J=2.4 Hz, 8.4 Hz), 7.83 (1H, d, J=2.4 Hz) FAB-MS(m/e): 324[M+H]$^+$

MANUFACTURING EXAMPLE 33

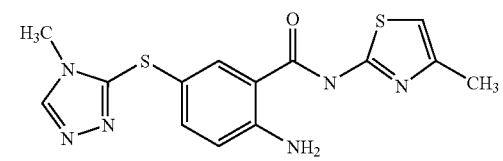

Preparation of 2-amino-5-(4-methyl-4H-[1,2,4]triazol-3-ylsulfanyl)-N-(4-methylthiazol-2-yl)benzamide $^1$HNMR(CD$_3$OD) δ: 2.32 (3H, d, J=1.0 Hz), 3.71 (3H, s), 6.62 (1H, d, J=1.0 Hz), 6.78 (1H, d, J=8.7 Hz), 7.36 (1H, dd, J=2.2 Hz, 8.7 Hz), 8.00 (1H, d, J=2.2 Hz), 8.50 (1H, s) FAB-MS(m/e): 347[M+H]$^+$

MANUFACTURING EXAMPLE 34

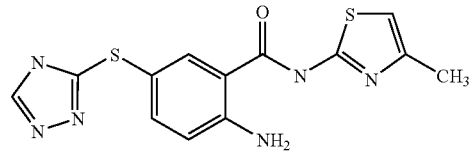

Preparation of 2-amino-5-(4H-[1,2,4]triazol-3-ylsulfanyl)-N-(4-methylthiazol-2-yl)benzamide $^1$HNMR(CD$_3$OD) δ: 2.28 (3H, d, J=1.0 Hz), 6.59 (1H, d, J=1.0 Hz), 6.75 (1H, d, J=8.6 Hz), 7.36 (1H, dd, J=2.2 Hz, 8.6 Hz), 7.97 (1H, d, J=2.2 Hz), 8.22 (1H, S) FAB-MS(m/e): 333[M+H]$^+$

MANUFACTURING EXAMPLE 35

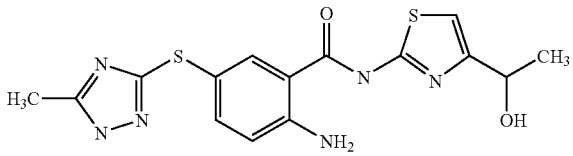

Preparation of 2-amino-5-(5-methyl-1H-[1,2,4]triazol-3-ylsulfanyl)-N-[4-(1-hydroxyethyl)thiazol-2-yl]benzamide $^1$HNMR(CD$_3$OD) δ: 1.50 (3H, d, J=6.6 Hz), 2.37 (3H, s), 4.84 (1H, q, J=6.6 Hz), 6.79 (1H, d, J=8.4 Hz), 6.89 (1H, s), 7.40 (1H, dd, J=2.0 Hz, 8.4 Hz), 7.99 (1H, d, J=2.0 Hz) FAB-MS (m/e): 377 [M+H]$^+$

MANUFACTURING EXAMPLE 36

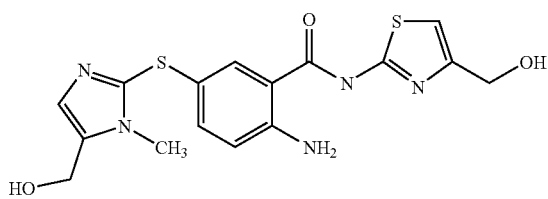

Preparation of 2-amino-5-(2-hydroxymethyl-1-methyl-1H-imidazol-3-ylsulfanyl)-N-(4-hydroxymethylthiazol-2-yl)benzamide $^1$HNMR(CD$_3$OD) δ: 3.75 (3H, s), 4.55 (2H, s), 4.60 (2H, d, J=0.8 Hz), 6.74 (1H, d, J=8.7 Hz), 6.92 (1H, s), 6.99 (1H, s), 7.27 (1H, dd, J=2.1 Hz, 8.7 Hz), 7.90 (1H, d, J=0.8 Hz) FAB-MS(m/e): 392[M+H]$^+$

MANUFACTURING EXAMPLE 37

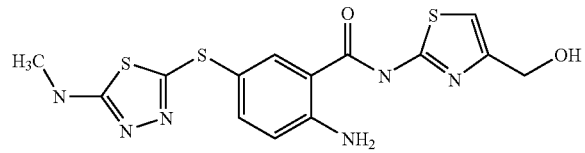

Preparation of 2-amino-5-(5-methylamino-[1,3,4]thiadiazol-2-ylsulfanyl)-N-(4-hydroxymethylthiazol-2-yl)benzamide $^1$HNMR(CD$_3$OD) δ: 2.90 (3H, s), 4.59 (2H, s), 6.84 (1H, d, J=8.8 Hz), 6.93 (1H, s), 7.46 (1H, dd, J=2.0 Hz, 8.8 Hz), 8.05 (1H, d, J=2.0 Hz) FAB-MS (m/e): 395 [M+H]$^+$

MANUFACTURING EXAMPLE 38

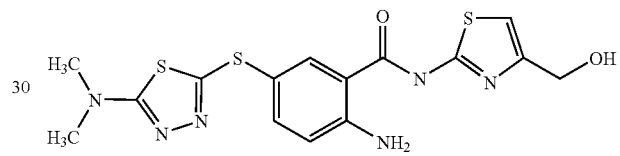

Preparation of 2-amino-5-(5-dimethylamino-[1,3,4]thiadiazol-2-ylsulfanyl)-N-(4-hydroxymethylthiazol-2-yl)benzamide $^1$HNMR(CD$_3$OD) δ: 3.05 (6H, s), 4.59 (2H, s), 6.84 (1H, d, J=8.8 Hz), 6.93 (1H, s), 7.46 (1H, dd, J=2.0 Hz, 8.8 Hz), 8.05 (1H, d, J=2.0 Hz) FAB-MS(m/e): 409[M+H]$^+$

MANUFACTURING EXAMPLE 39

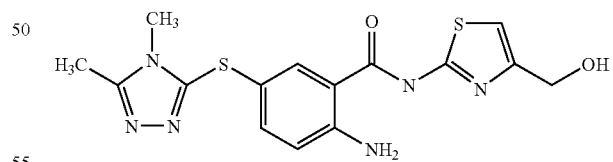

Preparation of 2-amino-5-(4,5-dimethyl-4H-[1,2,4]triazol-3-ylsulfanyl)-N-(4-hydroxymethylthiazol-2-yl)benzamide $^1$HNMR(CD$_3$OD) δ: 2.42 (3H, s), 3.62 (3H, s), 4.60 (2H, s), 6.78 (1H, d, J=8.8 Hz), 6.93 (1H, s), 7.37 (1H, dd, J=2.1 Hz, 8.8 Hz), 7.97 (1H, d, J=2.1 Hz) FAB-MS(m/e): 377[M+H]$^+$

MANUFACTURING EXAMPLE 40

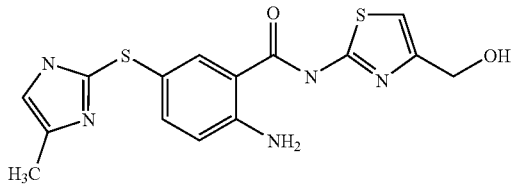

Preparation of 2-amino-5-(4-methyl-1H-imidazol-2-ylsulfanyl)-N-(4-hydroxymethylthiazol-2-yl)benzamide $^1$HNMR(CD$_3$OD) δ: 2.00 (3H, s), 4.60 (2H, s), 6.74 (1H, s), 6.75 (1H, d, J=8.4 Hz), 6.93 (1H, s), 7.32 (1H, dd, J=2.0 Hz, 8.4 Hz), 7.93 (1H, d, J=2.0 Hz) FAB-MS(m/e): 362[M+H]$^+$

MANUFACTURING EXAMPLE 41

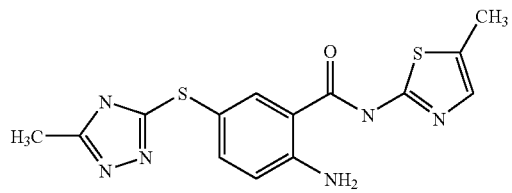

Preparation of 2-amino-5-(5-methyl-4H-[1,2,4]triazol-3-ylsulfanyl)-N-(5-methylthiazol-2-yl)benzamide $^1$HNMR(CD$_3$OD) δ: 2.35 (3H, s), 2.38 (3H, d, J=1.1 Hz), 6.77 (1H, d, J=8.6 Hz), 7.09 (1H, d, J=1.1 Hz), 7.38 (1H, dd, J=2.0 Hz, 8.6 Hz), 7.97 (1H, d, J=2.0 Hz) FAB-MS(m/e): 347[M+H]$^+$

MANUFACTURING EXAMPLE 42

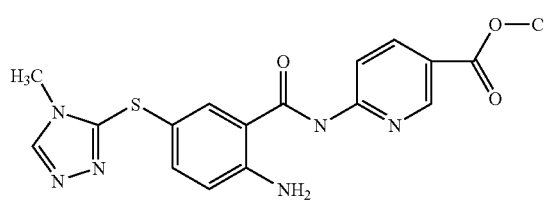

Preparation of 2-amino-5-(4-methyl-4H-[1,2,4]triazol-3-ylsulfanyl)-N-(5-ethoxycarbonylpyridin-2-yl)benzamide $^1$HNMR(CD$_3$OD) δ: 3.72 (3H, s), 3.92 (3H, s), 6.79 (1H, d, J=8.7 Hz), 7.38 (1H, dd, J=2.1 Hz, 8.7 Hz), 7.96 (1H, d, J=2.1 Hz), 8.30-8.32 (2H, m), 8.51 (1H, s), 8.91-8.93 (1H, s) FAB-MS(m/e): 385[M+H]$^+$

MANUFACTURING EXAMPLE 43

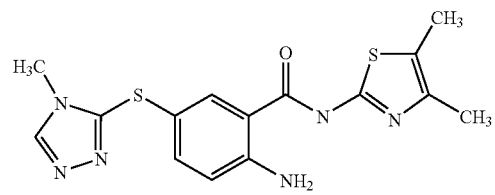

Preparation of 2-amino-5-(4-methyl-4H-[1,2,4]triazol-3-ylsulfanyl)-N-(4,5-dimethylthiazol-2-yl)benzamide $^1$HNMR(CD$_3$OD) δ: 2.17 (3H, s), 2.22 (3H, s), 3.58 (3H, s), 6.75 (1H, d, J=8.6 Hz), 7.26 (1H, dd, J=2.2 Hz, 8.6 Hz), 8.09 (1H, d, J=2.2 Hz), 8.57 (1H, s) FAB-MS(m/e): 361[M+H]$^+$

MANUFACTURING EXAMPLE 44

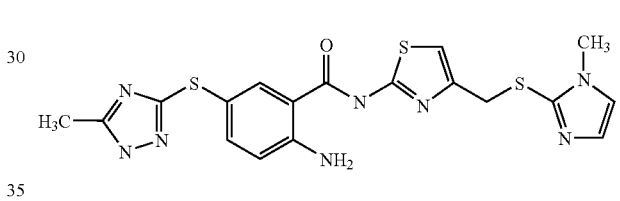

Preparation of 2-amino-5-(5-methyl-4H-[1,2,4]triazol-3-ylsulfanyl)-N-[4-(1-methyl-1H-imidazol-2-ylsulfanylmethyl)thiazol-2-yl]benzamide $^1$HNMR(CD$_3$OD) δ: 2.38 (3H, s), 3.47 (3H, s), 4.10 (2H, s), 6.54 (1H, s), 6.78 (1H, d, J=8.8 Hz), 7.04 (1H, d, J=1.2 Hz), 7.13 (1H, d, J=1.2 Hz), 7.40 (1H, dd, J=2.0 Hz, 8.8 Hz), 7.98 (1H, d, J=2.0 Hz) FAB-MS(m/e): 459[M+H]$^+$

MANUFACTURING EXAMPLE 45

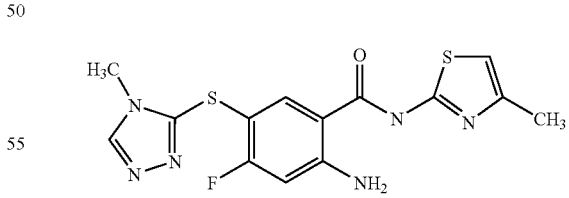

Preparation of 2-amino-4-fluoro-5-(4-methyl-4H-[1,2,4]triazol-3-ylsulfanyl)-N-(4-methylthiazol-2-yl)benzamide $^1$HNMR(CD$_3$OD) δ: 2.32 (3H, s), 3.77 (3H, s), 6.56 (1H, d, J=11.6 Hz), 6.62 (1H, s), 8.13 (1H, d, J=8.0 Hz), 8.51 (1H, s) FAB-MS(m/e): 365[M+H]$^+$

MANUFACTURING EXAMPLE 46

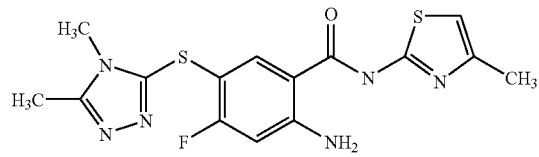

Preparation of 2-amino-4-fluoro-5-(4,5-dimethyl-4H-[1,2,4]triazol-3-ylsulfanyl)-N-(4-methylthiazol-2-yl)benzamide $^1$HNMR(CD$_3$OD) δ: 2.33 (3H, s), 2.43 (3H, s), 3.67 (3H, s), 6.54 (1H, d, J=11.6 Hz), 6.62 (1H, s), 8.11 (1H, d, J=7.6 Hz) FAB-MS(m/e): 379[M+H]$^+$

MANUFACTURING EXAMPLE 47

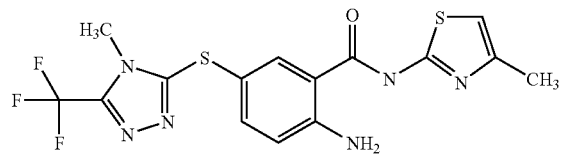

Preparation of 2-amino-5-(4-methyl-5-trifluoromethyl-4H-[1,2,4]triazol-3-ylsulfanyl)-N-(4-methylthiazol-2-yl)benzamide $^1$HNMR(CDCl$_3$) δ: 2.16 (3H, s), 3.68 (3H, s), 6.47 (1H, s), 6.63 (1H, d, J=9.2 Hz), 7.35 (1H, dd, J=1.2 Hz, 9.2 Hz), 7.87 (1H, d, J=1.2 Hz) FAB-MS(m/e): 415[M+H]$^+$

MANUFACTURING EXAMPLE 48

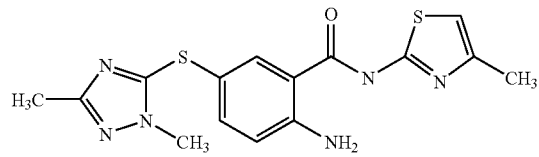

Preparation of 2-amino-5-(2,5-dimethyl-2H-[1,2,4]triazol-3-ylsulfanyl)-N-(4-methylthiazol-2-yl)benzamide $^1$HNMR(CD$_3$OD) δ: 2.25 (3H, s), 2.33 (3H, s), 3.84 (3H, s), 6.64 (1H, s), 6.79 (1H, d, J=8.8 Hz), 7.37 (1H, dd, J=2.0 Hz, 8.8 Hz), 8.00 (1H, d, J=2.0 Hz) FAB-MS(m/e): 361[M+H]$^+$

MANUFACTURING EXAMPLE 49

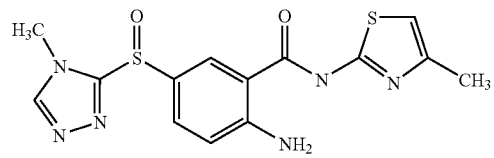

Preparation of 2-amino-5-(4-methyl-4H-[1,2,4]triazol-3-ylsulfinyl)-N-(4-methylthiazol-2-yl)benzamide $^1$HNMR(CD$_3$OD) δ: 2.32 (3H, d, J=0.8 Hz), 3.81 (3H, s), 6.62 (1H, s), 6.95 (1H, d, J=8.9 Hz), 7.54 (1H, dd, J=2.2 Hz, 8.9 Hz), 8.26 (1H, d, J=2.2 Hz), 8.57 (1H, s) FAB-MS(m/e): 363[M+H]$^+$

MANUFACTURING EXAMPLE 50

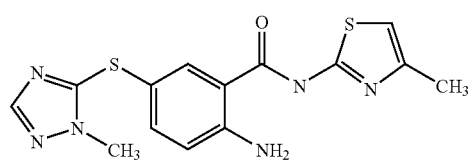

Preparation of 2-amino-5-(2-methyl-2H-[1,2,4]triazol-3-ylsulfanyl)-N-(4-methylthiazol-2-yl)benzamide $^1$HNMR(CDCl$_3$) δ: 2.21 (3H, s), 3.84 (3H, s), 6.01 (2H, br), 6.69 (1H, d, J=8.4 Hz), 7.43 (1H, d, J=8.4 Hz), 7.78 (1H, s), 7.83 (1H, s) FAB-MS(m/e): 347[M+H]$^+$

MANUFACTURING EXAMPLE 51

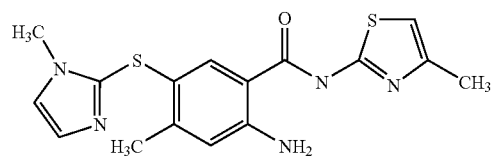

Preparation of 2-amino-4-methyl-5-(1-methyl-1H-imidazol-2-ylsulfanyl)-N-(4-methylthiazol-2yl)benzamide $^1$HNMR(CDCl$_3$) δ: 2.35 (3H, s), 2.38 (3H, s), 3.71 (3H, s), 6.51 (1H, s), 6.56 (1H, s), 6.94 (1H, s), 7.03 (1H, s), 7.93 (1H, s) FAB-MS(m/e): 360[M+H]$^+$

MANUFACTURING EXAMPLE 52

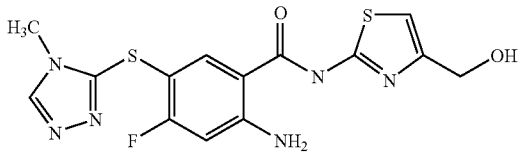

Preparation of 2-amino-4-fluoro-5-(4-methyl-4H-[1,2,4]triazol-3-ylsulfanyl)-N-(4-hydroxymethylthiazol-2-yl)benzamide $^1$HNMR(CD$_3$OD) δ: 3.78 (3H, s), 4.60 (2H, s), 6.58 (1H, d, J$_{H-F}$=11.4 Hz), 6.93 (1H, s), 8.12 (1H, d, J$_{H-F}$=7.7 Hz), 8.52 (1H, s) FAB-MS(m/e): 381[M+H]$^+$

MANUFACTURING EXAMPLE 53

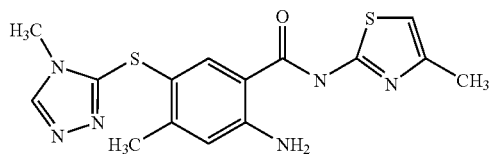

Preparation of 2-amino-4-methyl-5-(4-methyl-4H-[1,2,4]triazol-3-ylsulfanyl)-N-(4-methylthiazol-2-yl)benzamide $^1$HNMR(CD$_3$OD) δ: 2.32 (3H, s), 2.34 (3H, s), 3.71 (3H, s), 6.63 (1H, s), 6.73 (1H, s), 8.02 (1H, s), 8.48 (1H, s) FAB-MS(m/e): 361[M+H]$^+$

MANUFACTURING EXAMPLE 54

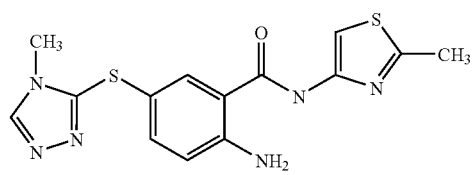

Preparation of 2-amino-5-(4-methyl-4H-[1,2,4]triazol-3-ylsulfanyl)-N-(2-methylthiazol-4-yl)benzamide $^1$HNMR(CD$_3$OD) δ: 2.65 (3H, s), 3.72 (3H, s), 6.77 (1H, d, J=8.8 Hz), 7.36 (1H, dd, J=2.0 Hz, 8.8 Hz), 7.51 (1H, s), 7.89 (1H, d, J=2.0 Hz), 8.52 (1H, s) FAB-MS(m/e): 347 [M+H]$^+$

MANUFACTURING EXAMPLE 55

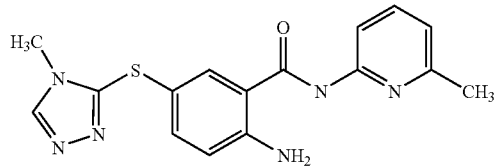

Preparation of 2-amino-5-(4-methyl-4H-[1,2,4]triazol-3-ylsulfanyl)-N-(6-methylpyridin-2-yl)benzamide $^1$HNMR(CD$_3$OD) δ: 2.47 (3H, s), 3.73 (3H, s), 6.78 (1H, d, J=8.7 Hz), 7.01 (1H, d, J=7.7 Hz), 7.36 (1H, dd, J=2.2 Hz, 8.7 Hz), 7.69 (1H, t, J=7.7 Hz), 7.94 (1H, d, J=2.2 Hz), 7.96 (1H, d, J=7.7 Hz), 8.51 (1H, s) FAB-MS(m/e): 341[M+H]$^+$

MANUFACTURING EXAMPLE 56

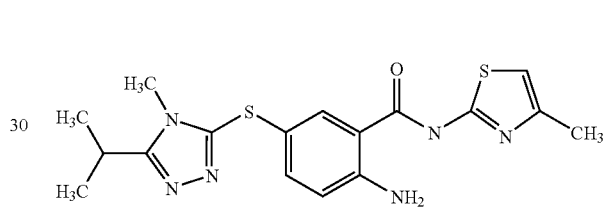

Preparation of 2-amino-5-(5-isopropyl-4-methyl-4H-[1,2,4]triazol-3-ylsulfanyl)-N-(4-methylthiazol-2-yl)benzamide $^1$HNMR(CD$_3$OD) δ: 1.32 (6H, d, J=6.9 Hz), 2.32 (3H, s), 3.09-3.13 (1H, m), 3.65 (3H, s), 6.63 (1H, s), 6.77 (1H, d, J=8.7 Hz), 7.35 (1H, dd, J=2.2 Hz, 8.7 Hz), 7.99 (1H, d, J=2.2 Hz) FAB-MS(m/e): 389[M+H]$^+$

MANUFACTURING EXAMPLE 57

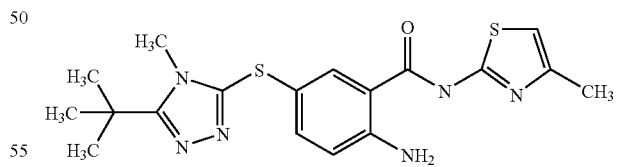

Preparation of 2-amino-4-fluoro-5-(5-tert-butyl-4-methyl-4H-[1,2,4]triazol-3-ylsulfanyl)-N-(4-methylthiazol-2-yl)benzamide $^1$HNMR(CD$_3$OD) δ: 1.43 (9H, s), 2.33 (3H, d, J=1.0 Hz), 3.83 (3H, s), 6.63 (1H, s), 6.78 (1H, d, J=8.7 Hz), 7.35 (1H, dd, J=2.2 Hz, 8.7 Hz), 8.00 (1H, d, J=2.2 Hz) FAB-MS(m/e): 403[M+H]$^+$

MANUFACTURING EXAMPLE 58

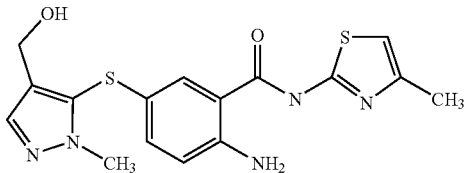

Preparation of 2-amino-5-(5-hydroxymethyl-2-methyl-2H-pyrazol-3-ylsulfanyl)-N-(4-methylthiazol-2-yl)benzamide $^1$HNMR(CD$_3$OD) δ: 2.32 (3H, s), 3.86 (3H, s), 4.61 (2H, s), 6.63 (1H, s), 6.73 (1H, d, J=8.8 Hz), 7.18 (1H, d, J=2.0 Hz, 8.8 Hz), 7.58 (1H, s), 7.81 (1H, d, J=2.0 Hz) FAB-MS (m/e): 376[M+H]$^+$

MANUFACTURING EXAMPLE 59

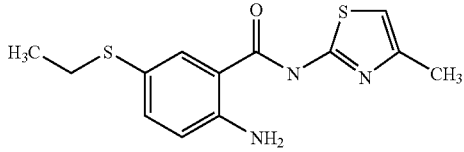

Preparation of 2-amino-5-ethylsulfanyl-N-(4-methylthiazol-2-yl)benzamide $^1$HNMR(CDCl$_3$) δ: 1.18 (3H, t, J=7.2 Hz), 2.20 (3H, s), 2.69 (2H, q, J=7.2 Hz), 6.53 (1H, s), 6.67 (1H, d, J=8.8 Hz), 7.34 (1H, dd, J=2.4 Hz, 8.8 Hz), 7.61 (1H, d, J=2.4 Hz) FAB-MS(m/e): 294[M+H]$^+$

MANUFACTURING EXAMPLE 60

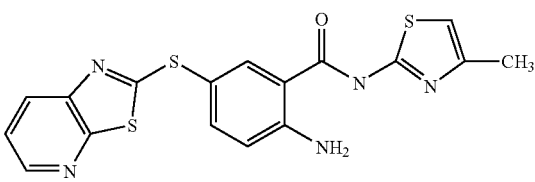

Preparation of 2-amino-5-(thiazolo[5,4-b]pyridin-2-ylsulfanyl)-N-(4-methylthiazol-2-yl)benzamide $^1$HNMR(CD$_3$OD) δ: 2.28 (3H, s), 6.61 (1H, s), 6.93 (1H, d, J=8.8 Hz), 7.44 (1H, dd, J=4.8 Hz, 8.4 Hz), 7.53 (1H, dd, J=2.4 Hz, 8.8 Hz), 8.07 (1H, dd, J=1.6 Hz, 8.4 Hz), 8.19 (1H, d, J=2.4 Hz), 8.37 (1H, dd, J=1.6 Hz, 4.8 Hz) FAB-MS(m/e): 400[M+H]$^+$

MANUFACTURING EXAMPLE 61

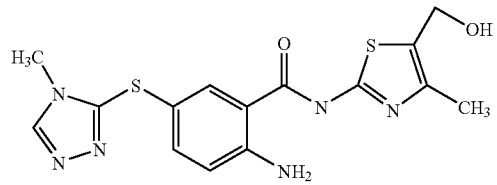

Preparation of 2-amino-5-(4-methyl-4H-[1,2,4]triazol-3-ylsulfanyl)-N-(5-hydroxymethyl-4-methylthiazol-2-yl)benzamide $^1$HNMR(CD$_3$OD) δ: 2.29 (3H, s), 3.71 (3H, s), 4.66 (2H, s), 6.78 (1H, d, J=8.8 Hz), 7.36 (1H, dd, J=1.9 Hz, 8.8 Hz), 8.00 (1H, d, J=1.9 Hz), 8.50 (1H, s) FAB-MS(m/e): 377 [M+H]$^+$

MANUFACTURING EXAMPLE 62

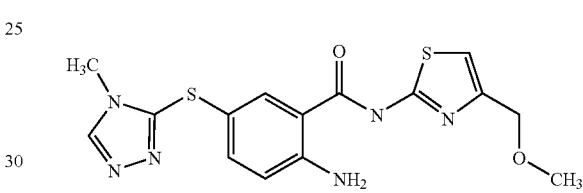

Preparation of 2-amino-5-(4-methyl-4H-[1,2,4]triazol-3-ylsulfanyl)-N-(4-methoxymethylthiazol-2-yl)benzamide $^1$HNMR(CD$_3$OD) δ: 3.40 (3H, s), 3.72 (3H, s), 4.46 (2H, s), 6.80 (1H, d, J=8.8 Hz), 7.00 (1H, s), 7.39 (1H, dd, J=2.0 Hz, 8.8 Hz), 7.99 (1H, d, J=2.0 Hz), 8.51 (1H, s) FAB-MS (m/e): 377[M+H]$^+$

MANUFACTURING EXAMPLE 63

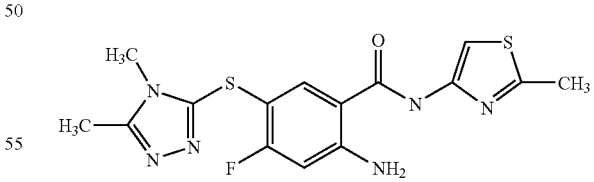

Preparation of 2-amino-5-(4,5-dimethyl-4H-[1,2,4]triazol-3-ylsulfanyl)-N-(2-methylthiazol-4-yl)benzamide $^1$HNMR(CD$_3$OD) δ: 2.42 (3H, s), 2.65 (3H, s), 3.67 (3H, s), 6.53 (1H, d, J=11.2 Hz), 7.49 (1H, s), 7.99 (1H, d, J=7.6 Hz) FAB-MS(m/e): 379[M+H]$^+$

MANUFACTURING EXAMPLE 64

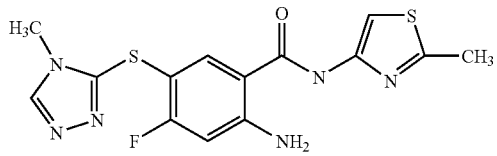

Preparation of 2-amino-4-fluoro-5-(4-methyl-4H-[1,2,4]triazol-3-ylsulfanyl)-N-(2-methylthiazol-4-yl)benzamide $^1$HNMR(CD$_3$OD) δ: 2.65 (3H, s), 3.77 (3H, s), 6.54 (1H, d, J=11.2 Hz), 7.49 (1H, s), 8.00 (1H, d, J=8.0 Hz), 8.49 (1H, s) FAB-MS(m/e): 365[M+H]$^+$

MANUFACTURING EXAMPLE 65

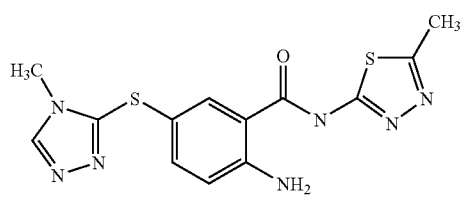

Preparation of 2-amino-5-(4-methyl-4H-[1,2,4]triazol-3-ylsulfanyl)-N-(5-methyl-[1,3,4]thiadiazol-2-yl)benzamide $^1$HNMR(CD$_3$OD) δ: 2.68 (3H, s), 3.71 (3H, s), 6.80 (1H, d, J=8.4 Hz), 7.39 (1H, dd, J=2.0 Hz, 8.4 Hz), 8.06 (1H, d, J=2.0 Hz), 8.51 (1H, s) FAB-MS(m/e): 348[M+H]$^+$

MANUFACTURING EXAMPLE 66

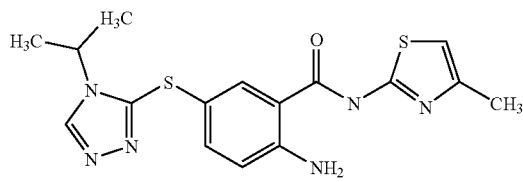

Preparation of 2-amino-5-(4-isopropyl-4H-[1,2,4]triazol-3-ylsulfanyl)-N-(4-methylthiazol-2-yl)benzamide $^1$HNMR(CDCl$_3$) δ: 1.47 (6H, d, J=6.8 Hz), 2.33 (3H, s), 4.62 (1H, sep, J=6.8 Hz), 6.00 (2H, br), 6.55 (1H, s), 6.69 (1H, d, J=8.4 Hz), 7.44 (1H, dd, J=1.6 Hz, 8.4 Hz), 7.96 (1H, d, J=1.6 Hz), 8.26 (1H, s) FAB-MS(m/e): 375[M+H]$^+$

MANUFACTURING EXAMPLE 67

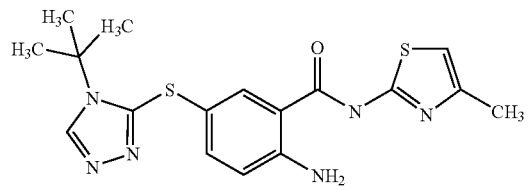

Preparation of 2-amino-5-(4-tert-butyl-4H-[1,2,4]triazol-3-ylsulfanyl)-N-(4-methylthiazol-2-yl)benzamide $^1$HNMR(CDCl$_3$) δ: 1.74 (9H, s), 2.32 (3H, s), 5.98 (2H, br), 6.53 (1H, s), 6.70 (1H, d, J=8.8 Hz), 7.48 (1H, d, J=8.8 Hz), 7.94 (1H, s), 8.22 (1H, s) FAB-MS(m/e): 389[M+H]$^+$

MANUFACTURING EXAMPLE 68

Preparation of 3-amino-6-(1-methyl-1H-imidazol-2-ylsulfanyl)pyridine-2-carboxylic acid thiazol-2-ylamide $^1$HNMR(CDCl$_3$) δ: 3.75 (3H, s), 5.94 (2H, br.s), 6.95-7.05 (3H, m), 7.21 (1H, br.s), 7.28 (1H, br.s), 7.51 (1H, d, J=3.9 Hz) FAB-MS(m/e): 333[M+H]$^+$

MANUFACTURING EXAMPLE 69

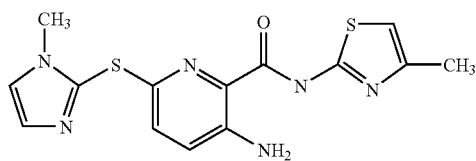

Preparation of 3-amino-6-(1-methyl-1H-imidazol-2-ylsulfanyl)pyridine-2-carboxylic acid 4-methylthiazol-2-ylamide $^1$HNMR(CDCl$_3$) δ: 2.39 (3H, s), 3.73 (3H, s), 5.93 (2H, br.s), 6.56 (1H, s), 6.91-7.00 (2H, m), 7.16 (1H, br.s), 7.24 (1H, br.s) FAB-MS(m/e): 347[M+H]$^+$

MANUFACTURING EXAMPLE 70

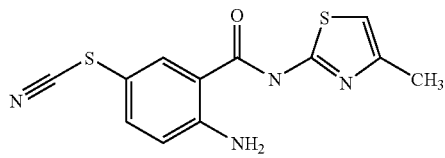

Preparation of 2-amino-5-thiocyanato-N-(4methylthiazol-2-yl)benzamide $^1$HNMR(CD$_3$OD) δ: 2.32 (3H, s), 6.63 (1H, s), 6.87 (1H, d, J=8.8 Hz), 7.47 (1H, dd, J=2.0 Hz, 8.8 Hz), 8.08 (1H, d, J=2.0 Hz) FAB-MS(m/e): 291[M+H]$^+$

MANUFACTURING EXAMPLE 71

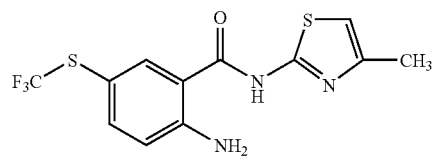

Preparation of 2-amino-5-trifluoromethylsulfanyl-N-(4-methylthiazol-2-yl)benzamide $^1$HNMR(CDCl$_3$) δ: 2.06 (3H, s), 6.58 (1H, s), 7.54 (1H, t, J=8.0 Hz), 7.86 (1H, d, J=8.0 Hz), 7.99 (1H, d, J=8.0 Hz), 8.20 (1H, s) FAB-MS(m/e): 319[M+H]$^+$

MANUFACTURING EXAMPLE 72

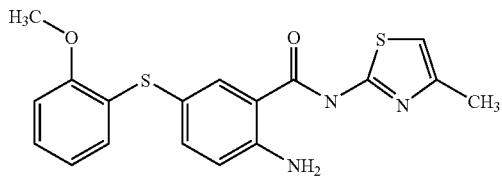

Preparation of 2-amino-5-(2-methoxyphenylsulfanyl)-N-(4-methylthiazol-2-yl)benzamide $^1$HNMR(CDCl$_3$) δ: 2.26-2.33 (3H, m), 3.90 (3H, s), 5.94 (1H, br), 6.52 (1H, d, J=1.0 Hz), 6.72-6.86 (4H, m), 7.09-7.15 (1H, m), 7.41 (1H, dd, J=2.0 Hz, 8.5 Hz), 7.69 (1H, s) FAB-MS(m/e): 372[M+H]$^+$

MANUFACTURING EXAMPLE 73

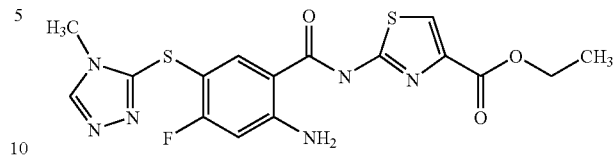

Preparation of 2-amino-4-fluoro-5-(4-methyl-4H-[1,2,4]triazol-3-ylsulfanyl)-N-(4-ethoxycarbonylthiazol-2-yl)benzamide $^1$HNMR(DMSO-d$_6$) δ: 1.31 (3H, t, J=7.0 Hz), 3.64 (3H, s), 4.29 (2H, q, J=7.0 Hz), 6.65 (1H, d, J$_{H-F}$=11.6 Hz), 7.29 (2H, brs), 8.09 (1H, s), 8.34 (1H, s), 8.57 (1H, s) FAB-MS (m/e): 423[M+H]$^+$

MANUFACTURING EXAMPLE 74

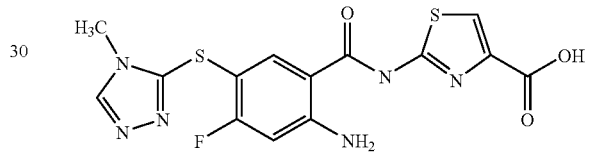

Preparation of 2-amino-4-fluoro-5-(4-methyl-4H-[1,2,4]triazol-3-ylsulfanyl)-N-(4-carboxylthiazol-2-yl)benzamide $^1$HNMR(CDCl$_3$) δ: 3.81 (3H, s), 6.62 (1H, d, J$_{H-F}$=11.0 HZ), 8.00 (1H, 3), 8.21 (1H, d, J$_{H-F}$=4.8 Hz), 8.57 (1H, s) FAB-MS(m/e): 395[M+H]$^+$

MANUFACTURING EXAMPLE 75

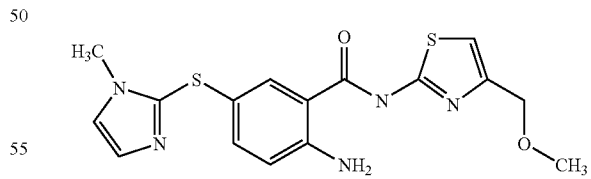

Preparation of 2-amino-5-(1-methyl-1H-imidazol-2-ylsulfanyl)-N-(4-methylthiazol-2-yl)benzamide $^1$HNMR(CDCl$_3$) δ: 3.45 (3H, s), 3.70 (3H, s), 4.47 (2H, s), 5.82-5.86 (2H, brs), 6.64 (1H, d, J=8.8 Hz), 6.87 (1H, s), 6.96 (1H, s), 7.06 (1H, s), 7.37 (1H, dd, J=1.6 Hz, 8.8 Hz), 7.88 (1H, d, J=1.6 Hz) FAB-MS(m/e): 376[M+H]$^+$

MANUFACTURING EXAMPLE 76

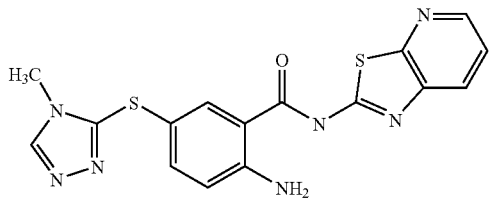

Preparation of 2-amino-5-(4-methyl-4H-[1,2,4]triazol-3-ylsulfanyl)-N-thiazolo[5,4-b]pyridin-2-ylbenzamide $^1$HNMR(DMSO-d$_6$) δ: 3.59 (3H, s), 6.80 (1H, d, J=8.8 Hz), 7.30 (1H, d, J=8.8 Hz), 7.47 (1H, br), 8.07 (1H, br), 8.16 (1H, s), 8.44 (1H, d, J=4.8 Hz), 8.57 (1H, s) FAB-MS (m/e): 384[M+H]$^+$

MANUFACTURING EXAMPLE 77

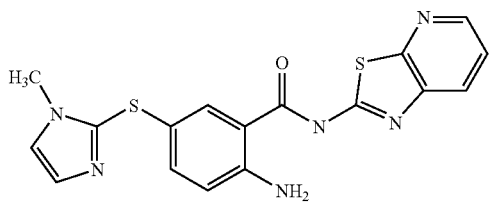

Preparation of 2-amino-5-(1-methyl-1H-imidazol-2-ylsulfanyl)-N-thiazolo[5,4-b]pyridin-2-ylbenzamide $^1$HNMR(CD$_3$OD) δ: 6.79 (1H, d, J=8.8 Hz), 7.07 (1H, br), 7.24 (1H, br), 7.32 (1H, dd, J=2.0 Hz, 8.8 Hz), 7.49 (1H, dt, J=4.8 Hz, 8.0 Hz), 8.02 (1H, d, J=2.0 Hz), 8.10 (1H, d, J=8.0 Hz), 8.43 (1H, d, J=4.8 Hz) FAB-MS(m/e): 383[M+H]$^+$

MANUFACTURING EXAMPLE 78

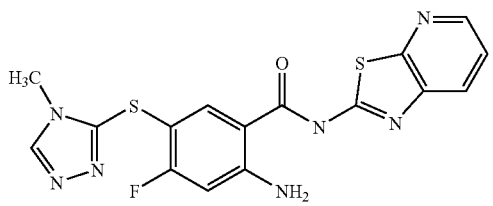

Preparation of 2-amino-4-fluoro-5-(4-methyl-4H-[1,2,4]triazol-3-ylsulfanyl)-N-thiazolo[5,4-b]pyridin-2-ylbenzamide $^1$HNMR(DMSO-d$_6$) δ: 3.62 (3H, s), 6.64 (1H, d, J=12.0 Hz), 7.47 (1H, br), 8.05 (1H, br), 8.33 (1H, d, J=8.7 Hz), 8.44 (1H, br), 8.55 (1H, s) FAB-MS(m/e): 402[M+H]$^+$

MANUFACTURING EXAMPLE 79

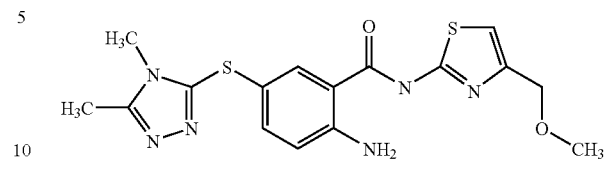

Preparation of 2-amino-5-(4,5-dimethyl-4H-[1,2,4]triazol-3-ylsulfanyl)-N-(4-methoxymethylthiazol-2-yl)benzamide $^1$HNMR(CD$_3$OD) δ: 2.41 (3H, s), 3.39 (3H, s), 3.61 (3H, s), 4.45 (2H, s), 6.77 (1H, d, J=8.8 Hz), 6.98 (1H, s), 7.36 (1H, dd, J=2.4 Hz, 8.8 Hz), 7.97 (1H, d, J=2.4 Hz) FAB-MS(m/e): 391[M+H]$^+$

MANUFACTURING EXAMPLE 80

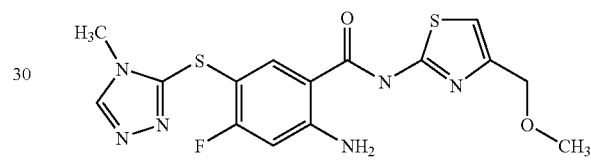

Preparation of 2-amino-4-fluoro-5-(4,5-dimethyl-4H-[1,2,4]triazol-3-ylsulfanyl)-N-(4-methoxymethylthiazol-2-yl)benzamide $^1$HNMR(DMSO-d$_6$) δ: 3.14 (3H, s), 3.60 (3H, s), 4.38 (2H, s), 6.61 (1H, d, J=12 Hz), 7.06 (1H, s), 7.18-7.30 (2H, brs), 8.24 (1H, d, J=8.0 Hz), 8.54 (1H, s) FAB-MS(m/e): 395[M+H]$^+$

MANUFACTURING EXAMPLE 81

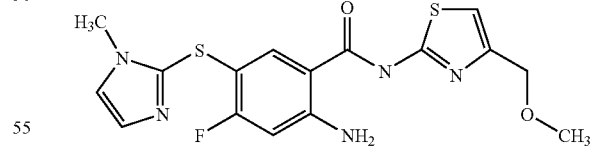

Preparation of 2-amino-4-fluoro-5-(1-methyl-1H-imidazol-2-ylsulfanyl)-N-(4-methoxymethylthiazol-2-yl)benzamide $^1$HNMR(CDCl$_3$) δ: 3.42 (3H, s), 3.76 (3H, s), 4.44 (2H, s), 6.08-6.18 (2H, brs), 6.35 (1H, d, J=10.4 Hz), 6.84 (1H, s), 6.93 (1H, s), 7.02 (1H, s), 8.05 (1H, d, J=7.6 Hz) FAB-MS(m/e): 394[M+H]$^+$

MANUFACTURING EXAMPLE 82

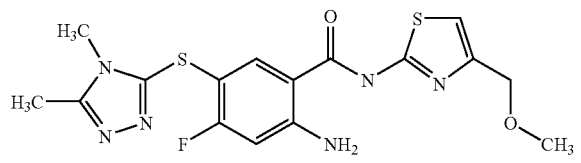

Preparation of 2-amino-4-fluoro-5-(4,5-dimethyl-4H-[1,2,4]triazol-3-ylsulfanyl)-N-(4-methoxymethylthiazol-2-yl)benzamide $^1$HNMR(CDCl$_3$) δ: 2.40 (3H, s), 3.40 (3H, s), 3.59 (3H, s), 4.41 (2H, s), 6.20-6.28 (2H, brs), 6.30 (1H, d, J=10.8 Hz), 6.80 (1H, s), 8.10 (1H, d, J=7.6 Hz) FAB-MS(m/e): 409 [M+H]$^+$

MANUFACTURING EXAMPLE 83

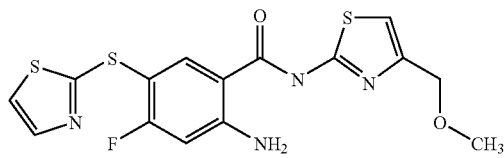

Preparation of 2-amino-5-(thiazol-2-ylsulfanyl)-N-(4-methoxymethylthiazol-2-yl)benzamide $^1$HNMR(CDCl$_3$) δ: 3.43 (3H, s), 4.45 (2H, s), 6.24-6.30 (2H, brs), 6.51 (1H, d, J=10.8 Hz), 6.88 (1H, s), 7.19 (1H, d, J=2.0 Hz), 7.65 (1H, d, J=2.0 Hz), 7.92 (1H, d, J=6.8 Hz) FAB-MS(m/e): 397[M+H]$^+$

MANUFACTURING EXAMPLE 84

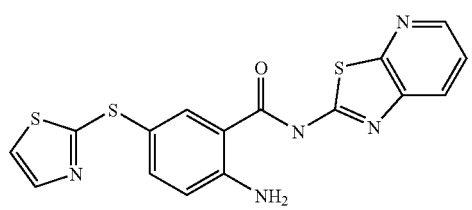

Preparation of 2-amino-5-(thiazol-2-ylsulfanyl)-N-thiazolo[5,4-b]pyridin-2-ylbenzamide $^1$HNMR(CD$_3$OD) δ: 6.92 (1H, d, J=8.4 Hz), 7.40 (1H, d, J=3.6 Hz), 7.45-7.49 (1H, m), 7.53 (1H, d, J=8.4 Hz), 7.63 (1H, d, J=3.6 Hz), 8.08 (1H, d, J=8.0 Hz), 8.22 (1H, s), 8.43 (1H, d, J=4.8 Hz) FAB-MS(m/e): 386[M+H]$^+$

MANUFACTURING EXAMPLE 85

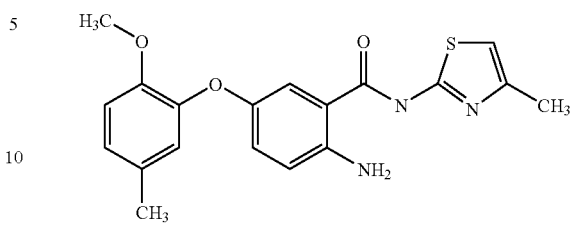

Preparation of 2-amino-5-(2-methoxy-5-methylphenoxy)-N-(4-methoxymethylthiazol-2-yl)benzamide Three drops of N,N-dimethylformamide and 4.07 ml (46.6 mmol) of oxalyl chloride were dripped into a methylene chloride solution (100 ml) of 7.84 g (42.4 mmol) of 5-fluoro-2-nitrobenzoic acid on ice, and after the addition was completed, the reaction mixture was stirred at room temperature for 1 hour. The reaction mixture was concentrated under reduced pressure, and an acid chloride was obtained as a colorless oily material.

7.00 ml (50.8 mmol) of triethylamine was added to a methylene chloride solution (50 ml) of 5.80 g (50.8 mmol) of 2-aminothiazole, the methylene chloride solution (30 ml) of the acid chloride previously obtained was dripped in on ice, and after the addition was completed, the reaction mixture was stirred at room temperature overnight. An aqueous solution of 1 N hydrochloric acid was added to the reaction mixture, the mixture was extracted with chloroform, and then the organic layer was washed with water, an aqueous solution of saturated sodium bicarbonate and saturated brine solution, dried, and concentrated under reduced pressure. The obtained residue was purified by silica gel column chromatography (hexane:ethyl acetate=2:1) to obtain 7.20 g of an amide as a light yellow solid (yield: 60%).

982 mg (7.11 mmol) of potassium carbonate and 982 mg (7.11 mmol) of 2-methoxy-5-methylphenol were added to a N,N-dimethylformamide solution (10 ml) of 200 mg (0.71 mmol) of the obtained amide, and the reaction mixture was stirred at 100° C. for 12 hours. The reaction mixture was concentrated under reduced pressure, and the obtained residue was purified by silica gel column chromatography (hexane:ethyl acetate=2:1) to obtain 278 mg of a nitro compound as a yellow solid (yield: 98%).

2.0 g of iron powder was added to a mixture of an isopropanol solution (5 ml) of 247 mg (0.62 mmol) of the obtained nitro compound and an aqueous solution of saturated ammonium chloride (0.5 ml), and heated under reflux for 30 minutes. After cerite filtration, the reaction mixture was concentrated under reduced pressure, ethyl acetate and water were added to the residue, the organic layer was washed with water and saturated brine solution, dried, and concentrated under reduced pressure. The obtained residue was purified by silica gel column chromatography (hexane:ethyl acetate=2:1) to obtain 191 mg of the title compound as light yellow solids (yield: 84%).

$^1$HNMR(CDCl$_3$) δ: 2.24 (3H, s), 2.32 (3H, s), 3.84 (3H, s), 5.46 (1H, br), 6.52 (1H, d, J=1.0 Hz), 6.66 (1H, s), 6.74 (1H, d, J=8.9 Hz), 6.88 (2H, s), 7.06 (1H, dd, J=2.6 Hz, 8.9 Hz), 7.11 (1H, d, J=2.6 Hz)

ESI-MS(m/e): 370[M+H]$^+$

The compounds of Manufacturing Examples 84 to 117 were obtained as in Manufacturing Example 83.

MANUFACTURING EXAMPLE 86

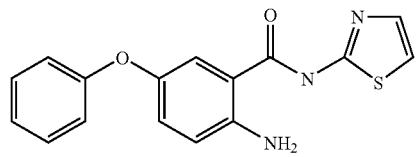

Preparation of
2-amino-5-phenoxy-N-thiazol-2-ylbenzamide $^1$HNMR(CDCl$_3$) δ: 5.53 (2H, br), 6.76 (1H, d, J=8.9 Hz), 6.83-6.87 (3H, m), 7.01 (1H, t, J=7.3 Hz), 7.08 (1H, dd, J=2.3 Hz, 8.9 Hz), 7.25-7.29 (3H, m), 7.32 (1H, d, J=2.3 Hz), 11.61 (1H, br) FAB-MS(m/e): 312[M+H]$^+$

MANUFACTURING EXAMPLE 87

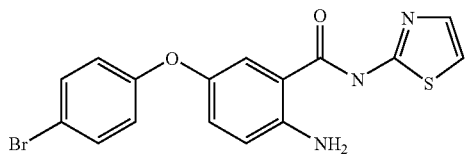

Preparation of
2-amino-5-(4-bromophenoxy)-N-thiazol-2-ylbenzamide $^1$HNMR(CDCl$_3$) δ: 5.60 (2H, br), 6.75-6.82 (3H, m), 6.96 (1H, d, J=2.6 Hz), 7.06 (1H, dd, J=2.6 Hz, 8.3 Hz), 7.37-7.84 (4H, m) FAB-MS(m/e): 392[M+H]$^+$

MANUFACTURING EXAMPLE 88

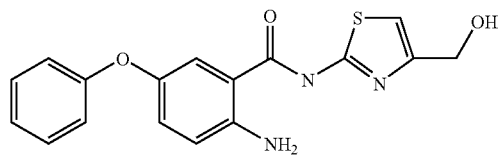

Preparation of 2-amino-5-phenoxy-N-(4-hydroxymethylthiazol-2-yl)benzamide $^1$HNMR(CDCl$_3$) δ: 4.38 (2H, d, J=5.2 Hz), 5.14 (1H, t, J=5.2 Hz), 5.53 (2H, br), 6.76 (1H, d, J=8.9 Hz), 6.83-6.87 (2H, m), 7.01 (1H, t, J=7.3 Hz), 7.08 (1H, dd, J=2.3 Hz, 8.9 Hz), 7.25-7.29 (3H, m), 7.32 (1H, d, J=2.3 Hz), 11.61 (1H, br) FAB-MS(m/e): 342[M+H]$^+$

MANUFACTURING EXAMPLE 89

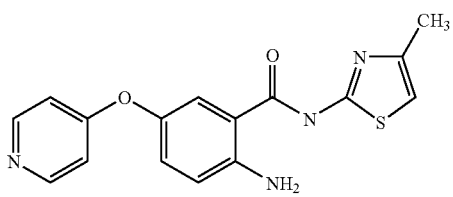

Preparation of 2-amino-5-(pyridin-4-yloxy)-N-(4-methylthiazol-2-yl)benzamide $^1$HNMR(CD$_3$OD) δ: 2.32 (3H, d, J=1.0 Hz), 6.44 (1H, s), 6.55 (2H, d, J=7.6 Hz), 6.92 (1H, d, J=8.9 Hz), 7.38 (1H, dd, J=2.7 Hz, 8.9 Hz), 7.87 (1H, d, J=2.7 Hz), 8.03 (1H, d, J=7.6 Hz) FAB-MS(m/e): 327[M+H]$^+$

MANUFACTURING EXAMPLE 90

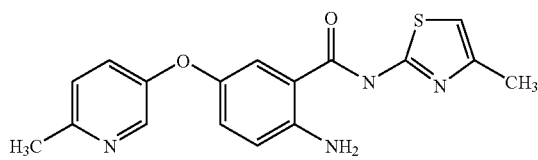

Preparation of 2-amino-5-(2-methylpyridin-5-yloxy)-N-(4-methylthiazol-2-yl)benzamide $^1$HNMR(CD$_3$OD) δ: 2.29 (3H, d, J=1.0 Hz), 2.47 (3H, s), 6.62 (1H, d, J=1.0 Hz), 6.85 (1H, d, J=8.9 Hz), 7.04 (1H, dd, J=2.7 Hz, 8.9 Hz), 7.21-7.28 (2H, m), 7.48 (1H, d, J=2.7 Hz), 8.10 (1H, d, J=2.6 Hz) FAB-MS(m/e): 341[M+H]$^+$

MANUFACTURING EXAMPLE 91

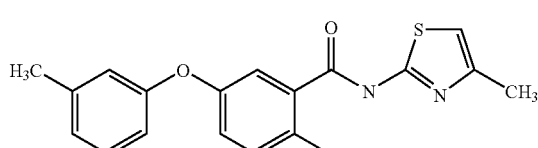

Preparation of 2-amino-5-(3-methylphenoxy)-N-(4-methylthiazol-2-yl)benzamide $^1$HNMR(CDCl$_3$) δ: 2.32 (6H, s), 6.53 (3H, d, J=1.0 Hz), 6.71-6.77 (3H, m), 6.86-6.89 (1H, m), 7.08 (1H, dd, J=2.7 Hz, 8.9 Hz), 7.16-7.21 (2H, m) FAB-MS(m/e): 340[M+H]$^+$

MANUFACTURING EXAMPLE 92

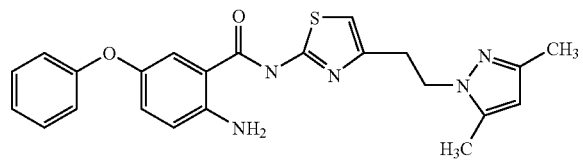

Preparation of 2-amino-5-phenoxy-N-{4-[2-(3,5dimethylpyrazol-1-yl)ethyl]thiazol-2-yl}benzamide $^1$HNMR(CDCl$_3$) δ: 1.99 (3H, s), 2.22 (3H, s), 3.09 (2H, m), 4.21 (2H, m), 5.70 (1H, s), 6.43 (1H, s), 6.76 (1H, d, J=9.0 Hz), 6.92 (1H, br.d, J=7.5 Hz), 7.08 (2H, m), 7.22 (1H, br.s), 7.25-7.38 (2H, m) FAB-MS(m/e): 434[M+H]$^+$

MANUFACTURING EXAMPLE 93

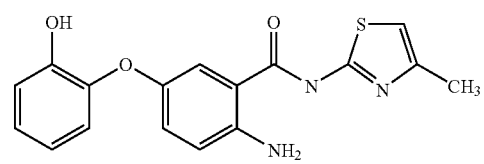

Preparation of 2-amino-5-(4-fluorophenoxy)-N-(4-methylthiazol-2-yl)benzamide $^1$HNMR(CDCl$_3$) δ: 2.14 (3H, s), 5.53 (2H, s), 6.51 (1H, s), 6.75 (1H, d, J=9.2 Hz), 6.78-6.83 (2H, m), 6.93-6.97 (2H, m), 7.03-7.06 (2H, m) FAB-MS(m/e): 344[M+H]$^+$

MANUFACTURING EXAMPLE 94

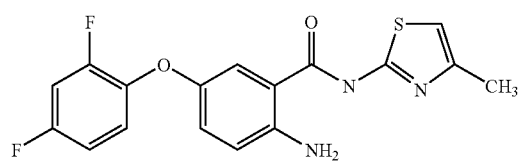

Preparation of 2-amino-3,5-diphenoxy-N-(4-methylthiazol-2-yl)benzamide $^1$HNMR(CDCl$_3$) δ: 2.31 (3H, d, J=0.9 Hz), 6.53 (1H, d, J=0.9 Hz), 6.76 (1H, d, J=2.4 Hz), 6.88 (2H, dd, J=1.0 Hz, 7.7 Hz), 6.91-7.38 (9H, m) FAB-MS(m/e): 418[M+H]$^+$

MANUFACTURING EXAMPLE 95

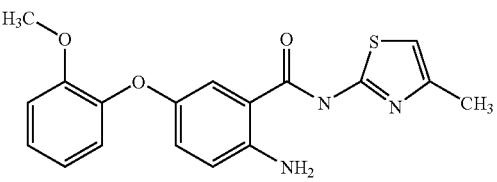

Preparation of 2-amino-5-(2-methoxyphenoxy)-N-(4-methylthiazol-2-yl)benzamide $^1$HNMR(CDCl$_3$) δ: 2.25-2.27 (3H, m), 3.86 (3H, s), 6.51 (1H, s), 6.73 (1H, d, J=9.2 Hz), 6.80-6.90 (2H, m), 7.04-7.10 (4H, m) FAB-MS(m/e): 356[M+H]$^+$

MANUFACTURING EXAMPLE 96

Preparation of 2-amino-5-(2-hydroxyphenoxy)-N-(4-methylthiazol-2-yl)benzamide $^1$HNMR(CDCl$_3$) δ: 2.27 (3H, s), 5.53 (1H, br), 6.52 (1H, s), 6.18-6.21 (3H, m), 6.94-7.06 (3H, m), 7.14 (1H, s) FAB-MS(m/e): 342[M+H]$^+$

MANUFACTURING EXAMPLE 97

Preparation of 2-amino-5-(2,4-difluorophenoxy)-N-(4-methylthiazol-2-yl)benzamide $^1$HNMR(CDCl$_3$) δ: 2.15 (3H, s), 5.51 (1H, br), 6.51 (1H, d, J=1.0 Hz), 6.71-6.93 (4H, m), 7.00-7.09 (2H, m) FAB-MS(m/e): 362[M+H]$^+$

MANUFACTURING EXAMPLE 98

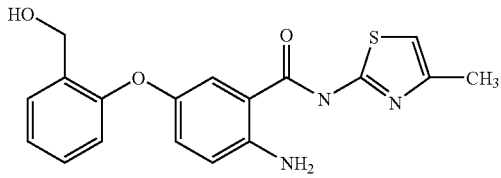

Preparation of 2-amino-5-(2-hydroxymethylphenoxy)-N-(4-methylthiazol-2-yl)benzamide $^1$HNMR(CDCl$_3$) δ: 2.20 (3H, d, J=1.0 Hz), 4.73 (2H, s), 6.49 (1H, d, J=1.0 Hz), 6.67 (1H, dd, J=1.1 Hz, 8.1 Hz), 6.72 (1H, d, J=8.9 Hz), 7.01-7.16 (3H, m), 7.10 (1H, d, J=2.6 Hz), 7.39 (1H, dd, J=1.6 Hz, 7.5 Hz) FAB-MS(m/e): 356[M+H]$^+$

MANUFACTURING EXAMPLE 99

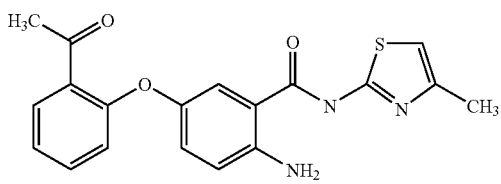

Preparation of 2-amino-5-(2-acetylphenoxy)-N-(4-methylthiazol-2-yl)benzamide $^1$HNMR(CDCl$_3$) δ: 2.16 (3H, s), 2.61 (3H)s), 5.63 (2H, brs), 6.50 (1H, s), 6.72 (1H, d, J=8.4 Hz), 6.78 (1H, d, J=8.4 Hz), 7.04-7.11 (2H, m), 7.20 (1H, s), 7.27-7.37 (1H, m), 7.79 (1H, dd, J=7.7 Hz, 1.8 Hz) FAB-MS(m/e): 368[M+H]$^+$

MANUFACTURING EXAMPLE 100

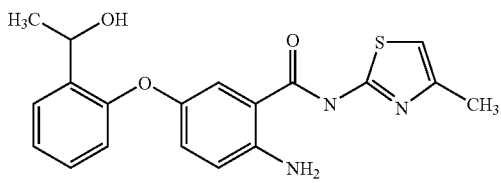

Preparation of 2-amino-5-[2-(1-hydroxyethyl)phenoxy]-N-(4-methylthiazol-2-yl)benzamide $^1$HNMR(CDCl$_3$) δ: 1.56 (3H, d, J=6.6 Hz), 2.27 (3H, s), 4.59 (2H, brs), 5.21 (1H, q, J=6.6 Hz), 6.52 (1H, s), 6.71 (1H, d, J=8.6 Hz), 6.75 (1H, d, J=8.6 Hz), 7.04-7.11 (2H, m), 7.14-7.18 (1H, m), 7.21 (1H, d, J=2.9 Hz), 7.50 (1H, d, J=7.3 Hz) FAB-MS(m/e): 370[M+H]$^+$

MANUFACTURING EXAMPLE 101

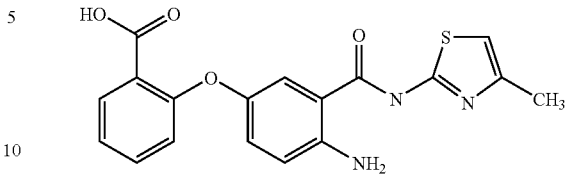

Preparation of 2-amino-5-(2-carboxyphenoxy)-N-(4-methylthiazol-2-yl)benzamide $^1$HNMR(DMSO-d$_6$) δ: 2.25 (3H, s), 6.73 (1H, s), 6.81 (1H, d, J=8.9 Hz), 6.82 (1H, d, J=7.6 Hz), 7.00 (1H, dd, J=2.6 Hz, 8.9 Hz), 7.07-7.12 (1H, m), 7.39-7.42 (1H, m), 7.62 (1H, d, J=2.6 Hz), 7.71 (1H, d, J=7.6 Hz) FAB-MS(m/e): 370[M+H]$^+$

MANUFACTURING EXAMPLE 102

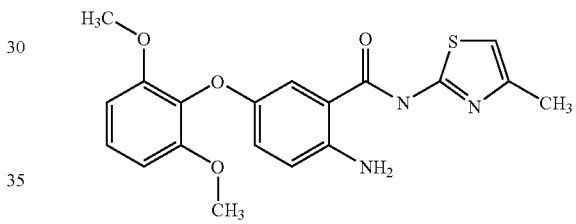

Preparation of 2-amino-5-(2,6-dimethoxyphenoxy)-N-(4-methylthiazol-2-yl)benzamide $^1$HNMR(CDCl$_3$) δ: 2.33 (3H, d, J=1.1 Hz), 3.80 (6H, s), 6.52 (1H, d, J=1.0 Hz), 6.65-6.71 (3H, m), 6.98-7.02 (2H, m), 7.11-7.18 (1H, m) FAB-MS(m/e): 386[M+H]$^+$

MANUFACTURING EXAMPLE 103

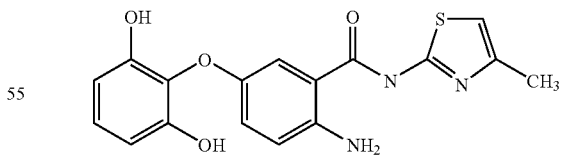

Preparation of 2-amino-5-(2,6-dihydroxyphenoxy)-N-(4-methylthiazol-2-yl)benzamide $^1$HNMR(CDCl$_3$) δ: 2.30 (3H, s), 6.47-6.50 (1H, m), 6.49 (1H, s), 6.54-6.58 (3H, m), 6.94-7.03 (2H, m) FAB-MS(m/e): 358[M+H]$^+$

MANUFACTURING EXAMPLE 104

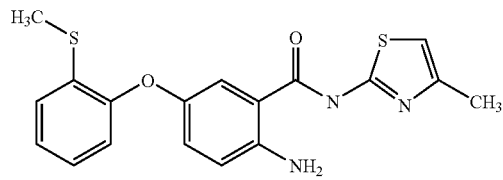

Preparation of 2-amino-5-(2-methylsulfanylphenoxy)-N-(4-methylthiazol-2-yl)benzamide $^1$HNMR(CDCl$_3$) δ: 2.26 (3H, d, J=1.0 Hz), 2.46 (3H, s), 6.51 (1H, d, J=1.0 Hz), 6.74 (1H, d, J=9.4 Hz), 6.75 (1H, d, J=9.2 Hz), 7.05-7.11 (4H, m), 7.23-7.26 (1H, m) FAB-MS (m/e): 372[M+H]$^+$

MANUFACTURING EXAMPLE 105

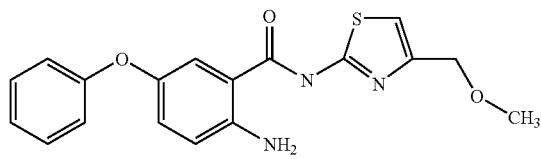

Preparation of 2-amino-5-phenoxy-N-(4-methoxymethylthiazol-2-yl)benzamide $^1$HNMR(CDCl$_3$) δ: 3.34 (3H, s), 4.24 (2H, s), 5.50-5.70 (2H, brs), 6.75 (1H, d, J=8.4 Hz), 6.84 (2H, d, J=7.6 Hz), 7.01 (1H, t, J=7.6 Hz), 7.06-7.09 (2H, m), 7.25 (2H, t, J=7.6 Hz), 10.4-10.5 (1H, brs) FAB-MS(m/e): 356[M+H]$^+$

MANUFACTURING EXAMPLE 106

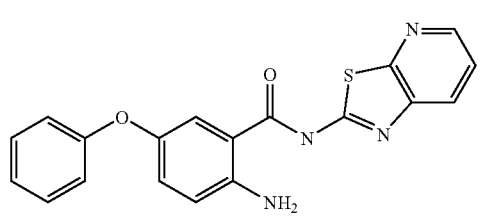

Preparation of 2-amino-5-phenoxy-N-thiazolo[5,4-b]pyridin-2-ylbenzamide $^1$HNMR(CDCl$_3$) δ: 6.79 (1H, d, J=8.8 Hz), 6.83 (2H, d, J=8.8 Hz), 7.04 (1H, t, J=8.8 Hz), 7.10 (1H, dd, J=2.4 Hz, 8.8 Hz), 7.26-7.30 (3H, m), 7.31 (1H, dt, J=4.8 Hz, 8.0 Hz), 7.76 (1H, d, J=8.0 Hz), 8.49 (1H, d, J=4.8 Hz) FAB-MS(m/e): 363[M+H]$^+$

MANUFACTURING EXAMPLE 107

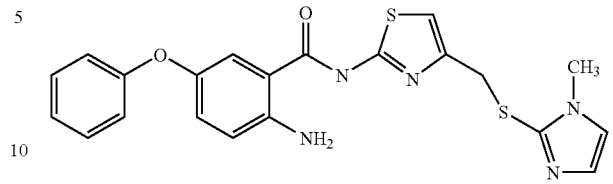

Preparation of 2-amino-5-phenoxy-N-[4-(1-methyl-1H-imidazol-2-ylsulfanymethyl)thiazol-2-yl]benzamide $^1$HNMR(CDCl$_3$) δ: 3.40 (3H, s), 4.15 (2H, s), 6.55 (1H, s), 6.75 (1H, d, J=8.8 Hz), 6.87 (1H, s), 6.91 (2H, d, J=7.2 Hz), 7.03-7.11 (3H, m), 7.25 (1H, dd, J=2.8 Hz, 8.8 Hz), 7.30 (2H, t, J=7.2 Hz) FAB-MS(m/e): 438[M+H]$^+$

MANUFACTURING EXAMPLE 108

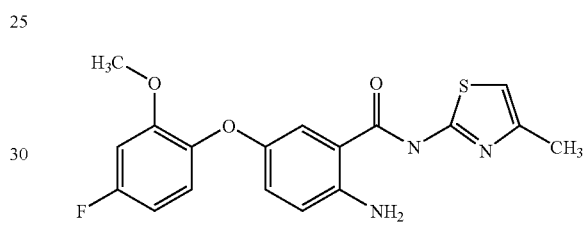

Preparation of 2-amino-5-(4-fluoro-2-methoxyphenoxy)-N-(4-methylthiazol-2-yl)benzamide $^1$HNMR(CDCl$_3$) δ: 2.31 (3H, d, J=1.0 Hz), 3.84 (3H, s), 6.53 (1H, d, J=1.0 Hz), 6.56-6.63 (1H, m), 6.73 (1H, d, J=8.8 Hz), 6.74 (1H, d, J=10.0 Hz), 6.84 (1H, dd, J=5.7 Hz, 8.8 Hz), 7.03 (1H, dd, J=2.6 Hz, 8.8 Hz), 7.06 (1H, d, J=2.6 Hz) FAB-MS(m/e): 374[M+H]$^+$

MANUFACTURING EXAMPLE 109

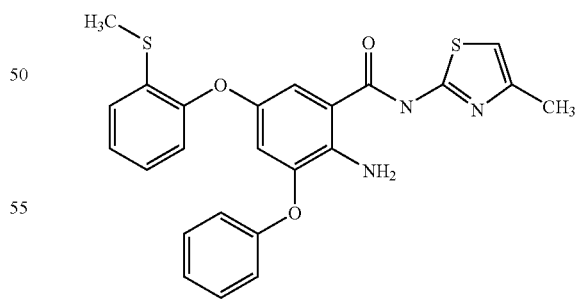

Preparation of 2-amino-3-phenoxy-5-(2-methylsulfanylphenoxy)-N-(4-methylthiazol-2-yl)benzamide $^1$HNMR(CDCl$_3$) δ: 2.27 (3H, s), 2.43 (3H, s), 6.53 (1H, s), 6.72-6.75 (1H, m), 6.77 (1H, d, J=2.5 Hz), 6.90 (1H, d, J=2.5 Hz), 7.03-7.07 (4H, m), 7.11-7.23 (2H, m), 7.33-7.38 (2H, m) FAB-MS(m/e): 464[M+H]$^+$

MANUFACTURING EXAMPLE 110

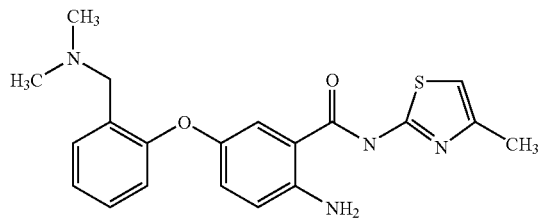

Preparation of 2-amino-5-(2-N,N-dimethylaminomethylphenoxy)-N-(4-methylthiazol-2-yl) benzamide $^1$HNMR(CD$_3$OD) δ: 2.30 (3H, s), 2.56 (6H, s), 3.97 (2H, s), 6.63 (1H, s), 6.79-6.88 (2H, m), 7.02-7.11 (2H, m), 7.26-7.32 (1H, m), 7.43 (1H, d, J=7.5 Hz), 7.48 (1H, s) FAB-MS(m/e): 383[M+H]$^+$

MANUFACTURING EXAMPLE 111

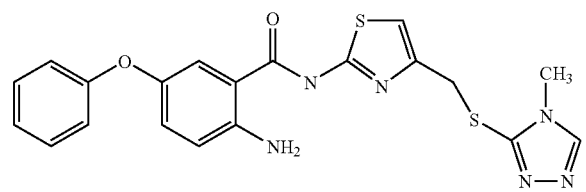

Preparation of 2-amino-5-phenoxy-N-[4-(4-methyl-4H-[1,2,4]triazol-2-ylsulfanymethyl)thiazol-2-yl] benzamide $^1$HNMR(CDCl$_3$) δ: 3.45 (3H, s), 4.39 (2H, s), 5.50-5.70 (2H, brs), 6.76 (1H, d, J=8.8 Hz), 6.82 (1H, s), 6.92 (2H, d, J=7.6 Hz), 7.06-7.11 (2H, m), 7.20 (1H, d, J=2.4 Hz), 7.31 (2H, t, J=7.6 Hz), 8.09 (1H, s), 9.70-9.90 (1H, brs) FAB-MS(m/e): 439[M+H]$^+$

MANUFACTURING EXAMPLE 112

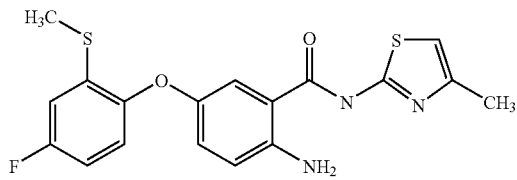

Preparation of 2-amino-5-(4-fluoro-2-methylsulfanylphenoxy)-N-(4-methylthiazol-2-yl)benzamide $^1$HNMR(CDCl$_3$) δ: 2.18-2.23 (3H, m), 2.42 (3H, s), 6.51 (1H, d, J=0.9 Hz), 6.68-6.77 (3H, m), 6.84-6.93 (1H, m), 7.04 (1H, dd, J=2.2 Hz, 8.6 Hz), 7.10 (1H, d, J=2.2 Hz) FAB-MS(m/e): 390[M+H]$^+$

MANUFACTURING EXAMPLE 113

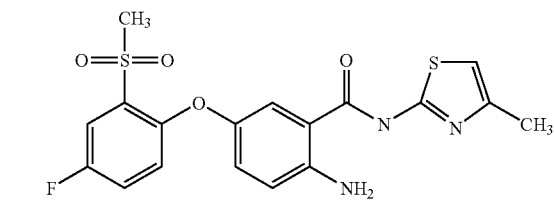

Preparation of 2-amino-5-(4-fluoro-2-methylsulfonylphenoxy)-N-(4-methylthiazol-2-yl)benzamide $^1$HNMR(CDCl$_3$) δ: 2.18 (3H, s), 3.27 (3H, s), 5.69 (1H, br), 6.50 (1H, s), 6.75 (1H, d, J=8.9 Hz), 6.81 (1H, dd, J=4.0 Hz, 8.9 Hz), 7.06 (1H, dd, J=2.4 Hz, 8.9 Hz), 7.13-7.22 (1H, m), 7.31 (1H, d, J=2.4 Hz), 7.73 (1H, dd, J=3.0 Hz, 7.3 Hz) FAB-MS (m/e): 422 [M+H]$^+$

MANUFACTURING EXAMPLE 114

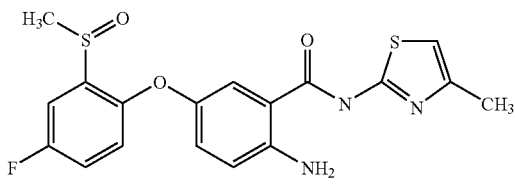

Preparation of 2-amino-5-(4-fluoro-2-methylsulfinylphenoxy)-N-(4-methylthiazol-2-yl) benzamide $^1$HNMR (CDCl$_3$) δ: 2.28-2.34 (3H, m), 2.67 (3H, s), 6.54 (1H, s), 6.68-6.80 (2H, m), 7.01-7.09 (2H, m), 7.28 (1H, d, J=2.7 Hz), 7.63-7.70 (1H, m) FAB-MS(m/e): 406[M+H]$^+$

MANUFACTURING EXAMPLE 115

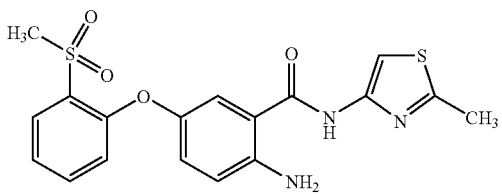

Preparation of 2-amino-5-(2-methylsulfonylphenoxy)-N-(2-methylthiazol-4-yl)benzamide $^1$HNMR(CDCl$_3$) δ: 2.62 (3H, s), 3.33 (3H, s), 5.60 (2H, brs), 6.77 (1H, d, J=8.8 Hz), 6.85 (1H, d, J=8.1 Hz), 7.09 (1H, dd, J=8.8 Hz, 2.6 Hz), 7.20 (1H, d, J=7.7 Hz, 7.7 Hz), 7.31 (1H, d, J=2.6 Hz), 7.50 (1H, ddd, J=8.1 Hz, 7.7 Hz, 1.6 Hz), 7.53 (1H, s), 8.05 (1H, dd, J=7.7 Hz, 1.6 Hz), 8.86 (1H, brs) FAB-MS(m/e): 404[M+H]$^+$

MANUFACTURING EXAMPLE 116

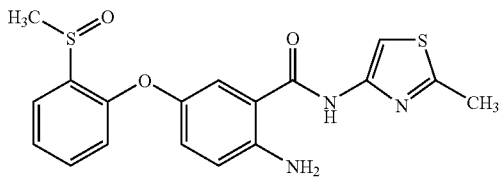

Preparation of 2-amino-5-(2-methylsulfinylphenoxy)-N-(2-methylthiazol-4-yl)benzamide $^1$HNMR(CDCl$_3$) δ: 2.64 (3H, s), 2.90 (3H, s), 5.57 (2H, brs), 6.71 (1H, d, J=8.1 Hz), 6.76 (1H, d, J=8.8 Hz), 7.02 (1H, dd, J=8.8 Hz, 2.6 Hz), 7.24 (1H, d, J=2.6 Hz), 7.29 (1H, dd, J=7.7 Hz, 7.7 Hz), 7.37 (1H, ddd, J=8.1 Hz, 7.7 Hz, 1.7 Hz), 7.54 (1H, s), 7.92 (1H, dd, J=7.7 Hz, 1.7 Hz), 8.73 (1H, brs) FAB-MS(m/e): 388[M+H]$^+$

MANUFACTURING EXAMPLE 117

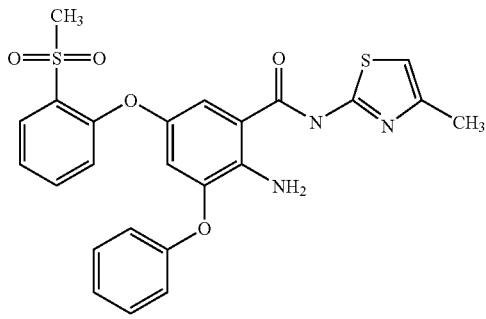

Preparation of 2-amino-3-phenoxy-5-(2-methylsulfonylphenoxy)-N-(4-methylthiazol-2-yl)benzamide $^1$HNMR(CDCl$_3$) δ: 2.33 (3H, s), 3.28 (3H, s), 6.54 (1H, s), 6.81 (1H, d, J=2.4 Hz), 6.86 (1H, d, J=7.8 Hz), 7.05 (2H, d, J=8.2 Hz), 7.16-7.22 (2H, m), 7.19 (1H, d, J=2.4 Hz), 7.37 (2H, t, J=8.2 Hz), 7.50 (1H, dt, J=1.4 Hz, 7.8 Hz), 8.04 (1H, dd, J=1.4 Hz, 7.9 Hz) FAB-MS(m/e): 496[M+H]$^+$

INDUSTRIAL APPLICABILITY

The novel aminobenzamide derivative represented by the formula (I) or its pharmaceutically acceptable salt according to this invention has a glucokinase activation effect, and for example, is useful in the treatment and prevention of diabetes mellitus, and in the prevention of its complications such as diabetic nephropathy, diabetic retinopathy, diabetic neuropathy and diabetic arteriosclerosis.

The invention claimed is:

1. A compound represented by the formula (I):

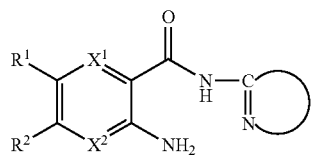

or a pharmaceutically acceptable salt thereof, wherein

R$^1$ is —S(O)p-A, —S—(O)q-B or —O-D, wherein p and q, which are the same or different, each represent an integer from 0 to 2, A is a straight chain C1-C10 alkyl group which may be substituted by R$^{10}$, and B and D each independently represent R$^{12}$ which may be substituted by R$^{10}$;

R$^2$ is a hydrogen atom, a halogen atom, or a straight chain or branched C1-C6 alkyl group which may be substituted by R$^{10}$;

one of X$^1$ or X$^2$ is N and the other is CH;

the formula (II):

shows a monocyclic or bicyclic heteroaryl group which has a nitrogen atom adjacent to the carbon atom bonded to the amide group, and the heteroaryl group may be substituted by R$^{10}$;

R$^{10}$ is R$^{11}$, or a hydrocarbon group which may be substituted by R$^{11}$;

R$^{11}$ is a hydrogen atom, amino, carbamoyl, carbamoylamino, carbamoyloxy, carboxyl, cyano, sulfamoyl, trifluoromethyl, a halogen atom, hydroxyl, formyl, straight chain C1-C6 alkyl, C3-C6 cyclic hydrocarbon, aralkyl, N-aralkylamino, N,N-diaralkylamino, aralkyloxy, aralkylcarbonyl, N-aralkylcarbamoyl, aryl, arylthio, N-arylamino, aryloxy, arylsulfonyl, arylsulfonyloxy, N-arylsulfonylamino, arylsulfamoyl, N-arylcarbamoyl, aroyl, aroxy, C2-C6 alkanoyl, N-C2-C6 alkanoylamino, C1-C6 alkylthio, N-C1-C6 alkylsulfamoyl, N,N-di-C1-C6 alkylsulfamoyl, C1-C6 alkylsulfinyl, C1-C6 alkylsulfonyl, N-C1-C6 alkylsulfonylamino, C1-C6 alkoxy, C1-C6 alkoxycarbonyl or C1-C6 alkylamino; and R$^{12}$ is phenyl, naphthyl, isoxazolyl, isothiazolyl, imidazolyl, oxazolyl, thiazolyl, thiadiazolyl, thienyl, triazolyl, tetrazolyl, pyridyl, pyrazinyl, pyrimidinyl, pyridazinyl, pyrazolyl, pyrrolyl, pyranyl, furyl, furazanyl, imidazolidinyl, tetrahydrofuranyl, piperazinyl, piperidinyl, pyrrolidinyl, morpholino, isoquinolyl, isoindolyl, indolyl, ethylene dioxyphenyl, methylene dioxyphenyl, quinolyl, pyridothiazolyl, dihydroindolyl, tetrahydroquinolinyl, tetrahydroisoquinolinyl, benzimidazolyl, benzoxazolyl, benzothiazolyl, benzotriazolyl or benzofuranyl.

2. The compound according to claim 1, wherein, in formula (I),

R$^{10}$ in A is R$^{111}$, or a hydrocarbon group which may be substituted by R$^{111}$;

R$^{12}$ in B is a phenyl, isothiazolyl, imidazolyl, oxazolyl, thiazolyl, thiadiazolyl, thienyl, triazolyl, tetrazolyl, pyridyl, pyrimidinyl, furyl, ethylene dioxyphenyl, methylene dioxyphenyl, pyridothiazolyl, benzimidazolyl, benzothiazolyl or benzotriazolyl, and the foregoing functional groups may each be substituted by R$^{10}$;

R$^{10}$ in B is R$^{111}$, or a hydrocarbon group which may be substituted by R$^{111}$;

R$^{12}$ in D is a phenyl, naphthyl, pyridyl, pyrazinyl, pyrimidinyl, ethylene dioxyphenyl, methylene dioxyphenyl or quinolyl, and the foregoing functional groups may each be substituted by R$^{10}$;

R$^{10}$ in D is R$^{111}$, or a hydrocarbon group which may be substituted by R$^{111}$;

$R^{10}$ in $R^2$ is $R^{111}$, or a hydrocarbon group which may be substituted by $R^{111}$;

$R^{10}$ in the heteroaryl group represented by formula (II) is $R^{112}$, or a hydrocarbon group which may be substituted by $R^{112}$;

the heteroaryl group of formula (II) is thiazolyl, imidazolyl, isothiazolyl, 1,2,4-thiadiazolyl, 1,3,4-thiadiazolyl, triazolyl, oxazolyl, isoxazolyl, pyrazinyl, pyridyl, pyrimidinyl, pyridothiazolyl or benzothiazolyl;

$R^{111}$ is a hydrogen atom, carbamoyloxy, carboxyl, cyano, trifluoromethyl, a halogen atom, hydroxyl, straight chain C1-C6 alkyl, saturated C3-C9 cyclic hydrocarbon, aralkyl, aryl, arylthio, aroyl, aroxy, C1-C6 alkylthio, C1-C6 alkylsulfonyl, C1-C6 alkoxy or C1-C6 alkoxycarbonyl; and $R^{112}$ is a hydrogen atom, carbamoyl, carboxyl, sulfamoyl, trifluoromethyl, a halogen atom, hydroxyl, aralkyl, aryl, arylthio, arylsulfonyl, aroyl, aroxy, straight chain C1-C6 alkyl, C1-C6 alkylthio, C1-C6 alkylsulfinyl, C1-C6 alkylsulfonyl, C1-C6 alkoxy, C1-C6 alkoxycarbonyl or C3-C6 cycloalkyloxy.

3. The compound according to claim 1, wherein, in formula (I), $R^{10}$ in A is $R^{113}$, or a hydrocarbon group which may be substituted by $R^{113}$;

$R^{12}$ in B is a phenyl, imidazolyl, oxazolyl, thiazolyl, thiadiazolyl, triazolyl, tetrazolyl, pyridyl, pyrimidinyl, ethylene dioxyphenyl, methylene dioxyphenyl or pyridothiazolyl, and the foregoing functional groups may each be substituted by $R^{10}$;

$R^{10}$ in B is $R^{113}$, or a hydrocarbon group which may be substituted by $R^{113}$;

$R^{12}$ in D is a phenyl, naphthyl, pyridyl, ethylene dioxyphenyl or methylene dioxyphenyl, and the foregoing functional groups may each be substituted by $R^{10}$;

$R^{10}$ in D is $R^{113}$, or a hydrocarbon group which may be substituted by $R^{113}$;

$R^{10}$ in $R^2$ is $R^{113}$, or a hydrocarbon group which may be substituted by $R^{113}$;

$R^{113}$ is a hydrogen atom, carboxyl, trifluoromethyl, a halogen atom, hydroxyl, straight chain C1-C6 alkyl, saturated C3-C9 cyclic hydrocarbon, C1-C6 alkoxy, C1-C6 alkoxycarbonyl, C1-C6 alkylthio or C1-C6 alkylsulfonyl;

$R^{10}$ in the heteroaryl group of formula (II) is $R^{112}$, or a hydrocarbon group which may be substituted by $R^{112}$;

$R^{112}$ is a hydrogen atom, carbamoyl, carboxyl, sulfamoyl, trifluoromethyl, a halogen atom, hydroxyl, aralkyl, aryl, arylthio, arylsulfonyl, aroyl, aroxy, straight chain C1-C6 alkyl, C1-C6 alkylthio, C1-C6 alkylsulfinyl, C1-C6 alkylsulfonyl, C1-C6 alkoxy, C1-C6 alkoxycarbonyl or C3-C6 cycloalkyloxy; and the heteroaryl group of formula (II) is thiazolyl, imidazolyl, isothiazolyl, 1,2,4-thiadiazolyl, 1,3,4-thiadiazolyl, triazolyl, oxazolyl, isoxazolyl, pyrazinyl, pyridyl, pyrimidinyl, pyridothiazolyl or benzothiazolyl.

4. The compound according to claim 1, wherein, in formula (I), $R^{10}$ in A is $R^{113}$, or a hydrocarbon group which may be substituted by $R^{113}$;

$R^{12}$ in B is a phenyl, imidazolyl, oxazolyl, thiazolyl, thiadiazolyl, triazolyl, pyridyl, pyrimidinyl, ethylene dioxyphenyl, methylene dioxyphenyl or pyridothiazolyl, and the foregoing functional groups may each be substituted by $R^{10}$;

$R^{10}$ in B is $R^{113}$, or a hydrocarbon group which may be substituted by $R^{113}$;

$R^{12}$ in D is a phenyl, naphthyl, pyridyl, ethylene dioxyphenyl or methylene dioxyphenyl, and the foregoing functional groups may each be substituted by $R^{10}$;

$R^{10}$ in D is $R^{113}$, or a hydrocarbon group which may be substituted by $R^{113}$;

$R^{10}$ in $R^2$ is $R^{113}$, or a hydrocarbon group which may be substituted by $R^{113}$;

$R^{113}$ is a hydrogen atom, carboxyl, trifluoromethyl, a halogen atom, hydroxyl, straight chain C1-C6 alkyl, saturated C3-C9 cyclic hydrocarbon, C1-C6 alkoxy, C1-C6 alkoxycarbonyl, C1-C6 alkylthio or C1-C6 alkylsulfonyl;

$R^{10}$ in formula (II) is $R^{114}$, or a hydrocarbon group which may be substituted by $R^{114}$; and $R^{114}$ is a hydrogen atom, carboxyl, trifluoromethyl, a halogen atom, hydroxyl, aryl, arylthio, straight chain C1-C6 alkyl, C1-C6 alkylthio, C1-C6 alkoxy or C1-C6 alkoxycarbonyl.

5. The compound according to claim 4, wherein $R^1$ in formula (I) is —S(O)p-A or —S—(O)q-B.

6. The compound according to claim 4, wherein $R^1$ in formula (I) is —O-D.

7. A glucokinase activator comprising:

the compound according to claim 1; and a pharmaceutically permitted additive.

8. A method of treating diabetes mellitus or obesity, comprising administering an effective amount of a compound according to claim 1 to a patient in need thereof.

9. A method of treating diabetes mellitus, comprising administering an effective amount of a compound according to claim 1 to a patient in need thereof.

10. A method of treating obesity, comprising administering an effective amount of a compound according to claim 1 to a patient in need thereof.

* * * * *